US010738321B2

(12) United States Patent
Gabriel et al.

(10) Patent No.: US 10,738,321 B2

(45) Date of Patent: Aug. 11, 2020

(54) METHODS AND COMPOSITIONS FOR PREVENTING OR REDUCING INFECTIONS OF CROP PLANTS BY BACTERIAL AND FUNGAL PATHOGENS

(71) Applicants: Integrated Plant Genetics, Inc., Gainesville, FL (US); University of Florida Research Foundation, Inc., Gainesville, FL (US)

(72) Inventors: Dean W. Gabriel, Gainesville, FL (US); Shujian Zhang, Los Alamos, NM (US)

(73) Assignees: INTEGRATED PLANT GENETICS, INC., Gainesville, FL (US); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 324 days.

(21) Appl. No.: 15/605,700

(22) Filed: May 25, 2017

(65) Prior Publication Data

US 2017/0268019 A1 Sep. 21, 2017

Related U.S. Application Data

(63) Continuation-in-part of application No. PCT/US2015/062698, filed on Nov. 25, 2015.

(60) Provisional application No. 62/084,372, filed on Nov. 25, 2014.

(51) Int. Cl.

| | |
|---|---|
| ***C12N 15/82*** | (2006.01) |
| ***A01H 5/00*** | (2018.01) |
| ***C12N 15/113*** | (2010.01) |
| ***C12Q 1/6895*** | (2018.01) |

(52) U.S. Cl.

CPC ........... *C12N 15/8282* (2013.01); *A01H 5/00* (2013.01); *C12N 15/113* (2013.01); *C12N 15/8218* (2013.01); *C12N 15/8281* (2013.01); *C12Q 1/6895* (2013.01); *C12N 2310/11* (2013.01); *C12N 2310/14* (2013.01); *C12N 2310/531* (2013.01); *C12Q 2600/13* (2013.01)

(58) Field of Classification Search

None

See application file for complete search history.

(56) References Cited

U.S. PATENT DOCUMENTS

| | | | | |
|---|---|---|---|---|
| 7,732,593 | B2 | 6/2010 | Zamore et al. | |
| 9,371,541 | B2 * | 6/2016 | Mitchum | C12N 15/8285 |
| 9,433,217 | B2 | 9/2016 | Tang | |
| 2003/0093835 | A1 | 5/2003 | Weigel et al. | |
| 2011/0035839 | A1 | 2/2011 | Lutfiyya et al. | |
| 2011/0251258 | A1 | 10/2011 | Samarsky et al. | |
| 2013/0047298 | A1 | 2/2013 | Tang | |
| 2013/0190387 | A1 | 7/2013 | Feinstein | |
| 2014/0109472 | A1 | 4/2014 | Mirkov et al. | |

FOREIGN PATENT DOCUMENTS

| | | | |
|---|---|---|---|
| CN | 101914540 | A | 12/2010 |
| WO | WO 1999/053050 | A1 | 10/1999 |
| WO | WO 1999/061631 | A1 | 12/1999 |
| WO | WO 2013/032985 | A1 | 3/2013 |
| WO | WO 2016/086142 | A1 | 6/2016 |

OTHER PUBLICATIONS

Doukhanina et al (JBC, 2006, 281: 18973-18801, cited on IDS).*

Lu et al (Frontiers in Plant Science, 2013, 4(157): 1-10).*

Bernstein, et al., "Role for a bidentate ribonuclease in the initiation step of RNA interference." Nature (2001); 409: 363-366.

Corbesier, et al., "FT Protein Movement Contributes to Long-Distance Signaling in Floral." Science (2007); 316(5827): 1030-1033.

De Fougerolles, et al., "Interfering with disease: a progress report on siRNA-based therapeutics." Nature Reviews Drug Discovery (2007); 6: 443-453.

Doukhanina, et al., "Identification and Functional Characterization of the BAG Protein Family in *Arabidopsis thaliana*." The Journal of Biological Chemistry (2006); 281: 18793-18801.

Elbashir, et al., "RNA interference is mediated by 21 and 22 nt RNAs." Genes & Dev. (2001); 15: 188-200.

Hutvágner and Zamore, "RNAi: nature abhors a double-strand." Current Opinion in Genetics & Development (2002); 12(2): 225-232.

International Preliminary Report on Patentability for International Application No. PCT/US2015/062698, dated May 30, 2017, 11 pages.

International Search Report and Written Opinion for International Application No. PCT/US2015/062698, dated Apr. 4, 2016, 18 pages.

Jones-Rhoades, et al., "MicroRNAs and their regulatory roles in plants." Annu Rev Plant Biol (2006); 57: 19-53.

Kawahara, et al., "BAG6/BAT3: emerging roles in quality control for nascent polypeptides." The Journal of Biochemistry (2013); 153(2): 147-160.

Knepper, et al., "The role of NDR1 in pathogen perception and plant defense signaling." Plant Signaling & Behavior (2011); 6(8): 1114-1116.

(Continued)

*Primary Examiner* — Stephen Uyeno

(74) *Attorney, Agent, or Firm* — Cooley LLP

(57) ABSTRACT

The present invention teaches methods and compositions useful for treating, preventing, or curing pathogen infections of living plants. In particular, the present invention teaches methods of enhancing plant response to pathogen-associated molecular patterns. The methods and compositions described herein are effective at treating biotrophic pathogens, including Liberibacters.

9 Claims, 6 Drawing Sheets

Specification includes a Sequence Listing.

(56) References Cited

OTHER PUBLICATIONS

Llave, et al., “Virus-encoded suppressor of posttranscriptional gene silencing targets a maintenance step in the silencing pathway.” PNAS (2000); 97(24): 13401-13406.

Melnyk, et al., “Intercellular and systemic movement of RNA silencing signals.” The EMBO Journal (2011); 30(17): 3553-3563.

NCBI_XM_006491149, Predicted: Citrus sinensis BAG family molecular chaperone regulator 6-like (LOC102629351 ), mRNA. Accession No. XM_006491149. Dec. 27, 2013. [online]. [Downloaded Oct. 26, 2017, 3 pages]. Retrieved from the Internet: <URL: https://www.ncbi.nlm.nih.gov/nucleotide/568876285?report=genbank&log$=nucltop&blast_rank=.

Nykänen, et al., “ATP Requirements and Small Interfering RNA Structure in the RNA Interference Pathway.” Cell (2001); 107(3): 309-321.

Sharp, P.A., “RNA interference—2001.” Genes & Dev. (2001); 15: 485-490.

Turner, et al., “Targeting the HIV-1 RNA leader sequence with synthetic oligonucleotides and siRNA: Chemistry and cell delivery.” Biochimica et Biophysica Acta (BBA)—Biomembranes (2006); 1758(3): 290-300.

NCBI Reference Sequence: XM_006437904.1, Citrus clementina hypothetical protein (CICLE_v10031823mg) mRNA, complete cds, Dec. 20, 2013, 2 pages.

* cited by examiner

METHODS AND COMPOSITIONS FOR PREVENTING OR REDUCING INFECTIONS OF CROP PLANTS BY BACTERIAL AND FUNGAL PATHOGENS

CROSS-REFERENCE TO RELATED APPLICATIONS

This present application is a Continuation-In-Part Application of WIPO International Patent Application No. PCT/US2015/062698 filed Nov. 25, 2015, published as International Publication Number WO 2016/086142 A1, which claims priority to U.S. Provisional Application No. 62/084,372, filed Nov. 25, 2014, each of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: INTE_014_01US_SeqList_ST25.txt, date created: May 24, 2017, file size ≈97.1 kilobytes).

GOVERNMENT LICENSE RIGHTS

This invention was made with government support under 12-8130-0120-CA, 13-8130-0120-CA, and 14-8130-0120-CA awarded by USDA-APHIS. The government has certain rights in the invention.

FIELD OF THE INVENTION

The present disclosure relates to methods and compositions for preventing, eliminating, reducing, or otherwise ameliorating infections and/or damage of crop plants by bacterial and fungal pathogens.

BACKGROUND OF THE INVENTION

All animal and plant cells have a highly regulated cell suicide program designed to limit the damage done to one cell or a group of cells from affecting the entire organism. This is why cells die after radiation damage from sunburn, for example; otherwise, the radiation damage would result in mutations that might result in cancers, or in skin tissue with greatly aged appearance and performance. This suicide program is tightly controlled in all organisms, and it requires a combination of factors to come together to trigger the cell death program. Once initiated, it is irreversible.

Some pathogens have evolved mechanisms to avoid triggering cell death programs, thus circumventing an important plant defense. A solution for regaining control of cell death defense mechanisms is needed to address the emergence and proliferation of and/or damages caused by these pathogens.

SUMMARY OF THE INVENTION

The present disclosure teaches compositions and methods useful for protecting plants against both intracellular and intercellular bacterial and fungal attack, growth and infection, comprising the silencing of BAG6 genes.

The present disclosure relates to methods and compositions for preventing, reducing, eliminating or otherwise ameliorating infections and/or damage of crop plants by bacterial and fungal pathogens. The percentage reduction in pathogen infection and/or plant damage for plants protected using the compositions and methods of the present invention is at least 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% greater/better when compared to an appropriate control or check plant grown under the same plant husbandry conditions. The amount of pathogen infection and/or plant damage can be measured using methods well known to those skilled in the art. Plant infection, e.g., can be measured as the percentage of necrotic tissue on the plants. Plant damage, e.g., can be measured as total yield of a specific plant part (e.g., number or weight of seeds, number or weight of pods, plant weight, plant height, number of weight of flowers, root mass measured in volume or by weight, etc.). An appropriate control or check plant is one in which the BAG6 gene(s) have not been silenced as they are silenced in the test plant(s) according to the compositions and methods of the present invention.

Specifically, the disclosure teaches use of ribonucleic acid (RNA) interference (RNAi), double stranded RNA (dsRNA), and/or anti-sense RNA (aRNA or asRNA) for their potential to remove a natural anti-apoptotic protein blockade that specifically dampens the plant apoptotic response to pathogens. More specifically, the disclosure teaches the gene specific targeting of BAG6 homologs to control biotrophic pathogens, particularly those caused by Liberibacters.

In one embodiment, the specific target is the *citrus BAG6* homolog (CiBAG6) of the rootstock Carrizo (*Citrus sinensis* X *Poncirus trifoliata*; SEQ ID NO: 1). In another embodiment, the CiBAG6 homolog is from Clementine tangerine, *Citrus* x *clementina*, and more specifically based on the complete DNA sequence found in the Clementine genome (clementine0.9_012925m, SEQ ID NO: 8), which we name CiBAG6C.

In another embodiment, the sweet orange genome homolog (orange1.1g046468m) is utilized, since the orange1.1g046468m fragment and clementine0.9_012925m share about 98.1% identity at DNA level.

In another embodiment, the CiBAG6 homolog of *Citrus sinensis* (sweet orange) cultivar Hamlin (SEQ ID NO: 9) was used.

In further embodiments, any segment, section or part of the full length sweet orange genome mRNA homolog, GenBank LOC102629351, XM_015534243 (SEQ ID NO: 10) can be used, including both the 5' and 3' untranslated regions (i.e., not only the fragments currently deposited in GenBank). For example, when comparing a 497 bp experimentally derived sequence from Hamlin sweet orange (SEQ ID NO: 9) to the same 497 bp experimentally derived sequence from Carrizo rootstock (positions 135 to 631 in SEQ ID NO: 1), the sequences were about 97% identical. When the same Hamlin and Carrizo sequences were compared to the equivalent region of Valencia orange (SEQ ID NO: 10), they were about 98.2% and about 97.6% identical, respectively. Indeed, any BAG6 homolog, including the 5' and 3' untranslated regions found in any citrus host could be used by those skilled in the art for the purpose of silencing the citrus CiBAG6 gene, since it is well known that the untranslated regions of mRNA can serve as excellent targets of siRNAs (Deng et al 2012; Lai et al 2013). Thus in some embodiments, the PCR cloning strategy as described herein from Carrizo, Hamlin, or Valencia or any other citrus source is likely to be useful for identification of a CiBAG6 homolog useful for silencing of the CiBAG6 in any citrus host, including any species of the genus citrus. Citrus is a genus of flowering trees and shrubs in the rue family, Rutaceae.

Plants in the genus produce citrus fruits, including important crops like oranges, lemons, grapefruit, pomelo and limes. Given the current and growing availability of genomic DNAs, multiple corresponding BAG6 genes can now readily be identified by those skilled in the art from virtually any plant source for which a DNA sequence is available using a PCR cloning strategy similar to that taught here, including BAG6 genes from citrus and other woody species such as *Malus domestica* apple, *Theobroma cacao* cocoa, *Prunus persica* peach, *Populus deltoides* poplar, vines such as *Vitis vinifera* grape, and agronomic crop plants such as *Gossypium hirsutum* cotton, *Glycine max* soybean, *Arabidopsis* and many others.

The present invention also provides compositions and methods for the protection and/or curing of plants from infections caused by biotrophic bacteria and fungi by complete or partial (i.e., incomplete) suppression of BAG6 homologs. In one embodiment, the invention provides compositions and methods for the protection of *citrus* cells from infection by biotrophs. In some embodiments, the invention provides compositions and methods for the protection and curing of *citrus* phloem from infection by *Liberibacter asiaticus* (Las).

The present invention also provides compositions and methods for the protection of grafted scions that are non-transgenic by the use of rootstock for which one or more BAG6 genes have been silenced or attenuated using the methods of the present invention.

In some embodiments, the present invention provides compositions and methods for the protection and curing of nontransgenic citrus trees that are infected by using a polynucleotide spray, including, e.g., via a double stranded RNA (dsRNA) spray that can suppress BAG6 homolog expression. In some embodiments, the present invention provides compositions and methods for the protection and curing of citrus phloem cells from infection by Liberibacters, including Las, or citrus mesophyl cells attacked by *X. citri.*

In some embodiments, the present invention teaches that dsRNA about 10, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 base pairs in length or as short fragments of about base pairs in length, can induce RNAi and suppress BAG6 homolog expression in *citrus* when applied as sprays or as soil drench from the outside of the *citrus* plant. In some embodiments well known to those skilled in the art, the RNAi can be induced not simply by application of dsRNA, but by any double stranded polynucleotide, including synthetic polynucleotides. In some embodiments well known to those skilled in the art, antisense polynucleotides can be formed not simply from polynucleotides, but also from phosphorodiamidate morpholino oligomers (PMOs).

In some embodiments, the present invention teaches that RNAi can travel across the graft union from transgenic rootstock to nontransgenic scion, thus obviating the need for scion transformation as well as reducing the regulatory burden attendant to marketing transgenic plants that may shed transgenic pollen and or marketing transgenic fruit. In addition, an RNA movement leader is disclosed that confers the capacity to move an antisense RNA (aRNA) across a graft union from transgenic rootstock to nontransgenic scions. Although both the RNAi and aRNA are now thought to work by activating the same pathway, the processes result in differing magnitudes of the same silencing effect on the targeted gene.

The present invention also provides silencing constructs based on phloem specific gene expression that: 1) result in keeping the engineered silencing limited to phloem only, and 2) allows spread from phloem to mesophyl and epidermal cells.

In some embodiments, the present invention teaches compositions and methods for repressing, preventing or otherwise reducing bacterial or fungal infections of a plant comprising expressing an antisense or RNA interference construct based on a BAG6 protein or nucleic acid sequence.

In some embodiments the present invention teaches methods of identifying BAG6 family genes through the use of AtBag6, CiBag6, including homologs and orthologs of AtBag6 and CiBag6, and/or through use of SEQ ID NO: 1 or SEQ ID NO: 8, or SEQ ID NO: 9 or SEQ ID NO. 10 or a protein or protein fragment encoded by an amino acid sequence having at least 70%, or at least 80%, or at least 90%, or at least 95%, or at least 98% amino acid sequence similarity to the predicted peptide sequence encoded by SEQ ID NO: 1 or SEQ ID NO: 8 or SEQ ID NO: 9 or SEQ ID NO: 10. In certain embodiments, the present invention teaches an isolated nucleic acid molecule coding for at least 15, 16, 17, 18, 19, 20, 21, 22, 23, 24, or 25 contiguous bases pairs of homology to AtBag6 or CiBag6, and/or SEQ ID NO: 1 or SEQ ID NO: 8 or SEQ ID NO: 9 or SEQ ID NO: 10 that can be used for controlling plant diseases. In other embodiments, the methods and compositions of the present invention can be used to treat, reduce, or eliminate disease in *citrus* plants.

In some embodiments, the present invention teaches the complete or partial (i.e., incomplete) down-regulation of a BAG6 gene to treat diseases caused by biotrophic plant pathogens. In some embodiments, the disease treated by the methods and compositions of the present invention is caused by a *Liberibacter*. In some embodiments, the disease treated by the methods and compositions of the present invention is caused by a *Liberibacter* infecting a *citrus* plant. In certain embodiments, the *Liberibacter* of the present invention is Ca. *Liberibacter asiaticus* (Las).

In some embodiments, the present invention teaches that the isolated nucleic acid molecules of the present invention are operably-linked to a nucleic acid molecule coding for an endoplasmic reticulum (ER) retention signal sequence.

In some embodiments, the present invention teaches that the isolated nucleic acid molecules of the present invention are operably-linked to a nucleic acid molecule coding for one or more expression control elements. In some embodiments, the nucleic acids of the present invention are expressed using a CaMV 35S or an AtSuc2 promoter. In some embodiments, the present invention teaches vectors for expressing the nucleic acids taught by the present invention.

In some embodiments the present invention teaches a host cell transformed to contain the at least one of the nucleic acid molecules of the present invention. In other embodiments, the host cell of the present invention is a eukaryotic or prokaryotic host cell.

In some embodiments, the present provides methods of enhancing a plant's immune response to infection, said method comprising complete or partial (i.e., incomplete) down-regulating the expression of a BAG6 gene, wherein said plant has increased NDR1 expression in response to "pathogen associated molecular patterns" (PAMPs) compared to a control plant with unaltered BAG6 gene expression.

In some embodiments, the present invention teaches methods of enhancing a plant's immune response to infection, said methods comprising down-regulating the expression of a BAG6 gene, wherein said plant has increased Non race-specific Disease Resistance 1 (NDR1) expression in response to PAMP exposure compared to a control plant with unaltered BAG6 gene expression.

In some embodiments, the present disclosure teaches the down-regulation of one or more BAG6 genes with at least 70%, or at least 80%, or at least 90%, or at least 95%, or at least 98% sequence identity to SEQ ID NO: 1 or SEQ ID NO: 8 or SEQ ID NO: 9 or SEQ ID NO. 10. In some embodiments, the present invention teaches the use of antisense RNA for down-regulating BAG6 genes. In some embodiments, the present invention teaches the use of RNAi for down-regulating BAG6 genes. The RNAi can be achieved in multiple ways. In some embodiments, the RNAi is achieved by topical spray application of dsRNAs ranging in size from about 200 to about 2,000 bp in length ("long dsRNAs"). In some embodiments, the RNAi is achieved by topical spray applications of dsRNAs predigested to about 15 to 30 bp in size, also known as small interfering RNAs ("siRNAs"). In some embodiments, the RNAi is achieved by topical spray applications of dsRNAs predigested to ca. 23 bp in size, also known as siRNAs. In some embodiments, the RNAi is achieved by either siRNAs or long dsRNAs applied by root applications or direct trunk injections.

In some embodiments, the methods of the present invention increase plant resistance to at least one biotrophic pathogen. In certain embodiments, the biotrophic pathogens of the present invention are Liberibacters.

In some embodiments, the present invention teaches a recombinant or transgenic plant, or part thereof, comprising a construct comprising a polynucleotide capable of triggering RNA interference and down-regulating a BAG6 gene with at least 70%, or at least 80%, or at least 90%, or at least 95%, or at least 98% sequence identity to SEQ ID NO: 1 or SEQ ID NO: 8 or SEQ ID NO: 9 or SEQ ID NO: 10, wherein said recombinant plant exhibits enhanced response to PAMP triggers. In other embodiments, the present disclosure provides transgenic plant cells, transgenic seeds, and progeny plants, and parts thereof, derived from transgenic plants, comprising a recombinant nucleic acid construct comprising a nucleic acid molecule comprising at least 15, 16, 17, 18, 19, 20, 21, 22, 23, 24, or 25 contiguous nucleotides from SEQ ID NO: 1 or SEQ ID NO: 8 or SEQ ID NO: 9 or SEQ ID NO: 10 operably linked to a heterologous promoter, that when transcribed reduces expression of a BAG6 gene in a plant.

In some embodiments, the present invention teaches a recombinant plant comprising a construct comprising a polynucleotide capable of triggering RNAi and down-regulating a BAG6 gene with 70%, or at least 80%, or at least 90%, or at least 95%, or at least 98% sequence identity to SEQ ID NO: 1 or SEQ ID NO: 8 or SEQ ID NO: 9 or SEQ ID NO: 10, wherein said recombinant plant exhibits enhanced resistance to Liberibacters and confers said resistance long distances, including across the graft union to nontransgenic scions.

In some embodiments, the present invention teaches a topically applied spray formulation comprising a polynucleotide capable of triggering RNA interference in nontransgenic plants and down-regulating a BAG6 gene with at least 70%, or at least 80%, or at least 90%, or at least 95%, or at least 98% sequence identity to SEQ ID NO: 1 or SEQ ID NO: 8 or SEQ ID NO: 9 or SEQ ID NO: 10, wherein said spray formulation confers enhanced resistance to Liberibacters and confers said resistance long distances in the plant.

In some embodiments, the present invention teaches a topically applied root application or soil drench formulation comprising a polynucleotide capable of triggering RNAi in nontransgenic plants and down-regulating a BAG6 gene with at least 70%, or at least 80%, or at least 90%, or at least 95%, or at least 98% sequence identity to SEQ ID NO: 1 or SEQ ID NO:8 or SEQ ID NO: 9 or SEQ ID NO: 10, wherein said spray formulation confers enhanced resistance to Liberibacters and confers said resistance long distances throughout the plant.

In other embodiments, the present invention teaches a grafted plant with recombinant rootstock and an untransformed scion.

DETAILED DESCRIPTION OF THE INVENTION

Apoptosis

Figure 1:
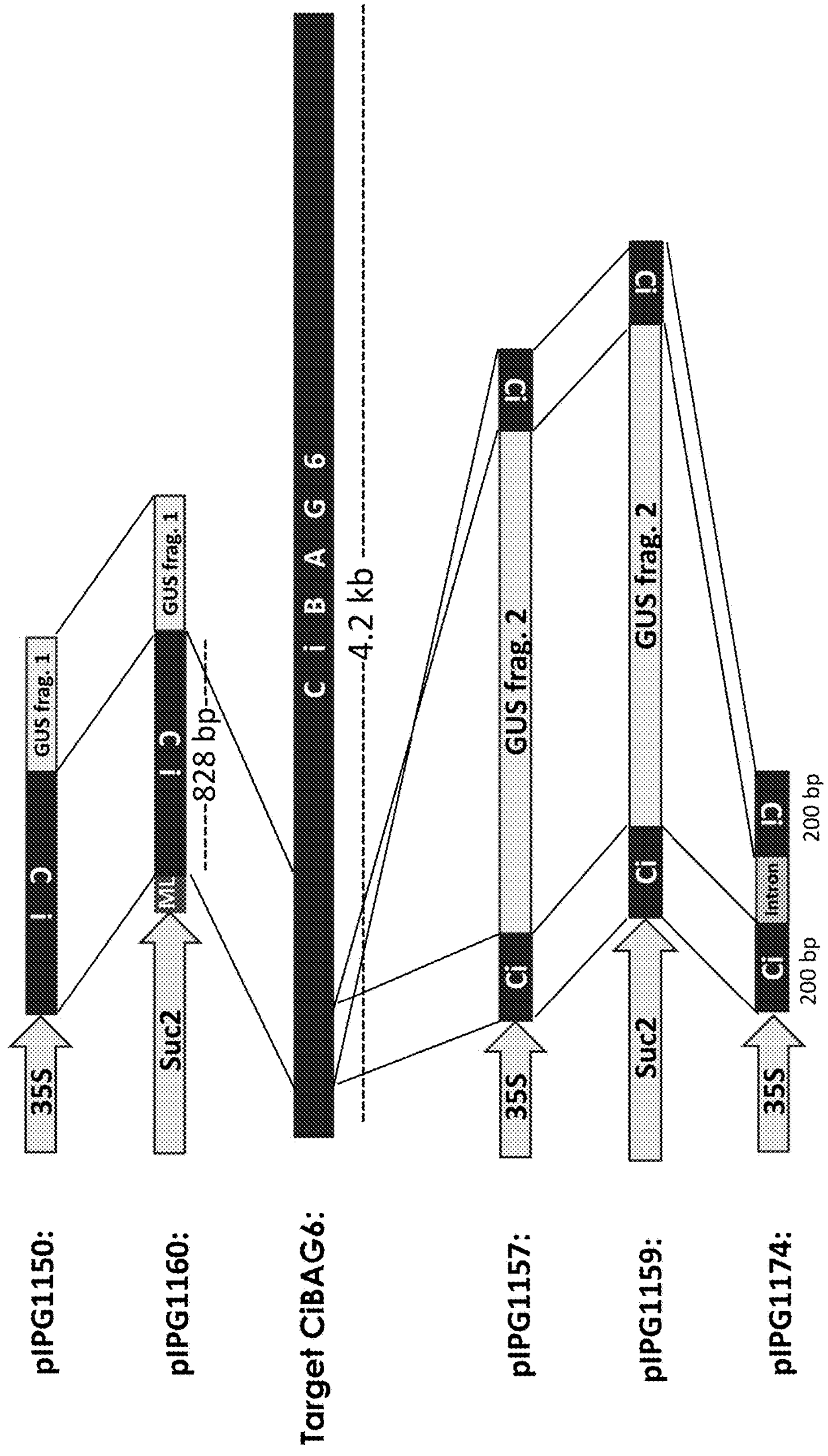
FIG. 1. Schematic diagrams of the constructs used to silence the CiBag6 gene. Carrizo Cibag6 cDNA is diagrammed above the constructs. Constructs pIPG1150 and pIPG1160 are antisense (aRNA) and constructs pIPG1157, pIPG1159 and pIPG1174 are inverted repeat constructs. The CaMV 35S promoter (35S) and *Arabidopsis* sucrose transporter AtSuc2 gene promoter (Suc2) were used as indicated. In addition, a 104 nucleotide movement leader (ML) was used to construct pIPG1160, and two uidA fragments (labeled "GUS frag. 1", 516 bp and "GUS frag. 2", 1848 bp) taken from the 5' end of the uidA gene from pCAMBIA2301 were used as indicated. Finally, a 190 bp catalase intron ("intron") from pCAMBIA was used to construct pIPG1174 as shown.

Type I programmed cell death (PCD) or apoptosis, is a genetically programmed and highly regulated cell death mechanism found in plant and animal cells that allows damaged cells to commit suicide. Apoptosis is critically important for elimination of damaged or infected cells that could compromise the function of the whole organism. Typical triggers of apoptosis are environmental insults or stresses that can damage cells or their DNA content. Reactive oxygen species (ROS), including superoxide anions, hydrogen peroxide, nitric oxide and free hydroxide radicals are produced in response to stress, and particularly stress causing mitochondrial damage (Portt, et al., 2011). ROS production is a first line of defense in animal and plant cells against biotic disease agents, such as bacteria and fungi. ROS is also one of the major signals that can trigger apoptosis. In addition to ROS production, stress also activates production of the protein “Bax”, and the sphingolipid “ceremide”, and all three are direct proapoptotic messengers. These three major proapoptic messengers can to act independently of one another, since increases in the levels of any one of them (Bax, ROS, or ceramide) is sufficient to trigger apoptosis, but most often, they appear to act in concert.

Pathogens that benefit from plant cell death, such as *Phytopthora, Ralstonia, Pseudomonas* and *Xyella* are necrotrophic in lifestyle; that is, they kill host cells in order to provide nutrients to sustain in planta population growth. Such pathogens may do little to suppress apoptosis (type I) or necrotic (type III) programmed cell death (Portt, et al., 2011). Other pathogens, such as the obligate fungal parasites (rusts and mildews) and some bacteria, such as *Rhizobium*, are biotrophic, and must establish intimate cell membrane to membrane contact using haustoria or infection threads.

Programmed Cell Death for Controlling Infections

Liberibacters are the ultimate form of biotroph, living entirely within the living host cell and surrounded by host cell cytoplasm. For biotrophs, host cell death would be expected to severely limit growth in planta. Liberibacters, which must live entirely within living phloem cells, would have no options if their phloem host cells simply died. Biotrophic pathogens typically have multiple mechanisms available to suppress apoptosis or necrotic programmed cell death. In the case of necrotrophic pathogens (those that rely on killing plant cells in order to feed on the contents), suppressing host cell death results in denial of nutrients, and resistance is the result. Necrotrophic pathogens naturally trigger PCD.

*Candidatus Liberibacter* is a genus of Gram-negative bacteria in the Rhizobiaceae family. Detection of the liberibacters is based on PCR amplification of their 16S rRNA gene with specific primers. Members of the genus are plant pathogens mostly transmitted by psyllids. The genus was originally spelled *Liberobacter.*

Liberibacters and Other Biotrophic Bacteria

By contrast, prototrophic pathogens rely on fully functional living cells to survive. For example, all species and strains of the genus *Liberibacter* live in plants entirely within living plant phloem cells. The first species described was *Candidatus Liberibacter asiaticus* (Las), the causal agent of Huanglongbing (HLB), commonly known as citrus “greening” disease. HLB is lethal to citrus and one of the top three most damaging diseases of citrus. The second species described was found in Africa, Ca. *L. africanus* (Laf), and the third, Ca. *Liberibacter americanus* (Lam) was found in Brazil. All three cause HLB in citrus. Beside the three citrus Liberibacters associated with HLB, three non-citrus *Liberibacter* species have been described. Ca. *L. solanacearum* (Lso), has been identified as the causal agent of serious diseases of potato (“Zebra chip”), tomato (“psyllid yellows”) and other solanaceous crops in the USA, Mexico, Guatemala, Honduras, and New Zealand (Hansen, et al., 2008; Abad, et al., 2009; Liefting, et al., 2009; Secor, et al., 2009). More recently, a different haplotype of Lso was found infecting carrots in Sweden, Norway, Finland, Spain and the Canary Islands (Alfaro-Fernandez, et al., 2012a, 2012b Munyaneza, et al., 2012a, 2012b; Nelson, et al., 2011). A fifth species of *Liberibacter*, Ca. *L. europaeus* (Leu) was recently found in the psyllid *Cacopsylla pyri*, the vector of pear decline phytoplasma. Finally, a sixth species of *Liberibacter, Liberibacter crescens* (Lcr), was recently characterized after isolation from diseased mountain papaya (Babaco). Except for Lcr, which is not known to be pathogenic, all other described Liberibacters are pathogenic and must be injected into living plant cells by specific insects. Furthermore, the pathogenic Liberibacters can only live within specific insect and plant cells; as obligate parasites, they do not have a free-living state—they are extreme biotrophs.

As an example of an ordinary biotroph, *Xanthomonas citri*, which causes citrus canker disease, invades the air spaces within a leaf and relies on inducing cell divisions in living cells in order to rupture the leaf surface (Brunings and Gabriel, 2003). Obviously, for biotrophs, host cell death would be expected to severely limit growth in planta. Liberibacters, which must live entirely within living phloem cells, would have no options if their phloem host cells simply died.

Mechanisms of Avoiding Programmed Cell Death

The genomes of Las and Lam differ (among other things) in that Las has 4 copies of peroxidase (Zhang, et al., 2011), and Lam has 2 (Wulff, et al., 2014). These are critical lysogenic conversion genes (conferring ability to colonize a plant or insect). With both Las and Lam (and likely Lso), these genes are amplified in copy number on a plasmid prophage to increase transcript copy number, and therefore, protein levels (Zhang, et al., 2011). Peroxidases degrade reactive oxygen species (ROS), like hydrogen peroxide. ROS production is one of the primary insect and plant host defenses against microbes. Since Liberibacters colonize living phloem cells and multiply within the plant cell cytoplasm, the ability to degrade ROS is a critical matter of survival to *Liberibacter.*

Peroxidases also suppress PCD, and since ROSS are strong pro-apoptotic inducers of PCD, particularly under certain nutrient deficiencies, the ability to absorb and degrade ROS is a matter of survival for the simple reason of keeping its host cell alive. Since Liberibacters can occupy a significant volume of cell cytoplasm, the ability to absorb and degrade ROS may be critical to suppressing citrus cell apoptosis. Lam causes a lot more disease than Las, but is always present in significantly lower titer (Lopes, et al., 2009). It is possible that the higher titer of Las is allowed by the activity of four peroxidases, which in combination with the higher titer allow a greater total absorption and inactivation of ROS, reducing the ROS induced proapoptotic effect on the citrus cell.

Plant pathogens provide a series of molecular signals that are detected by the plant and can trigger PCD. There are also built in brakes on the plant PCD system, and some of these have been exploited in transgenic plants in recent successful attempts to artificially suppress the cell death program. Avoidance of triggering PCD by biotrophs involves eliminating by evolution over time, to the greatest possible extent, production of "pathogen associated molecular patterns" (PAMPs). PAMPs are detected by plants as alien molecules and trigger strong defense responses called "innate immunity" in plants.

Innate immunity involves production of ROS, including superoxide anions, hydrogen peroxide, nitric oxide and free hydroxide radicals. ROS are produced in response to stress, and particularly stress causing mitochondrial damage (Portt, et al., 2011). ROS production is a first line of defense in animal and plant cells against biotic disease agents, such as bacteria and fungi. ROS is also one of the major signals that can trigger apoptosis. The genome sequences of both Las and Lam are highly reduced in size (both are 1.26 Mb) as compared with their closest *Rhizobium* relatives (genome sizes >6.4 Mb); significantly, both Las and Lam appear to lack flagella, a known PAMP, although both encode structural genes for flagellin. In addition, Lam lacks most of the genes needed to make lipopolysaccharide (LPS), a particularly potent PAMP and an important defensive barrier molecule integral to the outer membrane of most Gram negative bacteria.

Plant Regulators of Programmed Cell Death

Anti-apoptosis proteins have distinct and often specific anti-apoptotic effects when expressed in transgenic plants. Overexpression of many of the genes encoding these anti-apoptotic factors, including genes encoding a variety of chaperones, heat shock proteins and ROS scavengers, such as superoxide dismutase and peroxidases, can prevent apoptosis and are therefore cytoprotective from the effects of biotic and abiotic stresses. The Bcl-2 family is a well-characterized group of "core" anti-apoptotic regulators with strong general effects; these proteins inhibit production of Bax, and without affecting production of ROS. The Bcl-2 proteins, if overexpressed, broadly inhibit apoptosis in plants caused by both biotic and abiotic stresses. For example, expression of antiapoptotic genes bcl-xL (derived from chickens) and ced-9 (derived from *Caenorhabditis elegans*) blocked apoptosis in tomato and enhanced tolerance to viral induced necrosis and abiotic stress (Xu, et al., 2004). Similarly, expression of antiapoptotic genes bcl-2 (derived from humans), and op-iap (derived from baculovirus) blocked apoptosis in tobacco and conferred resistance to several necrotrophic fungal pathogens (Dickman, et al., 2001). No plant homologs of Bcl-2 have been identified to date.

There are also reports of an anti-apoptotic role for basic, but not acidic, pathogenesis related (PR) proteins, and many of these affect both biotic and abiotic stress induced responses. For example, a basic PR-1 protein from pepper, when overexpressed in transgenic tobacco, was shown to enhance heavy metal tolerance and to provide significantly higher resistance against *Phytopthora, Ralstonia solanacearum* and *Pseudomonas syringae* (Sarowar, et al., 2005). In all cases, necrosis in the abiotically- or biotically-stressed transgenic lines was greatly reduced compared to control lines. Clearly, the necrosis elicited by these pathogens is not a direct effect of pathogenic enzymes, but an indirect effect that triggers PCD that results in necrosis. Similarly, a basic PR-1 protein from grape, when overexpressed in transgenic tobacco, was shown to provide significantly reduced disease lesions in challenge inoculations with *P. syringae* (Zhijian, et al., 2010). Gilchrist and Lincoln (2011) reported that a grape PR-1 protein, when expressed in several transgenic host species, would suppress apoptosis, and in so doing, provide greatly improved tolerance to *Xylella fastidiosa* by blocking symptom induction, which in turn leads to a major reduction in total bacterial growth in planta. It should be noted that only a few members from the plant PR-1 family showed inducible expression by pathogens and possessed inhibitory activity against pathogens (Li, et al., 2011). For example, *Arabidopsis* and rice contain 22 and 39 PR-1 type genes, but only 1 and 2 members, respectively, have been found to be inducible by pathogen or insect attacks (Van Loon, et al., 2006).

BAG6 as a Regulator of Programmed Cell Death

The present disclosure is based in part on the inventors' unexpected discovery that the down regulation of citrus BAG6 gene in plants leads to an increased programmed cell death response to pathogen incursions.

In some embodiments, the present invention teaches that the down-regulation of BAG6 in plants leads to increased production of defense response protein NDR-1. This increased NDR-1 production in BAG6 silenced citrus is particularly significant, since elevated levels of this gene are known to increase basal resistance to both bacteria and fungi in *Arabidopsis*, and is suggested to be likely to increase resistance to Las in citrus (Lu, et al., 2013).

Thus in some embodiments, the present disclosure teaches the down-regulation of BAG6 genes for increasing plant resistance to pathogens. In some embodiments, the present disclosure teaches the down-regulation of BAG6 genes to increase resistance of biotrophic pathogens. In other embodiments, the disclosure teaches down-regulation of Bag6 genes to increase resistance to citrus greening disease caused by Las, Lam, and Lso.

In some embodiments, the present disclosure teaches the down-regulation of Carizzo-CiBAG6 (SEQ ID NO: 1). In some embodiments, the present disclosure teaches the down-regulation of Clementine-CiBAG6 (SEQ ID NO: 8). In some embodiments, the present disclosure teaches the down-regulation of Hamlin-CiBAG6 (SEQ ID NO: 9). In some embodiments, the present disclosure teaches the down-regulation of Valencia-CiBAG6 (SEQ ID NO: 10).

It has not been anticipated, expected, nor suggested in any plant system that silencing of a BAG6 gene, which results in suppressing production of the corresponding BAG6 protein, could increase levels of expression of downstream defense response proteins and be protective against pathogen infection or the effects of pathogen infections.

The disclosure here that silencing of BAG6 in citrus (and not overexpression, like the other examples presented herein) enhances production of defense response proteins and is protective from the effects of pathogen infection is therefore a surprising discovery.

For gene silencing purposes, both antisense RNA or RNAi may be used instead activate the RNAi pathway, although the processes result in differing magnitudes of the same downstream effects.

Controlled Regulation of BAG6 by Selective Spatial Temporal Silencing

By artificially removing one of the natural plant inhibitors of programmed cell death (PCD), specifically the one engaged when plants detect the presence of a pathogen, the present disclosure teaches effective defenses in response to pathogens in an unusually rapid manner. If this brake removal occurred generally in all plant tissues, it could have the undesirable result of making the plant more susceptible to necrotrophic pathogens.

However, if the PCD brake removal can be limited to just the phloem and nearby cells, then there should be no necrotrophic pathogen advantage, since necrotrophs do not attack phloem as a first target. Since *Liberibacter* and *Xanthomonas* are two bacterial genera that cause major plant diseases and are prototrophic, selective removal of a PCD brake control can confer immunity to *Liberibacter, Xanthomonas* and other biotrophic pathogens, including fungi, without undesired effects of increasing susceptibility to necrotrophs.

In some embodiments, the present disclosure teaches two RNA-based methods for selectively silencing the Bag6 gene in such a way that: 1) only the rootstock was transgenic, leaving the scion grafted onto the rootstock nontransgenic; 2) the RNA used was limited to phloem cells only (where Las resides), and 3) the RNA used in another case allowed limited migration to cells outside the phloem. The present disclosure teaches that the selective silencing methods of the present disclosure are effective at increasing basal defense responses and disease resistance in both the transgenic rootstock and the nontransgenic scion. This disclosure is of significant benefit to U.S. fruit crop producers, since the resulting plants became resistant to severe disease, had nontransgenic scions, and importantly for marketing, non-transgenic plants. In some embodiments, the term recombinant and transgenic are used interchangeably in this application.

As used herein, the term "brake" for programmed cell death can be used interchangeably with the term inhibition of PCD, or inhibitor of PCD.

Sequence Identity

In some embodiments, the present invention teaches the down-regulation of a CiBAG6 homolog or ortholog, in which said homolog or ortholog shares at least 99.9%, 99.8%, 99.7%, 99.6%, 99.5%, 99.4%, 99.3%, 99.2%, 99.1%, 99%, 98.9%, 98.8%, 98.7%, 98.6%, 98.5%, 98.4%, 98.3%, 98.2%, 98.1%, 98%, 97.9%, 97.8%, 97.7%, 97.6%, 97.5%, 97.4%, 97.3%, 97.2%, 97.1%, 97%, 96.9%, 96.8%, 96.7%, 96.6%, 96.5%, 96.4%, 96.3%, 96.2%, 96.1%, 96%, 95.9%, 95.8%, 95.7%, 95.6%, 95.5%, 95.4%, 95.3%, 95.2%, 95.1%, 95%, 94.9%, 94.8%, 94.7%, 94.6%, 94.5%, 94.4%, 94.3%, 94.2%, 94.1%, 94%, 93.9%, 93.8%, 93.7%, 93.6%, 93.5%, 93.4%, 93.3%, 93.2%, 93.1%, 93%, 92.9%, 92.8%, 92.7%, 92.6%, 92.5%, 92.4%, 92.3%, 92.2%, 92.1%, 92%, 91.9%, 91.8%, 91.7%, 91.6%, 91.5%, 91.4%, 91.3%, 91.2%, 91.1%, 91%, 90.9%, 90.8%, 90.7%, 90.6%, 90.5%, 90.4%, 90.3%, 90.2%, 90.1%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, or 40% sequence identity with SEQ ID NO:1 or SEQ ID NO: 8 or SEQ ID NO:9 or SEQ ID NO. 10.

In some embodiments, the present invention the down-regulation of a CiBAG6 homolog or ortholog, in which said homolog or ortholog shares nucleotide sequence encoding an amino acid sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, sequence identity to SEQ ID NO:11 or SEQ ID No: 12 or SEQ ID NO. 13.

In some embodiments, the sequence identity of the CiBAG6 homolog or ortholog is calculated based on the alignment and comparison of each gene's nucleic acid sequence. In other embodiments, the sequence identity of the homolog or ortholog is calculated based on the alignment and comparison of the encoded protein.

In some embodiments, the alignments and sequence identity calculations of the present invention are calculated using ClustalOmega software with default settings.

In some embodiments, the CiBAG6 gene homologs and orthologs of the present disclosure will encode for conservative amino acid substitutions. Conservative amino acid substitutions are those substitutions that, when made, least interfere with the properties of the original protein, that is, the structure and especially the function of the protein is conserved and not significantly changed by such substitutions. Conservative substitutions generally maintain: (a) the structure of the polypeptide backbone in the area of the substitution, for example, as a sheet or helical conformation; (b) the charge or hydrophobicity of the molecule at the target site; or (c) the bulk of the side chain. Further information about conservative substitutions can be found, for instance, in Ben Bassat, et al. (*J. Bacteriol.,* 169:751-757, 1987), O'Regan, et al. (*Gene,* 77:237-251, 1989), Sahin-Toth, et al. (*Protein Sci.,* 3:240-247, 1994), Hochuli, et al. (*Bio/Technology,* 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff, et al., *Proc. Natl. Acad. Sci. USA,* 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

TABLE 1

| BLOSUM substitution Matrix | | | |
|---|---|---|---|
| Original Residue | Very Highly-Conserved Substitutions | Highly Conserved Substitutions (from the Blosum90 Matrix) | Conserved Substitutions (from the Blosum65 Matrix) |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some embodiments, orthologs and homologs of the present invention can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can are found to be replaced with a different hydrophobic residue (such as Leu, Ile, Val, Met, Phe, or Trp) to create a variant functionally similar to the disclosed an amino acid sequences encoded by the nucleic acid sequences of CiBAG6.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of CiBAG6.

Recombinant DNA Constructs

Another aspect of this invention provides a recombinant nucleic acid construct including a heterologous promoter operably linked to DNA including at least one segment of 15, 16, 17, 18, 19, 20, 21, 22, 23, 24, or 25 more contiguous nucleotides with a sequence of about 70% to about 100% identity with a segment of equivalent length of a DNA having a sequence selected from the group consisting of SEQ ID NO:1 and SEQ ID NO:8 and SEQ ID NO:9 and SEQ ID NO. 10 The recombinant nucleic acid constructs are useful in providing a plant having improved resistance to bacterial or fungal infections, e.g., by expressing in a plant a transcript of such a recombinant nucleic acid construct. The contiguous nucleotides can number more than 15, 16, 17, 18, 19, 20, 21, 22, 23, 24, 25, 26, 27, 28, 29, 30, or greater than 30, e.g., about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, or greater than 900 contiguous nucleotides from SEQ ID NO:1 or SEQ ID NO:8 or SEQ ID NO:9 or SEQ ID NO:10.

The contiguous nucleotides can number more than about 900, about 1000, about 1100, about 1200, about 1300, about 1400, about 1500, about 1600, about 1700, about 1800, about 1900, about 2000, about 2100, about 2200, about 2300, about 2400, about 2500 contiguous nucleotides from SEQ ID NO:1 or SEQ ID NO:8 or SEQ ID NO:9 or SEQ ID NO:10.

In some embodiments, the recombinant nucleic acid construct of this invention is provided in a recombinant vector. By "recombinant vector" is meant a recombinant polynucleotide molecule that is used to transfer genetic information from one cell to another. Embodiments suitable to this invention include, but are not limited to, recombinant plasmids, recombinant cosmids, artificial chromosomes, and recombinant viral vectors such as recombinant plant virus vectors and recombinant baculovirus vectors.

RNA Interference

Sequence-selective, post-transcriptional inactivation of expression of a target gene can be achieved in a wide variety of eukaryotes by introducing double-stranded RNA (dsRNA) corresponding to the target gene, a phenomenon termed RNA interference (RNAi). RNAi occurs when an organism recognizes dsRNA molecules and hydrolyzes them. The resulting hydrolysis products are small RNA fragments of 15, 16, 17, 18, 19, 20, 21, 22, 23 or 24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs (Jones-Rhoades et al. (2006) *Annu. Rev. Plant Biol.* 57, 19-53; Llave et al. (2002) *Proc. Natl. Acad. Sci. USA* 97, 13401-10406). In other instances, interfering RNAs may bind to target RNA molecules having imperfect complementarity, causing translational repression without mRNA degradation.

The term "RNAi" or "RNA interference" refers to the process of sequence-specific post-transcriptional gene silencing (e.g., in nematodes), mediated by double-stranded RNA (dsRNA). "DsRNA" refers to RNA that is partially or completely double stranded. Double stranded RNA is also referred to as small interfering RNA (siRNA), small interfering nucleic acid (siNA), microRNA (miRNA), and the like. In the RNAi process, dsRNA comprising a first (antisense) strand that is complementary to a portion of a target gene and a second (sense) strand that is fully or partially complementary to the first antisense strand is introduced into an organism (e.g., plants and/or crops), by, e.g., transformation, injection, spray, brush or immersion, etc. After introduction into the organism, the target gene-specific dsRNA is processed into relatively small fragments (siRNAs) and can subsequently become distributed throughout the organism, leading to a loss-of-function mutation having a phenotype that, over the period of a generation, may come to closely resemble the phenotype arising from a complete or partial deletion of the target gene.

This approach takes advantage of the discovery that siRNA can trigger the degradation of mRNA corresponding to the siRNA sequence. RNAi is a remarkably efficient process whereby dsRNA induces the sequence-specific degradation of homologous mRNA in animals and plant cells (Hutvagner and Zamore (2002), Curr. Opin. Genet. Dev., 12, 225-232; Sharp (2001), Genes Dev., 15, 485-490).

The effects of RNAi can be both systemic and heritable in plants. In plants, RNAi is thought to propagate by the transfer of siRNAs between cells through plasmodesmata. The heritability comes from methylation of promoters targeted by RNAi; the new methylation pattern is copied in each new generation of the cell. A broad general distinction between plants and animals lies in the targeting of endogenously produced miRNAs; in plants, miRNAs are usually perfectly or nearly perfectly complementary to their target genes and induce direct mRNA cleavage by RISC, while animals' miRNAs tend to be more divergent in sequence and induce translational repression. Detailed methods for RNAi in plants are described in David Allis et al (Epigenetics, CSHL Press, 2007, ISBN 0879697245, 9780879697242), Sohail et al (Gene silencing by RNA interference: technology and application, CRC Press, 2005, ISBN 0849321417, 9780849321412), Engelke et al. (RAN Interference, Academic Press, 2005, ISBN 0121827976, 9780121827977), and Doran et al. (RNA Interference: Methods for Plants and Animals, CABI, 2009, ISBN 1845934105, 9781845934101), which are all herein incorporated by reference in their entireties for all purposes.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule.

DsRNA-mediated regulation of gene expression in plants is well known to those skilled in the art. See, e.g., WIPO Patent Application Nos. WO1999/061631A and WO1999/053050A, each of which is incorporated by reference herein in its entirety.

In some embodiments, an RNAi agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188).

In some embodiments the present invention also teaches expression vectors capable of producing inhibitor nucleic acid molecules. In some embodiments, the present invention teaches the use of RNA interference (RNAi) for the down-regulation of CiBAG6 genes, or homologs or orthologs of CiBAG6 genes. Thus in some embodiments the present invention teaches the expression of antisense, inverted repeat, small RNAs, artificial miRNA, or other RNAi triggering sequences.

In some embodiments the RNAi constructs of the present invention comprise sequences capable of triggering RNAi suppression of BAG6 genes, including nucleic acid fragments comprising sequence identities higher than about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% to a BAG6 gene target region, such as those disclosed in SEQ ID NO: 1 or SEQ ID NO: 8 or SEQ ID NO: 9 or SEQ ID NO. 10.

In some embodiments, the antisense or small RNA molecules are targeted to a section of the coding portion of the target gene. In other embodiments, the RNAi sequences of the present invention are targeted to the 5' or 3' untranslated regions (UTRs) of the target gene. In yet other embodiments, the RNAi sequences of the present invention are targeted to the promoter of the target gene. Methods of selecting sequence target regions for RNAi molecule design are described in more detail in (Fougerolles, et al., 2007; U.S. Pat. No. 7,732,593).

In some embodiments, the RNAi molecules of the invention may be modified at various locations, including the sugar moiety, the phosphodiester linkage, and/or the base. For example, in order to further increase the stability of the molecules in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety (U.S. Patent Publication 2011/251258).

In some embodiments, the present invention also teaches the down-regulation of genes via antisense technology. In some embodiments, the present invention can be practiced using other known methods for down-regulating gene expression including T-DNA knockout lines, tilling, TAL-mediated gene disruption, transcriptional gene silencing, and site-directed methylations.

Application of RNAi Formulation/Treatment

Plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are known in the art. See, e.g., U.S. Pat. No. 9,433,217, U.S. Patent Publication 2013/0047298, Chinese Patent No. 103748230B and Chinese Patent Publication CN101914540A, each of which is incorporated by reference herein in its entirety. Such methods and formulations represent a significant development for gene silencing technology using RNAi.

In some embodiments, the present invention teaches methods and formulations to topically apply exogenous RNA molecules to external tissue surfaces of plants. In some embodiments, the application exogenous RNA molecules, including dsRNA, siRNA, miRNA and aRNA, causes silencing of plant endogenous target genes or of the target genes of plant pests in the plant cells nearby the external tissue surfaces. In some embodiments, the application exogenous RNA molecules, including dsRNA, siRNA, miRNA and aRNA, causes silencing of plant endogenous target genes or of the target genes of plant pests in the plant cells that is located in a long distance from the external tissue surfaces.

In some embodiments, the present invention provides that applying dsRNA formulations (and/or treatments) by spray, brush, immersion of the dsRNA molecules, or other non-tissue invasive techniques, leads to absorption and assimilation of the exogenous RNA molecules into nearby or distant plant cells, thus causing endogenous and/or pest gene silencing. In some embodiments, pest genes are introduced into host plants by bacterial, fungal, or viral infection.

In some embodiments, the present invention teaches methods of repressing, preventing, eliminating, reducing, or otherwise ameliorating a bacterial or fungal infection of a plant comprising topical application of nucleic acid including DNA molecules as well as RNA molecules including dsRNA, siRNA, miRNA and aRNA Example 1: Identification of Citrus CiBAG6 Homolog and Demonstration of Single Identical Homologs in Carrizo, Hamlin and Valencia BLAST-P searches were performed using the predicted AtBAG6 protein sequence to identify a single citrus locus within the Clementine genome available online (http://www.phytozome.net/), referred to herein as CiBag6 (clementine0.9_012925m, coding region included in SEQ ID NO: 8). The DNA sequence of this locus, which is an AtBag6 homolog, was then used to determine how closely related it might be to other members of the Bag6 gene family in Clementine or Sweet Orange. Neither Clementine nor Sweet Orange varieties Hamlin or Valencia appeared to have any other sequences with high sequence similarity (>50%) over a stretch of more than 18 base pairs to AtBag6, other than a single CiBag6. This demonstrated not only that citrus did not carry multiple Bag6 homologs, but also that any region on CiBAG6 chosen as a probe or for silencing purposes would likely be specific to the target CiBag6 gene. Citrus mRNA was isolated from all three citrus varieties, and reverse transcriptase PCR (rtPCR) was performed using standard methods (Jiang, et al., 2012) to amplify a 930 bp exon fragment appropriate PCR primers. These DNA fragments were cloned into pGEM-T and three clones from each of the three citrus varieties were sequenced. The DNA sequences were 98% identical over the entire 930 bp stretch of CiBAG6 from Carrizo (SEQ ID NO: 1), and nearly 100% identical (1 bp difference between Carrizo and Hamlin or Valencia) over the first 200 bp of SEQ ID NO: 1.

Example 2: Antisense RNA (aRNA) Constructs with CaMV Promoter

The 828 bp region of Carrizo CiBAG6 (SEQ ID NO: 1) from the ATG start codon to the coding end of the fragment (position 103-930 of SEQ ID NO: 1) was cloned in the antisense direction into pIPG973 (WO 2013/032985 A1), which carries a single CaMV promoter. The CiBAG6 antisense fragment was then transcriptionally fused with 516 bp (in the sense orientation) from the uidA gene from pCAMBIA2301, forming pIPG1150 (see Table 2 and FIG. 1; SEQ ID NO: 2). This clone was used to transform Carrizo seedlings, resulting in multiple transformation events confirmed by PCR. Each transgenic event was numbered and expression of the CiBAG6 antisense construct was confirmed by rtPCR, using RNA extracted from each confirmed transgenic Carrizo event. Each confirmed expressing transgenic event was then evaluated to determine if CiBAG6 in Carrizo was actually silenced or not. DNA primers were designed based on the CiBAG6 transcript (cDNA) sequence, but outside of the regions cloned and used for silencing purposes. From FIG. 2, it may be seen that the control Carrizo exhibited relative CiBAG6 expression levels that were much higher than any of the silenced lines (labeled 1150-12, -34, -39, -40, -44 and -45). These results clearly demonstrated that the aRNA construct in pIPG1150 was effective in silencing CiBAG6.

To determine if the CiBAG6 silenced lines were affected in their response to a known PAMP elicitor (Shi, et al., 2013, 2014), levels of expression of each of the three defense response genes were examined by qPCR. PCR primers known to be useful in examining these responses in citrus were used (Pathogenesis Related 1 or PR1; Enhanced Disease Susceptibility 1 or EDS1, and Non race-specific Disease Resistance 1 or NDR1) (Shi, et al., 2014).

Figure 3:
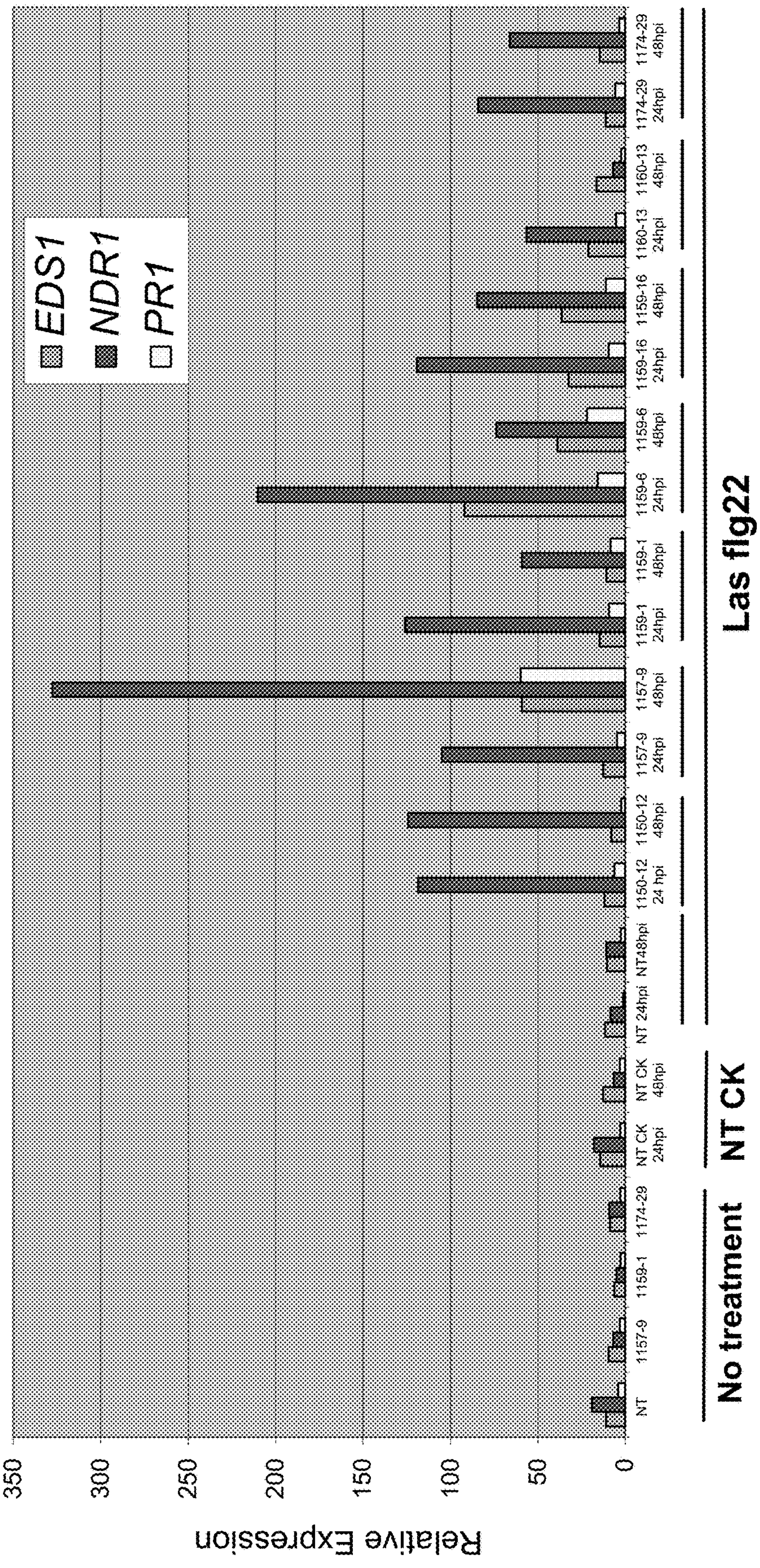
FIG. 3. Plant basal defense responses elicited by Las flagellin-22. To determine if several genes consistently associated with basal plant defense responses were affected by silencing CiBAG6, PCR primers known to be useful in examining three genes known to respond to PAMP elicitors in citrus were used (Pathogenesis Related 1 or PR1; Enhanced Disease Susceptibility 1 or EDS1, and Non race-specific Disease Resistance 1 or NDR1). Levels of expression of each of the three defense response genes in citrus were examined by qPCR. To elicit citrus plant defense responses, Las flagellin 22 (Las flg22) was used as a proxy for inoculation with Las. Defense responses in nontransgenic (NT) Carrizo inoculated with water (NT CK) was compared with NT Carrizo and CiBAG6 silenced Carrizo lines, all inoculated with Las flg22; again, qRT-PCR levels were normalized against the citrus gene, Elongation Factor 1 alpha. Controls also included determination of the levels of PR1, EDS1 and NDR1 in both NT Carrizo and CiBAG6 silenced lines that were not inoculated with Las flg22 as controls. Samples were taken at 24 hours post inoculation (24 hpi) and 48 hours post inoculation (48 hpi).

To elicit citrus plant defense responses, Las flagellin 22 (Las flg22) was used as an elicitor and proxy for inoculation with Las, using 10 μM of the Las flg22 elicitor dissolved in water (Shi, et al., 2013). Defense responses in nontransgenic (NT) Carrizo inoculated with water (NT CK) was compared with NT Carrizo and CiBAG6 silenced Carrizo lines, all inoculated with Las flg22. Controls also included determination of the levels of PR1, EDS1 and NDR1 in both NT Carrizo and CiBAG6 silenced lines that were not inoculated with Las flg22 as controls. From FIG. 3, the expression levels of NDR1 in line 1150-12 (silenced with pIPG1150) was particularly striking, since it was significantly higher both 24 and 48 hours after elicitation (>10× higher) than in NT controls. The increased expression of NDR-1 is significant since elevated levels of this gene are known to increase basal resistance to both bacteria and fungi in *Arabidopsis*, and is suggested to be likely to increase resistance to Las in citrus (Lu, et al., 2013). This result clearly demonstrated that silencing of CiBAG6 in Carrizo occurred, accompanied by increased expression of defense response genes, and would likely increase resistance in Carrizo to Las (source organism for flg22), and likely to additional biotrophic bacteria and fungi.

TABLE 2

| Summary of CiBAG6 silencing constructs used. | | |
|---|---|---|
| pIPG1150 | CaMV promoter; aRNA (no movement leader) | Example 2 |
| pIPG1157 | CaMV promoter; RNAi construct with 1848 bp GUS loop | Example 4 |
| pIPG1159 | AtSuc2 promoter; RNAi construct with 1848 bp GUS loop | Example 5 |
| pIPG1160 | AtSuc2 promoter with movement leader; aRNA | Example 3 |
| pIPG1174 | CaMV promoter; RNAi construct with 190 bp intron | Example 6 |

Example 3: Antisense RNA (aRNA) Constructs with AtSuc2 Promoter

Figure 2:
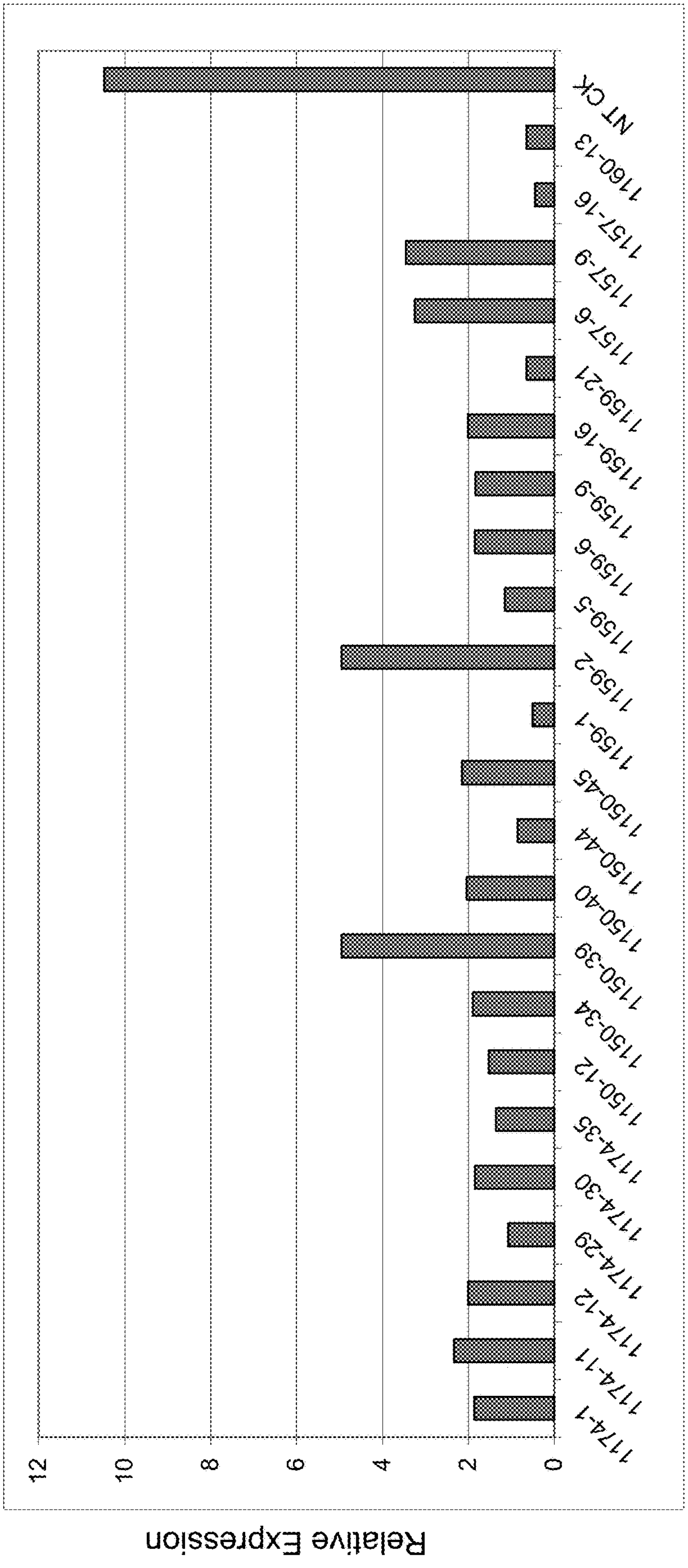
FIG. 2. CiBAG6 expression levels in different transgenic lines by qPCR. To determine if native CiBAG6 expression in the transgenic Carrizo lines was actually silenced by the various silencing constructs used, DNA primers were designed based on the CiBAG6 sequence, but outside of the regions cloned and used for silencing purposes. cDNAs made from RNA extracts that were treated with DNase taken from each transformed plant line were used. qRT-PCR levels were normalized against the citrus gene, Elongation Factor 1 alpha. NT CK is nontransgenic check (i.e., control).

As in Example 2, the 828 bp region of Carrizo CiBAG6 (SEQ ID NO: 1) from the ATG start codon to the coding end of the fragment (position 103-930 of SEQ ID NO: 1) was cloned in the antisense direction into pIPG980 (WO 2013/032985 A1), which carries a single CaMV promoter, forming pIPG1160 (see Table 2 and FIG. 1; SEQ ID NO: 3). A potential movement leader sequence from *Arabidopsis thaliana*, flowering locus T (FT) from nucleotide position 326 to nucleotide 429 in GenBank: GQ395494.1 (SEQ ID NO: 7) was transcriptionally fused in the sense orientation at the 5' end of the aRNA construct utilized in construction of pIPG1160 (FIG. 1).

As provided in Example 2, each transgenic event was confirmed by PCR and expression of the CiBAG6 antisense construct was confirmed by rtPCR, using RNA extracted from each confirmed transgenic Carrizo event. Each confirmed expressing transgenic event was then evaluated to determine if CiBAG6 in Carrizo was actually silenced or not. From FIG. 2, it may be seen that the control Carrizo exhibited relative CiBAG6 expression levels that were much higher than 1160-13, again clearly demonstrated that the pIPG1160 construct, this time using the AtSuc2 promoter and providing a potential long distance transport leader, was effective in silencing CiBAG6.

Again to determine if the CiBAG6 silenced lines were affected in their response to the known PAMP elicitor Las flg22, levels of expression of each of the three defense response genes PR1, EDS1 and NDR1 were examined by qPCR as in Example 2. From FIG. 3, the expression levels of NDR1 in line 1160-13 (silenced with pIPG1160) was significantly higher (5× higher) 24 hours after elicitation than in NT controls. Expression levels of EDS1 were 1.7× higher 24 hours after elicitation than in NT controls. By 48 hours, the effects from silencing due to this construct were not significantly different from the controls. Overall, the effects on silencing of CiBAG6 by this construct were less than the effects observed using pIPG1150, and likely was due to the expected reduced promoter strength and tissue specificity of the AtSuc2 promoter used to construct pIPG1160, compared to the CaMV promoter used to construct pIPG1150 (Table 2). This result clearly demonstrated that silencing of CiBAG6 in Carrizo occurred, accompanied by increased expression of defense response genes, and would likely increase resistance in Carrizo at least to Las (source organism for flg22), and likely to additional biotrophic bacteria and fungi. This result also indicated that the AtSuc2 promoter might be useful in preventing unintended consequences of too much silencing of CiBAG6 or overly generalized silencing of CiBAG6.

Example 4: RNAi Constructs with CaMV Promoter and GUS Loop

For silencing purposes, a region of 200 bp in length was selected from the first exon, based on a high level of sequence identity (nearly 100% as explained in Example 1) among the three CiBAG6 cDNA clones obtained from citrus rootstock cultivar Carrizo citrange (*Citrus sinensis* L. Osbeck x *Poncirus trifoliata* L. Raf.), and from sweet orange cultivars (*Citrus sinensis*) Hamlin and Valencia. Homology with Hamlin and Valencia was important in order to be able to graft transmit the silencing RNA used to nontransgenic Hamlin and Valencia scions (to be grafted later after regeneration of transgenic Carrizo rootstock), with the expectation that silencing would occur in the grafted scion.

The first 200 bp of Carrizo CiBAG6 (SEQ ID NO: 1) was cloned in sense orientation into pIPG980 (WO 2013/032985 A1), which carries a single CaMV promoter, followed by a 1,848 bp fragment from the uidA gene that forms a GUS loop, followed by the same 200 bp CiBAG6 sequence, but in an antisense orientation, forming pIPG1157 (see Table 2 and FIG. 1; SEQ ID NO: 4). Upon expression, each mRNA formed from pIPG1157 will anneal to form a stem-loop structure. This clone was used to transform Carrizo seedlings, resulting in multiple transformation events confirmed by PCR.

As provided in Example 2, expression of each transgenic event was confirmed by rtPCR, using RNA extracted from each confirmed transgenic Carrizo event. Each confirmed expressing transgenic event was then evaluated to determine if CiBAG6 in Carrizo was actually silenced or not. From FIG. 2, it may be seen that the control Carrizo exhibited relative CiBAG6 expression levels that were much higher than the three 1157 transgenic events examined (1157-6, 1157-9 and 1157-16), again clearly demonstrated that the pIPG1157 construct, this time using RNAi rather than aRNA for silencing, was effective in silencing CiBAG6.

Again, to determine if the CiBAG6 silenced lines were affected in their response to the known PAMP elicitor Las flg22, levels of expression of each of the three defense response genes PR1, EDS1 and NDR1 were examined by qPCR as in Examples 2 and 3. From FIG. 3, the expression levels of NDR1 in line 1157-9 (silenced with pIPG1157) was particularly striking, since it was significantly higher at 24 hours after elicitation (9.6× higher) and by 48 hours had climbed to 30× higher after elicitation than in NT controls. Both EDS1 and PR1 had climbed to 4.8× and 25× higher, respectively, than NT controls elicited with the same amount of Las flg22. Again, the increased expression of NDR-1 is significant since elevated levels of this gene are known to increase basal resistance to both bacteria and fungi in *Arabidopsis*, and is suggested to be likely to increase resistance to Las in citrus (Lu, et al., 2013). This result clearly demonstrated that silencing of CiBAG6 in Carrizo occurred using an RNAi construct driven by the same promoter as used the aRNA construct in Example 2 (pIPG1150), but accompanied by even greater increased expression of defense response genes than seen using aRNA, and would likely strongly increase resistance in Carrizo to Las (source organism for flg22), and likely to additional biotrophic bacteria and fungi.

Example 5: RNAi Constructs with AtSuc2 Promoter and GUS Loop

A construct identical to that used in Example 4 was created, except that a single AtSuc2 promoter was substituted for the single CaMV promoter of pIPG1157, to form pIPG1159 (see Table 2 and FIG. 1; SEQ ID NO: 5). This clone was used to transform Carrizo seedlings, resulting in multiple transformation events confirmed by PCR.

As provided in Example 2, expression of each transgenic event was confirmed by rtPCR, using RNA extracted from each confirmed transgenic Carrizo event. Each confirmed expressing transgenic event was then evaluated to determine if CiBAG6 in Carrizo was actually silenced or not. From FIG. 2, it may be seen that the control Carrizo exhibited relative CiBAG6 expression levels that were much higher than the seven 1159 transgenic events examined (1159-1, 1159-2, 1159-5. 1159-6, 1159-9, 1159-16 and 1159-21), again clearly demonstrated that the pIPG1159 construct, again using RNAi rather than aRNA for silencing, but RNAi gene expression driven by the AtSuc2 promoter, was effective in silencing CiBAG6.

Again, to determine if the CiBAG6 silenced lines were affected in their response to the known PAMP elicitor Las flg22, levels of expression of each of the three defense response genes PR1, EDS1 and NDR1 were examined by qPCR as in Examples 2, 3 and 4. From FIG. 3, the expression levels of NDR1 in line 1159-6 (silenced with pIPG1159) was particularly striking, since it was significantly higher than controls at 24 hours after elicitation (19× higher), but as with the aRNA construct operationally driven by the AtSuc2 promoter in Example 3 (pIPG 1160-13), by 48 hours the effect was greatly reduced (to 7× higher expression of NDR-1), but still significantly different from all controls. Unlike the antisense construct, however, expression levels of both EDS1 and PR1 of the 1159-6 line was 7.6× and 6.6× higher, respectively, than NT controls at 24 hours after elicitation by Las flg22. This result clearly demonstrated that silencing of CiBAG6 in Carrizo occurred using an RNAi construct driven by the same promoter as used the aRNA construct in Example 3 (pIPG1160), but accompanied by even greater increased expression of defense response genes than seen using aRNA, and would likely strongly increase resistance in Carrizo to Las (source organism for flg22), and likely to additional biotrophic bacteria and fungi. As with Example 3 (pIPG1160) the effect on expression of elicited defense response genes was stronger at 24 hours than 48 hours after elicitation, indicating that the AtSuc2 promoter may provide a better regulated response.

Example 6: RNAi Constructs with 35S Promoter and Intron Loop

The use of introns has shown to be more effective than random stretches of DNA loops in the creation of RNAi constructs (Stoutjesdijk, et al., 2002). Therefore the 190 bp catalase intron was PCR amplified from pIPG973 and used to replace the GUS fragment 2 loop used in pIPG1157 to form pIPG1174 (see Table 2 and FIG. 1; SEQ ID NO: 6). This clone was used to transform Carrizo seedlings, resulting in multiple transformation events confirmed by PCR.

As provided in Example 2, expression of each transgenic event was confirmed by rtPCR, using RNA extracted from each confirmed transgenic Carrizo event. Each confirmed expressing transgenic event was then evaluated to determine if CiBAG6 in Carrizo was actually silenced or not. From FIG. 2, it may be seen that the control Carrizo exhibited relative CiBAG6 expression levels that were much higher than the six 1174 transgenic events examined (1174-1, 1174-11, 1174-12, 1174-29, 1174-30 and 1174-35), again clearly demonstrating that the pIPG1174 construct, again using RNAi rather than aRNA for silencing, but the catalase intron as a loop, was effective in silencing CiBAG6.

Again, to determine if the CiBAG6 silenced lines were affected in their response to the known PAMP elicitor Las flg22, levels of expression of each of the three defense response genes PR1, EDS1 and NDR1 were examined by qPCR as in Examples 2, 3, 4 and 5. From FIG. 3, the expression levels of NDR1 in line 1174-29 (silenced with pIPG1174) was significantly higher than controls at both 24 and 48 hours after elicitation (6-7.7× higher). Consistent with the other silencing lines driven by the CaMV promoter, the effect is almost as pronounced at 48 hours as at 24 hours after elicitation by Las flg22. This result clearly demonstrated that silencing of CiBAG6 in Carrizo occurred using an RNAi construct driven by the same promoter as used in the RNAi construct in Example 4 (pIPG1157).

Example 7: Movement of Both RNAi and aRNA from Transgenic Rootstock to Nontransgenic Citrus Scion Thirty-two nontransgenic mature Hamlin (sweet orange) citrus scions were grafted onto silenced, transformed Carrizo rootstock lines expressing pIPG1150, pIPG1159, pIPG1160 or pIPG1174. Four grafted plants representing each of the four different silencing constructs were tested in these assays. The quality of the RNA extracted from each line was verified by PCR to ensure uniformity. Using two of the constructs (pIPG1150, an aRNA construct, and pIPG1159 an RNAi construct), the silencing signal failed to move. One aRNA construct that failed to move, pIPG1150, was engineered to move moderately well in construct pIPG1160 with addition of the movement leader (SEQ ID NO. 7). One RNAi construct (expressed from IPG1174) moved very efficiently into nontransgenic Hamlin sweet orange scions.

Example 8: CiBAG6-Silenced Lines were Highly Resistant to Las and Conferred this Resistance Long Distance to Nontransgenic Scions Heavily Infected with Las Las infected citrus (both *C. sinensis* sweet orange and *C. paradisi* grapefruit) exhibiting symptoms of HLB and also tested by real time PCR and showing strong positive PCR signals for Las bacterial infection were approach grafted to non-infected transgenic CiBAG6-silenced lines. After several months, many of the transgenic CiBAG6 silenced lines became PCR positive, indicating Las bacterial infection through the graft union. After exhibiting at least two positive PCR tests over a period of two months, such CiBAG6-silenced lines were considered to be infected by Las and the graft union from the infected source tree was severed. In most cases where the transgenic Carrizo became infected, the Las-infected scion remained intact from the approach graft union, leaving the infected scion attached to an infected but CiBAG6 silenced Carrizo rootstock.

In many cases, the CiBAG6 silenced lines never became infected, while the nontransgenic, infected scion remained infected and still attached to its infected rootstock through the approach graft union. After six months, the infected nontransgenic tree was severed from the transgenic Carrizo rootstock, again leaving the infected nontransgenic scion still attached to a noninfected but CiBAG6 silenced Carrizo rootstock.

After at least one full year of challenge inoculation, 4 out of 4 transgenic Carrizo rootstocks transformed with pIPG1150, 2 out of 3 transgenic Carrizo rootstocks transformed with pIPG1157, 2 out of 4 transgenic Carrizo rootstocks transformed with pIPG1159, and 5 out of 5 transgenic Carrizo rootstocks transformed with pIPG1160 were either cured of Las or had failed to become infected by Las. In the cases of pIPG1150 and pIPG1160, the attached, previously infected, nontransgenic scions had become cured of Las. These results clearly demonstrated that silencing of CiBAG6 in a rootstock conferred immunity from, or strong resistance to, infection by Las, depending upon the level of efficiency of the silencing. Furthermore, these results demonstrated long distance movement of the silencing signal from the transgenic rootstock, across a graft union, to provide immunity or strong resistance to nontransgenic citrus, to the level of curing of Las. Again, this curing appeared to depend upon the efficiency of the asRNA or siRNA construct in suppressing CiBAG6. Finally, these results are consistent with reports that the efficiency of RNAi increases with the length of the clones (asRNA or siRNA) used to create the dsRNA for RNAi purposes.

Example 9: Challenge Inoculations with Las of CiBAG6-Silenced Rootstock with Grafted Non-Transgenic Hamlin or Valencia Mature Scions Grafted mature, nontransgenic Hamlin shoots from Example 7 that were micrografted onto transgenic Carrizo lines and demonstrated to exhibit mobile silencing will be challenge inoculated with Las as in Example 8.

Example 10. Silenced CiBAG6 Lines Exhibit Both Heat and Cold Tolerance

Two different transgenic lines (1150-53 and 1174-57) and two nontransgenic lines (NT) were put under high constant temperature stress (42° C. for 6 days); these levels of heat treatment are effective in curing citrus of HLB. Although all plants survived these treatments, the control plants were clearly damaged, partially defoliated and recovered slowly, while the two silenced Carrizo lines exhibited almost no damage or defoliation and needed no recovery period. Cold tolerance was also tested with two lines (−1° C.) for 5 days. Both the control and silenced plants exhibited cold damage (wilted leaves) from the treatment. After 7 days of recovery, the silenced line clearly had recovered fully with little leaf loss, while the control plant was nearly completely defoliated. Suppression of the target apoptotic regulatory gene CiBAG6 appears to strongly enhance the citrus plant's resistance to abiotic stress, and may provide citrus growers with a means to protect newly planted trees from frost damage.

Example 11. CiBAG6 Expression was Suppressed in Nontransgenic Citrus Leaves after Treating the Roots with an Aqueous Solution of CiBAG6 dsRNA or siRNA within 48 Hours of Such Treatment In order to determine if exogenously supplied dsRNA or siRNA could be applied directly to citrus trees in order to silence CiBAG6 and avoid the use of transgenic rootstocks to achieve the desired effects, citrus rootstock Carrizo seedlings were germinated and grown hydroponically, the roots rinsed and immersed in a water solution containing either 224 μg of long dsRNA (800 nt in length) or 19.6 μg of siRNA (ca. 23 nt in length). The dsRNA used was PCR amplified from Carrizo citrange using primers designed from positions 637-1434 of SEQ ID NO. 10) and transcribed in vitro. The siRNA used was formed after digestion of the 800 nt Carrizo dsRNA product with RNAseIII from New England Biolabs.

Figure 4:
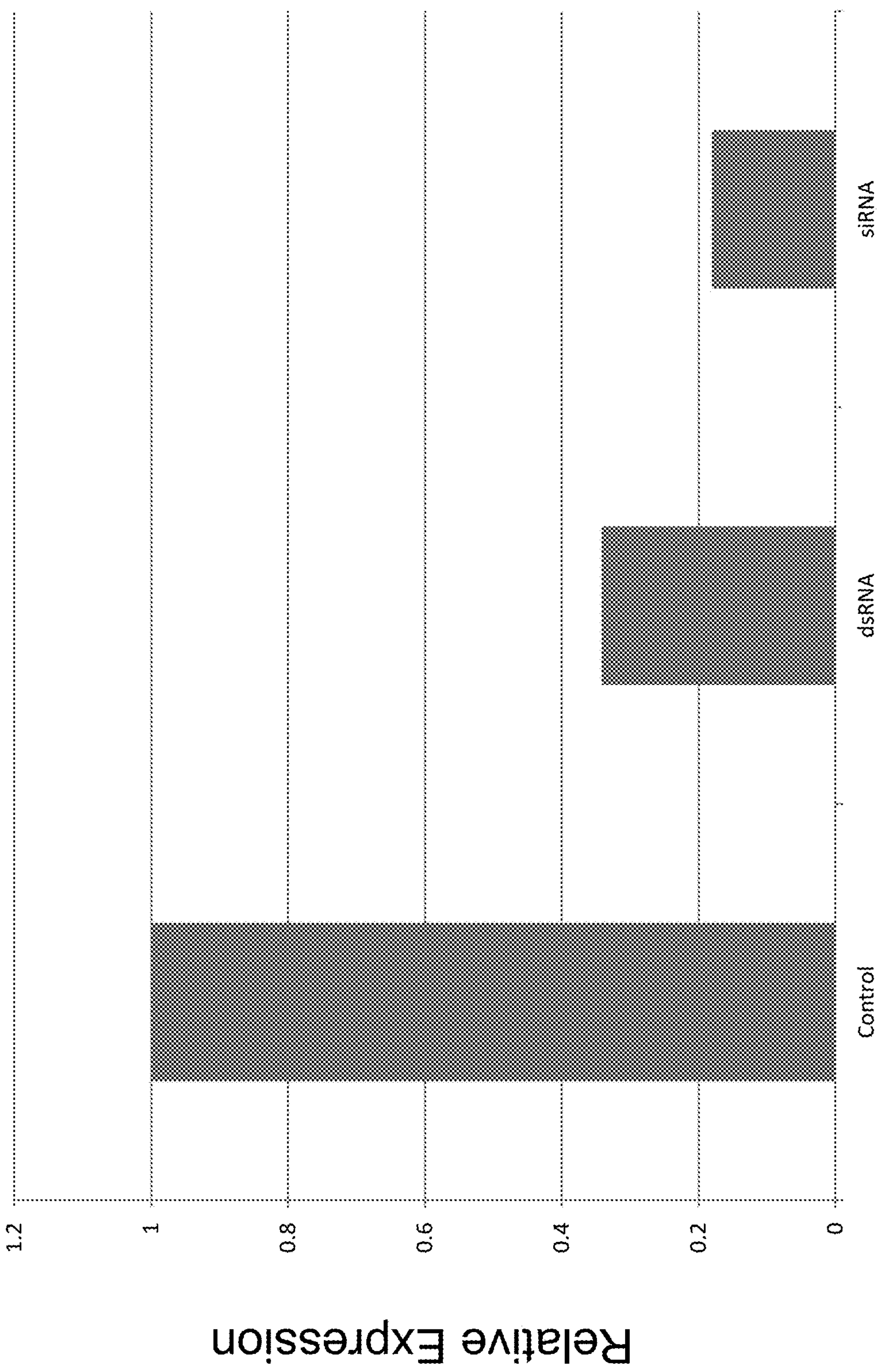
FIG. 4. CiBAG6 expression is suppressed in citrus leaves after root treatment using either long dsRNA or siRNA. Citrus rootstock Carrizo seedlings treated with root immersion into a solution with either dsRNA (800 nucleotides in length) or siRNA (average of 23 nucleotides in length) exhibited long distance silencing of ciBAG6 (in untreated leaves) within 48 hours. PCR (qRT-PCR) was used to determine levels of expression of CiBAG6 in all leaf samples, using primers well outside of the region of CiBAG6 used for the RNA treatments. qRT-PCR levels were normalized against the control mRNA expression level.

Care was taken to protect the leaves from exposure to the dsRNA and siRNA root treatments. RNA was extracted from the leaves of the treated plants 48 hrs after treatment of the roots. Real time quantitative reverse transcription PCR (qRT-PCR) was used to determine levels of expression of CiBAG6 in all samples, using primers well outside of the region of CiBAG6 used for the RNA treatments. qRT-PCR levels were normalized against the control reaction (set at 100%), and relative expression levels of CiBAG6 in both treatments determined. As documented in FIG. 4, both dsRNA and RNAi moved long distances from the roots to the shoots and into the leaves within 48 hrs, as evidenced by the suppression of expression of CiBAG6 in the leaves.

Example 12. CiBAG6 Expression was Suppressed in Nontransgenic Citrus Leaves after Spraying the Leaves with an Aqueous Solution of CiBAG6 dsRNA or siRNA In order to determine if exogenously supplied dsRNA or siRNA could be applied directly to citrus trees by spray treatment in order to silence CiBAG6 and avoid the use of root drench or transgenic rootstocks to achieve the desired effects, citrus rootstock Carrizo seedlings were germinated and grown hydroponically. Citrus leaves sprayed with an aqueous solution containing either 16 μg of long dsRNA (800 nt in length) or 1.4 μg of siRNA (ca. 23 nt in length), made as described in Example 11.

Figure 5:
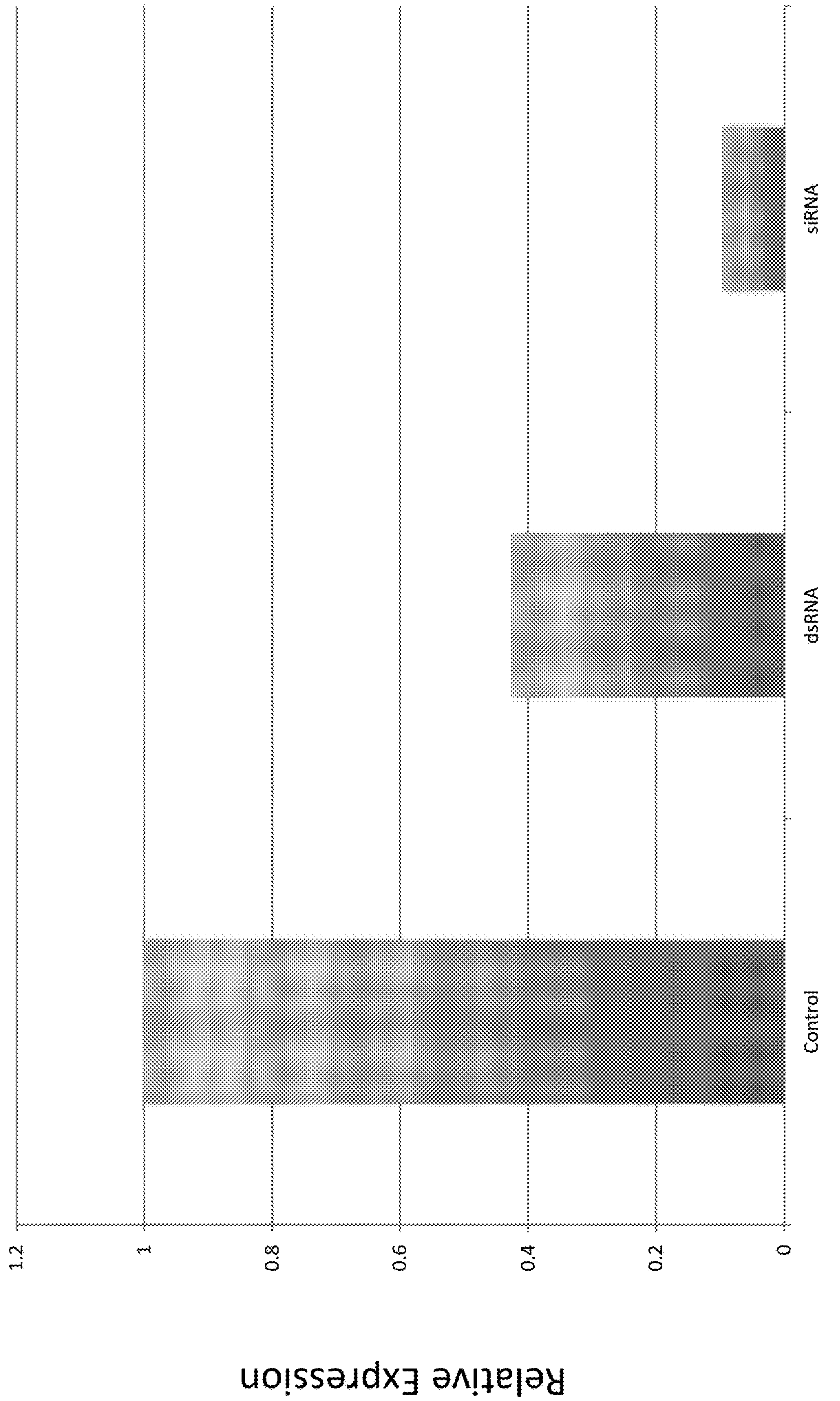
FIG. 5. CiBAG6 expression is suppressed in citrus leaves after spray treatment using either long dsRNA or siRNA. Citrus rootstock Carrizo seedlings sprayed with either 16 μg of long dsRNA or 1.4 μg of siRNA RNA was extracted from the leaves of the treated plants 80 hrs after spraying the leaves, and qRT-PCR used to determine levels of expression of CiBAG6 in all leaf samples, using primers well outside of the region of CiBAG6 used for the RNA treatments. qRT-PCR levels were normalized against the control mRNA expression level.

The spray concentration used was 2.8 μg/ml siRNA and 32 μg/ml dsRNA; plant weight range was 0.5 to 0.9 grams, so the amount applied was in the range of 2-20 μg/g plant tissue. RNA was extracted from the leaves of the treated plants 80 hrs after treatment of the leaves, and qRT-PCR used to determine levels of expression of CiBAG6 in all samples as described in Example 11. Clearly, from FIG. 5 it may be seen that both dsRNA and RNAi sequences from effectively suppressed expression of CiBAG6, and using levels of dsRNA and siRNA 20× less than those used for the root treatments.

Example 13. Treatment Using Either Long dsRNA or siRNA of CiBAG6 Results in Killing of Ca. *Liberibacter asiaticus* (Las) Cells An RNA-based, live cell assay was performed in a field trial using commercially grown citrus. Four year old grapefruit trees planted in a commercial grove that was 100% infected (all trees in the grapefruit block were infected) with Las were used for the field trial. Selected trees were injected with an aqueous formulation containing either 720 μg of long dsRNA (800 nt in length) or 112.5 μg of siRNA (ca. 23 nt in length) made as described in Example 11.

Plant weight of these field grown trees was estimated to average 26 kg, and therefore the amount injected was in the range of 4.3 to 28 mg/kg plant tissue. Control plants were mock-injected with the aqueous carrier solution. Both DNA and RNA were extracted from leaf samples taken from the field, one month after treatments were applied. Not surprisingly, negative but small effect was noted on the apparent titer of Las as determined by DNA based qRT-PCR reactions one month after treatment. It is well understood that bacterial DNA, including DNA from dead bacteria killed by a treatment, is highly persistent in plants, and that since RNA degrades more rapidly after cell death, is a much more sensitive real time indicator of anti-bacterial therapies (Fittipaldi et al, 2012). Therefore, RNA based assays have been recently adapted for evaluation of treatments designed to cure Las infections of citrus (Gardner et al. 2016). To this end, an RNA based live cell assay for Las was utilized for initial evaluation of these field trials, using methodology similar to that described in Example 11, except that expression of the Las bacterial gene, SC2_gp095 peroxidase was compared to the standard plant housekeeping gene cox1.

Figure 6:
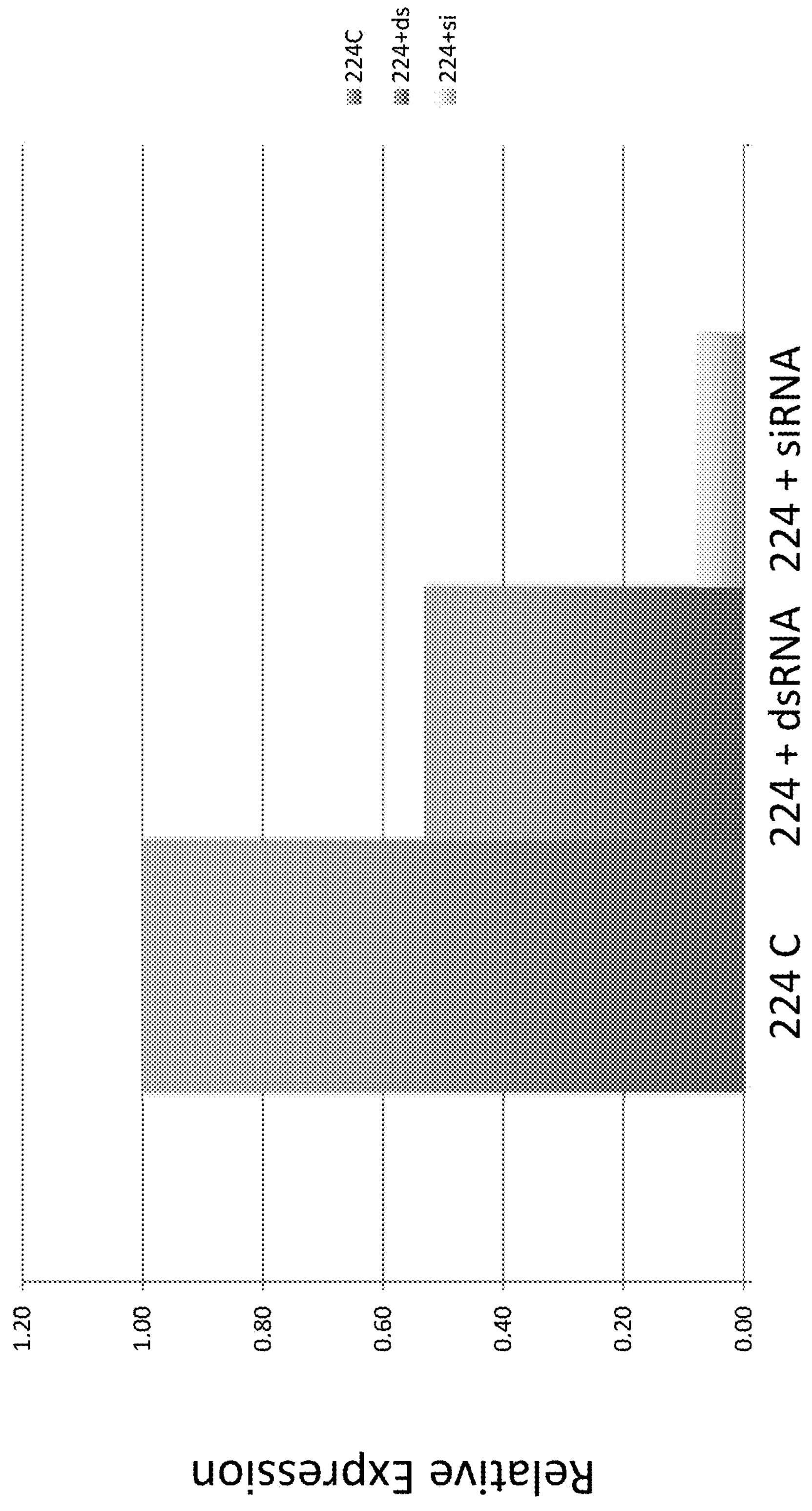
FIG. 6. Ca. *Liberibacter asiaticus* (Las) infection is reduced in commercially grown citrus after injection treatment using either long dsRNA or siRNA. An RNA-based, live cell assay was performed in four year old, commercially grown grapefruit trees in a field trial that were 100% infected with Las. Selected trees were injected with an aqueous formulation, 224, containing either long dsRNA or siRNA. Control plants were mock-injected with the aqueous formulation 224 without dsRNA or siRNA. qRT-PCR was used as in FIG. 4 to determine levels of expression of Las SC2_gp095 peroxidase. Plant cox1 was used to normalize expression SC2 peroxidase gene expression is an indicator of live Las cells, and was clearly suppressed after a single treatment application of dsRNA or siRNA in formula 224, one-month post treatment.

The effects of CiBAG6 siRNA and dsRNA treatments of grapefruit trees on the transcriptional activity of Las prophage encoded locus SC2_gp095 peroxidase was determined. Plant cox1 was used to normalize expression As clearly observed in FIG. 6, SC2 peroxidase gene expression, an indicator of living Las cells, was suppressed after single trunk injection treatment of commercially grown, Las-infected grapefruit trees (4 years old) in a field trial using dsRNA or siRNA in formula 224, within one month post treatment. This result demonstrated that such treatments killed Las cells in commercially grown citrus trees in the field and confirmed the data provided in Example 8.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

All publications, patents, patent publications, and nucleic acid and amino acid sequences cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

CITED REFERENCES

Brunings, A. M. and Gabriel, D. W. 2003. *Xanthomonas citri*: breaking the surface. Molecular Plant Pathology 4:141-157.

Chibucos, M. C., C. W. Collmer, T. Torto-Alalibo, M. Gwinn-Giglio, M., Lindeberg, D. Li, and B. M. Tyler. 2009. Programmed cell death in host symbiont associations, viewed through the Gene Ontology. BMC Microbiol. 9 (Suppl. 1): 55.29.

Deng, J.-X., Nie, X.-J., Lei, Y.-F., Ma, C.-F., Xu, D.-L., Li, B. and Zhang, G.-C. 2012. The highly conserved 5' untranslated region as an effective target towards the inhibition of Enterovirus 71 replication by unmodified and appropriate 2'-modified siRNAs. *Journal of Biomedical Science,* 19(1), 73. http://doi.org/10.1186/1423-0127-19-73

Dickman, M. B., Park, Y. K., Oltersdorf‡, T., Li, W., Clemente, T., French, R. 2001. Abrogation of disease development in plants expressing animal antiapoptotic genes. Proc. Natl. Acad. Sci. USA 98: 6957-6962.

Doukhanina, E. V., S. Chen, E. van der Zalm, A. Godzik, J. Reed, and M. B. Dickman. 2006. Identification and functional characterization of the BAG protein family in *Arabidopsis thaliana*. Journal of Biological Chemistry 281:18793-18801

Fittipaldi, M., Nocker, A., Codony, F., 2012. Progress in understanding preferential detection of live cells using viability dyes in combination with DNA amplification. J. Microbiol. Methods. 91 (2), 276-289.

Gardner, C. L., Pagliai, F. A., Pan, L., Bojilova, L., Torino, M. I., Lorca, G. L., & Gonzalez, C. F. (2016). Drug Repurposing: Tolfenamic Acid Inactivates PrbP, a Transcriptional Accessory Protein in *Liberibacter asiaticus. Frontiers in Microbiology,* 7, 1630. http://doi.org/10.3389/fmicb.2016.01630.

Gilchrist, D. and Lincoln, J. 2011. Pierce's Disease control and bacterial population dynamics in winegrape varieties grafted to rootstocks expressing anti-apoptotic sequences. Proceedings of the 2011 Pierce's Disease Research Symposium, Sacramento, pp 118-121.

Jiang, Y., Ding, X., Chen, X., Wang, Y., Song, W. 2013. The rice XA21 binding protein 25 encodes an ankyrin repeat containing protein and is required for full Xa21-mediated disease resistance. Plant J. 73: 814-823.

Kasai A, Bai S, Li T, Harada T (2011) Graft-Transmitted siRNA Signal from the Root Induces Visual Manifestation of Endogenous Post-Transcriptional Gene Silencing in the Scion. PLoS ONE 6(2): e16895.

Lai C F, Chen C Y & Au L C (2013): Comparison between the repression potency of siRNA targeting the coding region and the 3'-untranslated region of mRNA. Biomed Res Int 2013: 637850.

Li Z T, Dhekney S A, Gray D J. 2011. PR-1 gene family of grapevine: a uniquely duplicated PR-1 gene from a *Vitis* interspecific hybrid confers high-level resistance to bacterial disease in transgenic tobacco. Plant Cell Rep. 30: 1-11.

Lacomme, C. and S. S. Cruz. 1999. Bax-induced cell death in tobacco is similar to the hypersensitive response. *Proceedings of the National Academy of Sciences of the United States of America* 96, no. 14:7956-7961.

Lopes, S. A., Bertolini, E., Frare, G. F., Martins, E. C., Wulff, N. A., Teixeira, D. C., Fernandes, N. G., and Cambra, M. 2009. Graft transmission efficiencies and multiplication of '*Candidatus Liberibacter americanus*' and 'Ca. *Liberibacter asiaticus*' in citrus plants. Phytopathology 99:301-306

Lu, H., Zhang, C., Albrecht, U., Shimizu, R., Wang, G., Bowman, K. D. 2013. Overexpression of a citrus NDR1 ortholog increases disease resistance in *Arabidopsis*. Front. Plant Sci. 4: Article 157: 1-10.

Melnyk, C W., Molnar, A. and D. C. Baulcombe 2011. Intercellular and systemic movement of RNA silencing signals. The EMBO Journal 30: 3553-3563.

Portt, L., Norman, G., Clapp, C., Greenwood, M., and Greenwood, M. T. Anti-apoptosis and cell survival: A review. Biochimica et Biophysica Acta 1813: 238-259.

Reynolds, A., D. Leake, Q. Boese, S. Scaringe, W. S. Marshall, and A. Khvorova. 2004. Rational siRNA design for RNA interference. *Nature Biotechnology* 22:326-330.

Sarowar, S., Y. J. Kim, E. N. Kim, K. D. Kim, B. K. Hwang, R. Islam, and J. S. Shin. 2005. Overexpression of a pepper basic pathogenesis-related protein 1 gene in tobacco plants enhances resistance to heavy metal and pathogen stresses. *Plant Cell Reports* 24, no. 4:216-224.

Shi, Q., Febres, V. J., Jones, J. B., Moore, G. A. 2014. Responsiveness of different citrus genotypes to the *Xanthomonas citri* ssp.*citri*-derived pathogen-associated molecular pattern (PAMP) flg22 correlates with resistance to citrus canker. Molecular Plant Pathology. Article first published online; DOI: 10.1111/mpp.12206.

Shi, Q., Febres, V. J., Jones, J. B., Moore, G. A. 2013. Flg22 derived from *Xanthomonas citri* subsp. *citri* and *Candidatus Liberibacter asiaticus*' trigger similar defense responses in mandarin and grapefruit. Phytopathology. 103(Suppl. 2): 52.132.

Stoutjesdijk PA1, Singh S P, Liu Q, Hurlstone C J, Waterhouse P A, Green A G. 2002. hpRNA-mediated targeting of the *Arabidopsis* FAD2 gene gives highly efficient and stable silencing. Plant Physiol. 129:1723-31.

Takayama, S., Sato, T., Krajewski, S., Kochel, K., Irie, S., Millan, J. A., and Reed, J. C. 1995. Cloning and functional analysis of BAG-1, a novel BCL-2 binding protein with anti-cell death activity. Cell 80, 279-284).

Van Loon L, Rep M, Pieterse C. 2006. Significance of inducible defense-related proteins in infected plants. Annu. Rev. Phytopathol. 44: 135-162.

Watanabe N, Lam E (2008) BAX inhibitor-1 modulates endoplasmic reticulum stress mediated programmed cell death in *Arabidopsis*. J Biol Chem 283:3200-3210.

Williams, B., Kabbage, M., Britt, R., and Dickman, M. B. 2010. AtBAG7, an *Arabidopsis* Bch 2-associated athano gene, resides in the endoplasmic reticulum and is involved in the unfolded protein response. *Proc. Natl. Acad. Sci. USA* 107:6088-6093.

Xu, P., Rogers, S. J., Roossinck, M. J., 2004. Expression of antiapoptotic genes bcl-xL and ced-9 in tomato enhances tolerance to viral-induced necrosis and abiotic stress. *Proc. Natl. Acad. Sci. USA* 101:15805-15810.

Zhang, S., Flores-Cruz, Z., Zhou, L., Kang, B. H., Fleites, L., Gooch, M. D., Wulff, N. A., Davis, M. J., Duan, Y., and Gabriel, D. W. 2011. Ca. *Liberibacter asiaticus* carries an excision plasmid prophage and a chromosomally integrated prophage that becomes lytic in plant infections. Molec. Plant-Microbe Interactions 24:458-468.

The invention claimed is:

1. A method of repressing, preventing, or otherwise reducing bacterial and/or fungal infections of a citrus plant comprising applying to the citrus plant an isolated nucleic acid sequence comprising the entire or a partial nucleic acid sequence of a Bcl-2-associated Athanogene 6 (BAG6) gene, wherein said application represses, prevents, silences, or otherwise reduces expression of an endogenous BAG6 gene, and wherein said application represses, prevents, or otherwise reduces said bacterial and/or fungal infections caused by a biotrophic plant pathogen in the citrus plant.

2. The method of claim 1, wherein the application comprises treating the plant with an aqueous solution comprising the isolated nucleic acid.

3. The method of claim 1, wherein the application comprises treating roots of the plant.

4. The method of claim 1, wherein the application comprises treating leaves of the plant.

5. The method of claim 1, wherein the application comprises injecting and/or spraying the isolated nucleic acid sequences into or onto the plant.

6. The method of claim 1, wherein the entire isolated nucleic acid sequence is at least about 97% identical to the nucleic acid sequence set forth in SEQ ID NO: 10.

7. The method of claim 1, wherein the partial isolated nucleic acid sequence is at least 97% identical to a nucleic acid sequence of at least 21 contiguous base pairs from the nucleic acid sequence set forth in SEQ ID NO: 10.

8. The method of claim 1, wherein the biotrophic plant pathogen is a *Liberibacter.*

9. The method of claim 8, wherein the *Liberibacter* is *Liberibacter asiaticus* (Las).

* * * * *

SEQUENCE LISTING

```
<160> NUMBER OF SEQ ID NOS: 13

<210> SEQ ID NO 1
<211> LENGTH: 930
<212> TYPE: DNA
<213> ORGANISM: Carrizo citrange

<400> SEQUENCE: 1

ttctggatgc cttctaacag tgagcagagg gagcctgaaa agaaggccca aaggcaaggg      60

aaatgctggt tgtcactaga tacaaacagc cctaaacttt ttatgcatgg tgaagatgat     120

aaagaaaaag tgaaccaaca atttccgtac ccctttttt ggatgccttt tcaaactgag     180

gaaggggagg ttgaaaagaa agatcgaaag gagaagaatg ttgcttcaat atcagccgaa     240

gaatcacctt ctgattctaa gtttatgcag gtgaagcctc cagagagtga tgaaaggatg     300

aaaaattttg agccaaacga cgatttttct gataataagg ctaaaagctc acaactgatg     360

gagggcactg ctaataaaaa aattattcct gtaaggcaag tggaaatgtg cagggaggac     420

cactctgaca gtgctgagaa tggagttgca gcagataatt cctccagaac cagtaagatg     480

agacagtcct catctccacc gaagacaaca aaattacctc ctgtttgtct gagactggaa     540

cctttgtcaa agaagaaaaa tggtaatggg aattccagat cccctagtcc tccaggcctg     600

aaaagacaga cagacgaata cgttcacaag ccttctgctt catcagtatt gaaagagagc     660

ccgccacagg gttcccaatc tgctgatgat tcctttaaaa gaaggggaga tgggaaccca     720

aagaaaacag agaaaaaagc cttgggcgtg gtcgatggta agaactgtga aaataaaaat     780

gagcatttga agactggttc tcatatggag aactccatca ggttgtccac tgatttggaa     840

gatgtagctg ggaaatcatc cgcagtgaga aatggaaaag acactgatgg atgtgcctta     900

attcaagata agaaggcaac atctgagtaa                                        930


<210> SEQ ID NO 2
<211> LENGTH: 10230
<212> TYPE: DNA
<213> ORGANISM: Artificial Sequence
<220> FEATURE:
<223> OTHER INFORMATION: Plasmid pIPG1150

<400> SEQUENCE: 2

gttaacgcta gccaccacca ccaccaccac gtgtgaatta caggtgacca gctcgaattt      60
```

-continued

```
ccccgatcgt tcaaacattt ggcaataaag tttcttaaga ttgaatcctg ttgccggtct    120
tgcgatgatt atcatataat ttctgttgaa ttacgttaag catgtaataa ttaacatgta    180
atgcatgacg ttatttatga gatgggtttt tatgattaga gtcccgcaat tatacattta    240
atacgcgata gaaaacaaaa tatagcgcgc aaactaggat aaattatcgc gcgcggtgtc    300
atctatgtta ctagatcggg aattaaacta tcagtgtttg acaggatata ttggcgggta    360
aacctaagag aaaagagcgt ttattagaat aacggatatt taaaagggcg tgaaaaggtt    420
tatccgttcg tccatttgta tgtgcatgcc aaccacaggg ttcccctcgg gatcaaagta    480
ctttgatcca acccctccgc tgctatagtg cagtcggctt ctgacgttca gtgcagccgt    540
cttctgaaaa cgacatgtcg cacaagtcct aagttacgcg acaggctgcc gccctgccct    600
tttcctggcg ttttcttgtc gcgtgtttta gtcgcataaa gtagaatact tgcgactaga    660
accggagaca ttacgccatg aacaagagcg ccgccgctgg cctgctgggc tatgcccgcg    720
tcagcaccga cgaccaggac ttgaccaacc aacgggccga actgcacgcg gccggctgca    780
ccaagctgtt ttccgagaag atcaccggca ccaggcgcga ccgcccggag ctggccagga    840
tgcttgacca cctacgccct ggcgacgttg tgacagtgac caggctagac cgcctggccc    900
gcagcacccg cgacctactg gacattgccg agcgcatcca ggaggccggc gcgggcctgc    960
gtagcctggc agagccgtgg gccgacacca ccacgccggc cggccgcatg gtgttgaccg   1020
tgttcgccgg cattgccgag ttcgagcgtt ccctaatcat cgaccgcacc cggagcgggc   1080
gcgaggccgc caaggcccga ggcgtgaagt ttggcccccg ccctaccctc accccggcac   1140
agatcgcgca cgcccgcgag ctgatcgacc aggaaggccg caccgtgaaa gaggcggctg   1200
cactgcttgg cgtgcatcgc tcgaccctgt accgcgcact tgagcgcagc gaggaagtga   1260
cgcccaccga ggccaggcgg cgcggtgcct tccgtgagga cgcattgacc gaggccgacg   1320
ccctggcggc cgccgagaat gaacgccaag aggaacaagc atgaaaccgc accaggacgg   1380
ccaggacgaa ccgtttttca ttaccgaaga gatcgaggcg gagatgatcg cggccgggta   1440
cgtgttcgag ccgcccgcgc acgtctcaac cgtgcggctg catgaaatcc tggccggttt   1500
gtctgatgcc aagctggcgg cctggccggc cagcttggcc gctgaagaaa ccgagcgccg   1560
ccgtctaaaa aggtgatgtg tatttgagta aaacagcttg cgtcatgcgg tcgctgcgta   1620
tatgatgcga tgagtaaata aacaaatacg caaggggaac gcatgaaggt tatcgctgta   1680
cttaaccaga aaggcgggtc aggcaagacg accatcgcaa cccatctagc ccgcgccctg   1740
caactcgccg gggccgatgt tctgttagtc gattccgatc cccagggcag tgcccgcgat   1800
tgggcggccg tgcgggaaga tcaaccgcta accgttgtcg gcatcgaccg cccgacgatt   1860
gaccgcgacg tgaaggccat cggccggcgc gacttcgtag tgatcgacgg agcgccccag   1920
gcggcggact tggctgtgtc cgcgatcaag gcagccgact tcgtgctgat tccggtgcag   1980
ccaagccctt acgacatatg ggccaccgcc gacctggtgg agctggttaa gcagcgcatt   2040
gaggtcacgg atggaaggct acaagcggcc tttgtcgtgt cgcgggcgat caaaggcacg   2100
cgcatcggcg gtgaggttgc cgaggcgctg gccgggtacg agctgcccat tcttgagtcc   2160
cgtatcacgc agcgcgtgag ctacccaggc actgccgccg ccggcacaac cgttcttgaa   2220
tcagaacccg agggcgacgc tgcccgcgag gtccaggcgc tggccgctga aattaaatca   2280
aaactcattt gagttaatga ggtaaagaga aaatgagcaa aagcacaaac acgctaagtg   2340
ccggccgtcc gagcgcacgc agcagcaagg ctgcaacgtt ggccagcctg gcagacacgc   2400
```

-continued cagccatgaa gcgggtcaac tttcagttgc cggcggagga tcacaccaag ctgaagatgt 2460
acgcggtacg ccaaggcaag accattaccg agctgctatc tgaatacatc gcgcagctac 2520
cagagtaaat gagcaaatga ataaatgagt agatgaattt tagcggctaa aggaggcggc 2580
atggaaaatc aagaacaacc aggcaccgac gccgtggaat gccccatgtg tggaggaacg 2640
ggcggttggc caggcgtaag cggctgggtt gtctgccggc cctgcaatgg cactggaacc 2700
cccaagcccg aggaatcggc gtgacggtcg caaaccatcc ggcccggtac aaatcggcgc 2760
ggcgctgggt gatgacctgg tggagaagtt gaaggccgcg caggccgccc agcggcaacg 2820
catcgaggca gaagcacgcc ccggtgaatc gtggcaagcg gccgctgatc gaatccgcaa 2880
agaatcccgg caaccgccgg cagccggtgc gccgtcgatt aggaagccgc ccaagggcga 2940
cgagcaacca gattttttcg ttccgatgct ctatgacgtg ggcacccgcg atagtcgcag 3000
catcatggac gtggccgttt tccgtctgtc gaagcgtgac cgacgagctg gcgaggtgat 3060
ccgctacgag cttccagacg ggcacgtaga ggtttccgca gggccggccg gcatggccag 3120
tgtgtgggat tacgacctgg tactgatggc ggtttcccat ctaaccgaat ccatgaaccg 3180
ataccgggaa gggaagggag acaagcccgg ccgcgtgttc cgtccacacg ttgcggacgt 3240
actcaagttc tgccggcgag ccgatggcgg aaagcagaaa gacgacctgg tagaaacctg 3300
cattcggtta aacaccacgc acgttgccat gcagcgtacg aagaaggcca agaacggccg 3360
cctggtgacg gtatccgagg gtgaagcctt gattagccgc tacaagatcg taaagagcga 3420
aaccgggcgg ccggagtaca tcgagatcga gctagctgat tggatgtacc gcgagatcac 3480
agaaggcaag aacccggacg tgctgacggt tcaccccgat tactttttga tcgatcccgg 3540
catcggccgt tttctctacc gcctggcacg ccgcgccgca ggcaaggcag aagccagatg 3600
gttgttcaag acgatctacg aacgcagtgg cagcgccgga gagttcaaga agttctgttt 3660
caccgtgcgc aagctgatcg ggtcaaatga cctgccggag tacgatttga aggaggaggc 3720
ggggcaggct ggcccgatcc tagtcatgcg ctaccgcaac ctgatcgagg gcgaagcatc 3780
cgccggttcc taatgtacgg agcagatgct agggcaaatt gccctagcag gggaaaaagg 3840
tcgaaaaggt ctctttcctg tggatagcac gtacattggg aacccaaagc cgtacattgg 3900
gaaccggaac ccgtacattg ggaacccaaa gccgtacatt gggaaccggt cacacatgta 3960
agtgactgat ataaaagaga aaaaaggcga tttttccgcc taaaactctt taaaacttat 4020
taaaactctt aaaacccgcc tggcctgtgc ataactgtct ggccagcgca cagccgaaga 4080
gctgcaaaaa gcgcctaccc ttcggtcgct gcgctcccta cgccccgccg cttcgcgtcg 4140
gcctatcgcg gccgctggcc gctcaaaaat ggctggccta cggccaggca atctaccagg 4200
gcgcggacaa gccgcgccgt cgccactcga ccgccggcgc ccacatcaag gcaccctgcc 4260
tcgcgcgttt cggtgatgac ggtgaaaacc tctgacacat gcagctcccg gagacggtca 4320
cagcttgtct gtaagcggat gccgggagca gacaagcccg tcagggcgcg tcagcgggtg 4380
ttggcgggtg tcggggcgca gccatgaccc agtcacgtag cgatagcgga gtgtatactg 4440
gcttaactat gcggcatcag agcagattgt actgagagtg caccatatgc ggtgtgaaat 4500
accgcacaga tgcgtaagga gaaaataccg catcaggcgc tcttccgctt cctcgctcac 4560
tgactcgctg cgctcggtcg ttcggctgcg gcgagcggta tcagctcact caaaggcggt 4620
aatacggtta tccacagaat caggggataa cgcaggaaag aacatgtgag caaaaggcca 4680
gcaaaaggcc aggaaccgta aaaaggccgc gttgctggcg tttttccata ggctccgccc 4740
ccctgacgag catcacaaaa atcgacgctc aagtcagagg tggcgaaacc cgacaggact 4800

-continued

```
ataaagatac caggcgtttc cccctggaag ctccctcgtg cgctctcctg ttccgaccct   4860
gccgcttacc ggatacctgt ccgcctttct cccttcggga agcgtggcgc tttctcatag   4920
ctcacgctgt aggtatctca gttcggtgta ggtcgttcgc tccaagctgg gctgtgtgca   4980
cgaacccccc gttcagcccg accgctgcgc cttatccggt aactatcgtc ttgagtccaa   5040
cccggtaaga cacgacttat cgccactggc agcagccact ggtaacagga ttagcagagc   5100
gaggtatgta ggcggtgcta cagagttctt gaagtggtgg cctaactacg gctacactag   5160
aaggacagta tttggtatct gcgctctgct gaagccagtt accttcggaa aaagagttgg   5220
tagctcttga tccggcaaac aaaccaccgc tggtagcggt ggtttttttg tttgcaagca   5280
gcagattacg cgcagaaaaa aaggatctca agaagatcct ttgatctttt ctacggggtc   5340
tgacgctcag tggaacgaaa actcacgtta agggattttg gtcatgcatt ctaggtacta   5400
aaacaattca tccagtaaaa tataatattt tattttctcc caatcaggct tgatccccag   5460
taagtcaaaa aatagctcga catactgttc ttccccgata tcctccctga tcgaccggac   5520
gcagaaggca atgtcatacc acttgtccgc cctgccgctt ctcccaagat caataaagcc   5580
acttactttg ccatctttca caaagatgtt gctgtctccc aggtcgccgt gggaaaagac   5640
aagttcctct tcgggctttt ccgtctttaa aaaatcatac agctcgcgcg gatctttaaa   5700
tggagtgtct tcttcccagt tttcgcaatc cacatcggcc agatcgttat tcagtaagta   5760
atccaattcg gctaagcggc tgtctaagct attcgtatag ggacaatccg atatgtcgat   5820
ggagtgaaag agcctgatgc actccgcata cagctcgata atcttttcag ggctttgttc   5880
atcttcatac tcttccgagc aaaggacgcc atcggcctca ctcatgagca gattgctcca   5940
gccatcatgc cgttcaaagt gcaggacctt tggaacaggc agctttcctt ccagccatag   6000
catcatgtcc ttttcccgtt ccacatcata ggtggtccct ttataccggc tgtccgtcat   6060
ttttaaatat aggttttcat ttctcccac cagcttatat accttagcag gagacattcc   6120
ttccgtatct tttacgcagc ggtatttttc gatcagtttt ttcaattccg gtgatattct   6180
cattttagcc atttattatt tccttcctct tttctacagt atttaaagat accccaagaa   6240
gctaattata acaagacgaa ctccaattca ctgttccttg cattctaaaa ccttaaatac   6300
cagaaaacag ctttttcaaa gttgttttca aagttggcgt ataacatagt atcgacggag   6360
ccgattttga aaccgcggtg atcacaggca gcaacgctct gtcatcgtta caatcaacat   6420
gctaccctcc gcgagatcat ccgtgtttca aacccggcag cttagttgcc gttcttccga   6480
atagcatcgg taacatgagc aaagtctgcc gccttacaac ggctctcccg ctgacgccgt   6540
cccggactga tgggctgcct gtatcgagtg gtgattttgt gccgagctgc cggtcgggga   6600
gctgttggct ggctggtggc aggatatatt gtggtgtaaa caaattgacg cttagacaac   6660
ttaataacac attgcggacg tttttaatgt actgaattaa cgccgaatta attcggggga   6720
tctggatttt agtactggat tttggtttta ggaattagaa attttattga tagaagtatt   6780
ttacaaatac aaatacatac taagggtttc ttatatgctc aacacatgag cgaaacccta   6840
taggaaccct aattccctta tctgggaact actcacacat tattatggag aaactcgagc   6900
ttgtcgatcg actctagcta gaggatcgat ccgaacccca gagtcccgct cagaagaact   6960
cgtcaagaag gcgatagaag gcgatgcgct gcgaatcggg agcggcgata ccgtaaagca   7020
cgaggaagcg gtcagcccat tcgccgccaa gctcttcagc aatatcacgg gtagccaacg   7080
ctatgtcctg atagcggtcc gccacaccca gccggccaca gtcgatgaat ccagaaaagc   7140
```

-continued

```
ggccattttc caccatgata ttcggcaagc aggcatcgca atgggtcacg acgagatcat   7200
cgccgtcggg catgcgcgcc ttgagcctgg cgaacagttc ggctggcgcg agcccctgat   7260
gctcttcgtc cagatcatcc tgatcgacaa gaccggcttc catccgagta cgtgctcgct   7320
cgatgcgatg tttcgcttgg tggtcgaatg ggcaggtagc cggatcaagc gtatgcagcc   7380
gccgcattgc atcagccatg atggatactt tctcggcagg agcaaggtga gatgacagga   7440
gatcctgccc cggcacttcg cccaatagca gccagtccct tcccgcttca gtgacaacgt   7500
cgagcacagc tgcgcaagga acgcccgtcg tggccagcca cgatagccgc gctgcctcgt   7560
cctgcagttc attcagggca ccggacaggt cggtcttgac aaaaagaacc gggcgcccct   7620
gcgctgacag ccggaacacg gcggcatcag agcagccgat tgtctgttgt gcccagtcat   7680
agccgaatag cctctccacc caagcggccg gagaacctgc gtgcaatcca tcttgttcaa   7740
tcatgcgaaa cgatccagat ccggtgcaga ttatttggat tgagagtgaa tatgagactc   7800
taattggata ccgaggggaa tttatggaac gtcagtggag cattttgac aagaaatatt   7860
tgctagctga tagtgacctt aggcgacttt tgaacgcgca ataatggttt ctgacgtatg   7920
tgcttagctc attaaactcc agaaacccgc ggctgagtgg ctccttcaat cgttgcggtt   7980
ctgtcagttc caaacgtaaa acggcttgtc ccgcgtcatc ggcgggggtc ataacgtgac   8040
tcccttaatt ctccgctcat gatcagattg tcgtttcccg ccttcagttt ccaagcttgg   8100
cactggccgt cgttttacaa cgtcgtgact gggaaaaccc tggcgttacc caacttaatc   8160
gccttgcagc acatcccct ttcgccagct ggcgtaatag cgaagaggcc cgcaccgatc   8220
gcccttccca acagttgcgc agcctgaatg gcgaatgcta gagcagcttg agcttggatc   8280
agattgtcgt ttcccgcctt cagtttagct tcatggagtc aaagattcaa atagaggacc   8340
taacagaact cgccgtaaag actggcgaac agttcataca gagtctctta cgactcaatg   8400
acaagaagaa aatcttcgtc aacatggtgg agcacgacac acttgtctac tccaaaaata   8460
tcaaagatac agtctcagaa gaccaaaggg caattgagac ttttcaacaa agggtaatat   8520
ccggaaacct cctcggattc cattgcccag ctatctgtca ctttattgtg aagatagtgg   8580
aaaaggaagg tggctcctac aaatgccatc attgcgataa aggaaaggcc atcgttgaag   8640
atgcctctgc cgacagtggt cccaaagatg gacccccacc cacgaggagc atcgtggaaa   8700
aagaagacgt tccaaccacg tcttcaaagc aagtggattg atgtgatatc tccactgacg   8760
taagggatga cgcacaatcc cactatcctt cgcaagaccc ttcctctata taaggaagtt   8820
catttcattt ggagagaaca cgggggactc ttgaccatgg ttactcagat gttgccttct   8880
tatcttgaat taaggcacat ccatcagtgt cttttccatt tctcactgcg gatgatttcc   8940
cagctacatc ttccaaatca gtggacaacc tgatggagtt ctccatatga gaaccagtct   9000
tcaaatgctc atttttattt tcacagttct taccatcgac cacgcccaag gcttttttct   9060
ctgttttctt tgggttccca tctccccttc ttttaaagga atcatcagca gattgggaac   9120
cctgtggcgg gctctctttc aatactgatg aagcagaagg cttgtgaacg tattcgtctg   9180
tctgtctttt caggcctgga ggactagggg atctggaatt cccattacca tttttcttct   9240
ttgacaaagg ttccagtctc agacaaacag gaggtaattt tgttgtcttc ggtggagatg   9300
aggactgtct catcttactg gttctggagg aattatctgc tgcaactcca ttctcagcac   9360
tgtcagagtg gtcctccctg cacatttcca cttgccttac aggaataatt tttttattag   9420
cagtgccctc catcagttgt gagcttttag ccttattatc agaaaaatcg tcgtttggct   9480
caaaattttt catcctttca tcactctctg gaggcttcac ctgcataaac ttagaatcag   9540
```

```
aaggtgattc ttcggctgat attgaagcaa cattcttctc ctttcgatct ttcttttcaa   9600

cctccccttc ctcagtttga aaaggcatcc aaaaaaaggg gtacggaaat tgttggttca   9660

ctttttcttt atcatcttca ccatgcatta agatctgaac gcgtatgaat gttacgtcct   9720

gtagaaaccc caacccgtga aatcaaaaaa ctcgacggcc tgtgggcatt cagtctggat   9780

cgcgaaaact gtggaattga tcagcgttgg tgggaaagcg cgttacaaga aagccgggca   9840

attgctgtgc caggcagttt taacgatcag ttcgccgatg cagatattcg taattatgcg   9900

ggcaacgtct ggtatcagcg cgaagtcttt atatcgaaag gttgggcagg ccagcgtatc   9960

gtgctgcgtt tcgatgcggt cactcattac ggcaaagtgt gggtcaataa tcaggaagtg  10020

atggagcatc agggcggcta tacgccattt gaagccgatg tcacgccgta tgttattgcc  10080

gggaaaagtg tacgtatcac cgtttgtgtg aacaacgaac tgaactggca gactatcccg  10140

ccgggaatgg tgattaccga cgaaaacggc aagaaaaagc agtcttactt ccatgatttc  10200

tttaactatg ccggaatcca tcgcactagt                                    10230
```

```
<210> SEQ ID NO 3
<211> LENGTH: 10816
<212> TYPE: DNA
<213> ORGANISM: Artificial Sequence
<220> FEATURE:
<223> OTHER INFORMATION: Plasmid pIPG1160

<400> SEQUENCE: 3

tgctacagag ttcttgaagt ggtggcctaa ctacggctac actagaagga cagtatttgg     60

tatctgcgct ctgctgaagc cagttacctt cggaaaaaga gttggtagct cttgatccgg    120

caaacaaacc accgctggta gcggtggttt ttttgtttgc aagcagcaga ttacgcgcag    180

aaaaaaagga tctcaagaag atcctttgat cttttctacg gggtctgacg ctcagtggaa    240

cgaaaactca cgttaaggga ttttggtcat gcatgatata tctcccaatt tgtgtagggc    300

ttattatgca cgcttaaaaa taataaaagc agacttgacc tgatagtttg gctgtgagca    360

attatgtgct tagtgcatct aatcgcttga gttaacgccg gcgaagcggc gtcggcttga    420

acgaatttct agctagacat tatttgccga ctaccttggt gatctcgcct ttcacgtagt    480

ggacaaattc ttccaactga tctgcgcgcg aggccaagcg atcttcttct tgtccaagat    540

aagcctgtct agcttcaagt atgacgggct gatactgggc cggcaggcgc tccattgccc    600

agtcggcagc gacatccttc ggcgcgattt tgccggttac tgcgctgtac caaatgcggg    660

acaacgtaag cactacattt cgctcatcgc cagcccagtc gggcggcgag ttccatagcg    720

ttaaggtttc atttagcgcc tcaaatagat cctgttcagg aaccggatca aagagttcct    780

ccgccgctgg acctaccaag gcaacgctat gttctcttgc ttttgtcagc aagatagcca    840

gatcaatgtc gatcgtggct ggctcgaaga tacctgcaag aatgtcattg cgctgccatt    900

ctccaaattg cagttcgcgc ttagctggat aacgccacgg aatgatgtcg tcgtgcacaa    960

caatggtgac ttctacagcg cggagaatct cgctctctcc aggggaagcc gaagtttcca   1020

aaaggtcgtt gatcaaagct cgccgcgttg tttcatcaag ccttacggtc accgtaacca   1080

gcaaatcaat atcactgtgt ggcttcaggc cgccatccac tgcggagccg tacaaatgta   1140

cggccagcaa cgtcggttcg agatggcgct cgatgacgcc aactacctct gatagttgag   1200

tcgatacttc ggcgatcacc gcttccccca tgatgtttaa ctttgtttta gggcgactgc   1260

cctgctgcgt aacatcgttg ctgctccata acatcaaaca tcgacccacg gcgtaacgcg   1320
```

-continued

```
cttgctgctt ggatgcccga ggcatagact gtaccccaaa aaaacatgtc ataacaagaa   1380
gccatgaaaa ccgccactgc gccgttacca ccgctgcgtt cggtcaaggt tctggaccag   1440
ttgcgtgacg gcagttacgc tacttgcatt acagcttacg aaccgaacga ggcttatgtc   1500
cactgggttc gtgcccgaat tgatcacagg cagcaacgct ctgtcatccg cggtgatcac   1560
aggcagcaac gctctgtcat cgttacaatc aacatgctac cctccgcgag atcatccgtg   1620
tttcaaaccc ggcagcttag ttgccgttct tccgaatagc atcggtaaca tgagcaaagt   1680
ctgccgcctt acaacggctc tcccgctgac gccgtcccgg actgatgggc tgcctgtatc   1740
gagtggtgat tttgtgccga gctgccggtc ggggagctgt tggctggctg gtggcaggat   1800
atattgtggt gtaaacaaat tgacgcttag acaacttaat aacacattgc ggacgttttt   1860
aatgtactga attaacgccg aattaattcg gggatctgg attttagtac tggattttgg    1920
ttttaggaat tagaaatttt attgatagaa gtattttaca aatacaaata catactaagg   1980
gtttcttata tgctcaacac atgagcgaaa ccctatagga accctaattc ccttatctgg   2040
gaactactca cacattatta tggagaaact cgagcttgtc gatcgactct agctagagga   2100
tcgatccgaa ccccagagtc ccgctcagaa gaactcgtca agaaggcgat agaaggcgat   2160
gcgctgcgaa tcgggagcgg cgataccgta aagcacgagg aagcggtcag cccattcgcc   2220
gccaagctct tcagcaatat cacgggtagc caacgctatg tcctgatagc ggtccgccac   2280
acccagccgg ccacagtcga tgaatccaga aaagcggcca ttttccacca tgatattcgg   2340
caagcaggca tcgccatggg tcacgacgag atcatcgccg tcgggcatgc gcgccttgag   2400
cctggcgaac agttcggctg gcgcgagccc ctgatgctct tcgtccagat catcctgatc   2460
gacaagaccg gcttccatcc gagtacgtgc tcgctcgatg cgatgtttcg cttggtggtc   2520
gaatgggcag gtagccggat caagcgtatg cagccgccgc attgcatcag ccatgatgga   2580
tactttctcg gcaggagcaa ggtgagatga caggagatcc tgccccggca cttcgcccaa   2640
tagcagccag tcccttcccg cttcagtgac aacgtcgagc acagctgcgc aaggaacgcc   2700
cgtcgtggcc agccacgata gccgcgctgc ctcgtcctgc agttcattca gggcaccgga   2760
caggtcggtc ttgacaaaaa gaaccgggcg cccctgcgct gacagccgga acacggcggc   2820
atcagagcag ccgattgtct gttgtgccca gtcatagccg aatagcctct ccacccaagc   2880
ggccggagaa cctgcgtgca atccatcttg ttcaatcatg cgaaacgatc cagatccggt   2940
gcagattatt tggattgaga gtgaatatga gactctaatt ggataccgag gggaatttat   3000
ggaacgtcag tggagcattt ttgacaagaa atatttgcta gctgatagtg accttaggcg   3060
acttttgaac gcgcaataat ggtttctgac gtatgtgctt agctcattaa actccagaaa   3120
cccgcggctg agtggctcct tcaatcgttg cggttctgtc agttccaaac gtaaaacggc   3180
ttgtcccgcg tcatcggcgg gggtcataac gtgactccct taattctccg ctcatgatca   3240
gattgtcgtt tcccgccttc agtttccaag cttgcaaaat agcacaccat ttatgtttat   3300
attttcaaat tatttaatac atttcaatat ttcataagtg tgattttttt tttttttgtc   3360
aatttcataa gtgtgatttg tcatttgtat taaacaattg tatcgcgcag tacaaataaa   3420
cagtgggaga ggtgaaaatg cagttataaa actgtccaat aatttactaa cacatttaaa   3480
tatctaaaaa gagtgtttca aaaaaaattc ttttgaaata agaaaagtga tagatatttt   3540
tacgctttcg tctgaaaata aaacaataat agtttattag aaaaatgtta tcaccgaaaa   3600
ttattctagt gccactcgct cggatcgaaa ttcgaaagtt atattctttc tctttaccta   3660
atataaaaat cacaagaaaa atcaatccga atatatctat caacatagta tatgccctta   3720
```

-continued catattgttt ctgacttttc tctatccgaa tttctcgctt catggttttt ttttaacata 3780
ttctcattta attttcatta ctattatata actaaaagat ggaaataaaa taaagtgtct 3840
ttgagaatcg aacgtccata tcagtaagat agtttgtgtg aaggtaaaat ctaaaagatt 3900
taagttccaa aaacagaaaa taatatatta cgctaaaaaa gaagaaaata attaaataca 3960
aaacagaaaa aaataatata cgacagacac gtgtcacgaa gataccctac gctatagaca 4020
cagctctgtt ttctctttc tatgcctcaa ggctctctta acttcactgt ctcctcttcg 4080
gataatccta tccttctctt cctataaata cctctccact cttcctcttc ctccaccact 4140
acaaccaccg caacaaccac caaaaaccct ctcaaagaaa tttctttttt ttcttacttt 4200
cttggtttgt caaaccatgg ggatgtctat aaatataaga gaccctctta tagtaagcag 4260
agttgttgga gacgttcttg atccgtttaa tagatcaatc actctaaagg ttacttatgg 4320
ccaaactcga gttactcaga tgttgccttc ttatcttgaa ttaaggcaca tccatcagtg 4380
tcttttccat ttctcactgc ggatgatttc ccagctacat cttccaaatc agtggacaac 4440
ctgatggagt tctccatatg agaaccagtc ttcaaatgct catttttatt ttcacagttc 4500
ttaccatcga ccacgcccaa ggcttttttc tctgttttct ttgggttccc atctcccctt 4560
cttttaaagg aatcatcagc agattgggaa ccctgtggcg ggctctcttt caatactgat 4620
gaagcagaag gcttgtgaac gtattcgtct gtctgtcttt tcaggcctgg aggactaggg 4680
gatctggaat tcccattacc atttttcttc tttgacaaag gttccagtct cagacaaaca 4740
ggaggtaatt ttgttgtctt cggtggagat gaggactgtc tcatcttact ggttctggag 4800
gaattatctg ctgcaactcc attctcagca ctgtcagagt ggtcctccct gcacatttcc 4860
acttgcctta caggaataat ttttttatta gcagtgccct ccatcagttg tgagctttta 4920
gccttattat cagaaaaatc gtcgtttggc tcaaaatttt tcatcctttc atcactctct 4980
ggaggcttca cctgcataaa cttagaatca gaaggtgatt cttcggctga tattgaagca 5040
acattcttct cctttcgatc tttcttttca acctcccctt cctcagtttg aaaaggcatc 5100
caaaaaaagg ggtacggaaa ttgttggttc actttttctt tatcatcttc accatgcatt 5160
aagatctgaa cgcgtatgaa tgttacgtcc tgtagaaacc ccaacccgtg aaatcaaaaa 5220
actcgacggc ctgtgggcat tcagtctgga tcgcgaaaac tgtggaattg atcagcgttg 5280
gtgggaaagc gcgttacaag aaagccgggc aattgctgtg ccaggcagtt ttaacgatca 5340
gttcgccgat gcagatattc gtaattatgc gggcaacgtc tggtatcagc gcgaagtctt 5400
tatatcgaaa ggttgggcag gccagcgtat cgtgctgcgt ttcgatgcgg tcactcatta 5460
cggcaaagtg tgggtcaata atcaggaagt gatggagcat cagggcggct atacgccatt 5520
tgaagccgat gtcacgccgt atgttattgc cgggaaaagt gtacgtatca ccgtttgtgt 5580
gaacaacgaa ctgaactggc agactatccc gccgggaatg gtgattaccg acgaaaacgg 5640
caagaaaaag cagtcttact tccatgattt ctttaactat gccggaatcc atcgcactag 5700
tgttaacgct agccaccacc accaccacca cgtgtgaatt acaggtgacc agctcgaatt 5760
tccccgatcg ttcaaacatt tggcaataaa gtttcttaag attgaatcct gttgccggtc 5820
ttgcgatgat tatcatataa tttctgttga attacgttaa gcatgtaata attaacatgt 5880
aatgcatgac gttatttatg agatgggttt ttatgattag agtcccgcaa ttatacattt 5940
aatacgcgat agaaaacaaa atatagcgcg caaactagga taaattatcg cgcgcggtgt 6000
catctatgtt actagatcgg gaattaaact atcagtgttt gacaggatat attggcgggt 6060

-continued

```
aaacctaaga gaaaagagcg tttattagaa taacggatat ttaaaagggc gtgaaaaggt   6120
ttatccgttc gtccatttgt atgtgcatgc caaccacagg gttcccctcg ggatcaaagt   6180
actttgatcc aacccctccg ctgctatagt gcagtcggct tctgacgttc agtgcagccg   6240
tcttctgaaa acgacatgtc gcacaagtcc taagttacgc gacaggctgc cgccctgccc   6300
ttttcctggc gttttcttgt cgcgtgtttt agtcgcataa agtagaatac ttgcgactag   6360
aaccggagac attacgccat gaacaagagc gccgccgctg gcctgctggg ctatgcccgc   6420
gtcagcaccg acgaccagga cttgaccaac caacgggccg aactgcacgc ggccggctgc   6480
accaagctgt tttccgagaa gatcaccggc accaggcgcg accgcccgga gctggccagg   6540
atgcttgacc acctacgccc tggcgacgtt gtgacagtga ccaggctaga ccgcctggcc   6600
cgcagcaccc gcgacctact ggacattgcc gagcgcatcc aggaggccgg cgcgggcctg   6660
cgtagcctgg cagagccgtg ggccgacacc accacgccgg ccggccgcat ggtgttgacc   6720
gtgttcgccg gcattgccga gttcgagcgt tccctaatca tcgaccgcac ccggagcggg   6780
cgcgaggccg ccaaggcccg aggcgtgaag tttggccccc gccctaccct caccccggca   6840
cagatcgcgc acgcccgcga gctgatcgac caggaaggcc gcaccgtgaa agaggcggct   6900
gcactgcttg gcgtgcatcg ctcgaccctg taccgcgcac ttgagcgcag cgaggaagtg   6960
acgcccaccg aggccaggcg gcgcggtgcc ttccgtgagg acgcattgac cgaggccgac   7020
gccctggcgg ccgccgagaa tgaacgccaa gaggaacaag catgaaaccg caccaggacg   7080
gccaggacga accgtttttc attaccgaag agatcgaggc ggagatgatc gcggccgggt   7140
acgtgttcga gccgcccgcg cacgtctcaa ccgtgcggct gcatgaaatc ctggccggtt   7200
tgtctgatgc caagctggcg gcctggccgg ccagcttggc cgctgaagaa accgagcgcc   7260
gccgtctaaa aaggtgatgt gtatttgagt aaaacagctt gcgtcatgcg gtcgctgcgt   7320
atatgatgcg atgagtaaat aaacaaatac gcaaggggaa cgcatgaagg ttatcgctgt   7380
acttaaccag aaaggcgggt caggcaagac gaccatcgca acccatctag cccgcgccct   7440
gcaactcgcc ggggccgatg ttctgttagt cgattccgat ccccagggca gtgcccgcga   7500
ttgggcggcc gtgcgggaag atcaaccgct aaccgttgtc ggcatcgacc gcccgacgat   7560
tgaccgcgac gtgaaggcca tcggccggcg cgacttcgta gtgatcgacg gagcgcccca   7620
ggcggcggac ttggctgtgt ccgcgatcaa ggcagccgac ttcgtgctga ttccggtgca   7680
gccaagccct tacgacatat gggccaccgc cgacctggtg gagctggtta agcagcgcat   7740
tgaggtcacg gatggaaggc tacaagcggc ctttgtcgtg tcgcgggcga tcaaaggcac   7800
gcgcatcggc ggtgaggttg ccgaggcgct ggccgggtac gagctgccca ttcttgagtc   7860
ccgtatcacg cagcgcgtga gctacccagg cactgccgcc gccggcacaa ccgttcttga   7920
atcagaaccc gagggcgacg ctgcccgcga ggtccaggcg ctggccgctg aaattaaatc   7980
aaaactcatt tgagttaatg aggtaaagag aaaatgagca aaagcacaaa cacgctaagt   8040
gccggccgtc cgagcgcacg cagcagcaag gctgcaacgt tggccagcct ggcagacacg   8100
ccagccatga agcgggtcaa ctttcagttg ccggcggagg atcacaccaa gctgaagatg   8160
tacgcggtac gccaaggcaa gaccattacc gagctgctat ctgaatacat cgcgcagcta   8220
ccagagtaaa tgagcaaatg aataaatgag tagatgaatt ttagcggcta aaggaggcgg   8280
catggaaaat caagaacaac caggcaccga cgccgtggaa tgccccatgt gtggaggaac   8340
gggcggttgg ccaggcgtaa gcggctgggt tgtctgccgg ccctgcaatg gcactggaac   8400
cccaagcccc gaggaatcgg cgtgacggtc gcaaaccatc cggcccggta caaatcggcg   8460
```

-continued

```
cggcgctggg tgatgacctg gtggagaagt tgaaggccgc gcaggccgcc cagcggcaac   8520
gcatcgaggc agaagcacgc cccggtgaat cgtggcaagc ggccgctgat cgaatccgca   8580
aagaatcccg gcaaccgccg gcagccggtg cgccgtcgat taggaagccg cccaagggcg   8640
acgagcaacc agatttttc gttccgatgc tctatgacgt gggcacccgc gatagtcgca   8700
gcatcatgga cgtggccgtt ttccgtctgt cgaagcgtga ccgacgagct ggcgaggtga   8760
tccgctacga gcttccagac gggcacgtag aggtttccgc agggccggcc ggcatggcca   8820
gtgtgtggga ttacgacctg gtactgatgg cggtttccca tctaaccgaa tccatgaacc   8880
gataccggga agggaaggga gacaagcccg gccgcgtgtt ccgtccacac gttgcggacg   8940
tactcaagtt ctgccggcga gccgatggcg gaaagcagaa agacgacctg gtagaaacct   9000
gcattcggtt aaacaccacg cacgttgcca tgcagcgtac gaagaaggcc aagaacggcc   9060
gcctggtgac ggtatccgag ggtgaagcct tgattagccg ctacaagatc gtaaagagcg   9120
aaaccgggcg gccggagtac atcgagatcg agctagctga ttggatgtac cgcgagatca   9180
cagaaggcaa gaacccggac gtgctgacgg ttcaccccga ttactttttg atcgatcccg   9240
gcatcggccg ttttctctac cgcctggcac gccgcgccgc aggcaaggca gaagccagat   9300
ggttgttcaa gacgatctac gaacgcagtg gcagcgccgg agagttcaag aagttctgtt   9360
tcaccgtgcg caagctgatc gggtcaaatg acctgccgga gtacgatttg aaggaggagg   9420
cggggcaggc tggcccgatc ctagtcatgc gctaccgcaa cctgatcgag ggcgaagcat   9480
ccgccggttc ctaatgtacg gagcagatgc tagggcaaat tgccctagca ggggaaaaag   9540
gtcgaaaagg tctctttcct gtggatagca cgtacattgg gaacccaaag ccgtacattg   9600
ggaaccggaa cccgtacatt gggaacccaa agccgtacat tgggaaccgg tcacacatgt   9660
aagtgactga tataaaagag aaaaaaggcg atttttccgc ctaaaactct ttaaaactta   9720
ttaaaactct taaaacccgc ctggcctgtg cataactgtc tggccagcgc acagccgaag   9780
agctgcaaaa agcgcctacc cttcggtcgc tgcgctccct acgccccgcc gcttcgcgtc   9840
ggcctatcgc ggccgctggc cgctcaaaaa tggctggcct acggccaggc aatctaccag   9900
ggcgcggaca agccgcgccg tcgccactcg accgccggcg cccacatcaa ggcaccctgc   9960
ctcgcgcgtt tcggtgatga cggtgaaaac ctctgacaca tgcagctccc ggagacggtc  10020
acagcttgtc tgtaagcgga tgccgggagc agacaagccc gtcagggcgc gtcagcgggt  10080
gttggcgggt gtcggggcgc agccatgacc cagtcacgta gcgatagcgg agtgtatact  10140
ggcttaacta tgcggcatca gagcagattg tactgagagt gcaccatatg cggtgtgaaa  10200
taccgcacag atgcgtaagg agaaaatacc gcatcaggcg ctcttccgct tcctcgctca  10260
ctgactcgct gcgctcggtc gttcggctgc ggcgagcggt atcagctcac tcaaaggcgg  10320
taatacggtt atccacagaa tcaggggata acgcaggaaa gaacatgtga gcaaaaggcc  10380
agcaaaaggc caggaaccgt aaaaaggccg cgttgctggc gtttttccat aggctccgcc  10440
cccctgacga gcatcacaaa aatcgacgct caagtcagag gtggcgaaac ccgacaggac  10500
tataaagata ccaggcgttt ccccctggaa gctccctcgt gcgctctcct gttccgaccc  10560
tgccgcttac cggatacctg tccgcctttc tcccttcggg aagcgtggcg ctttctcata  10620
gctcacgctg taggtatctc agttcggtgt aggtcgttcg ctccaagctg ggctgtgtgc  10680
acgaaccccc cgttcagccc gaccgctgcg ccttatccgg taactatcgt cttgagtcca  10740
acccggtaag acacgactta tcgccactgg cagcagccac tggtaacagg attagcagag  10800
```

-continued cgaggtatgt aggcgg 10816

<210> SEQ ID NO 4
<211> LENGTH: 11429
<212> TYPE: DNA
<213> ORGANISM: Artificial Sequence
<220> FEATURE:
<223> OTHER INFORMATION: Plasmid pIPG1157

<400> SEQUENCE: 4
tgctacagag ttcttgaagt ggtggcctaa ctacggctac actagaagga cagtatttgg 60
tatctgcgct ctgctgaagc cagttacctt cggaaaaaga gttggtagct cttgatccgg 120
caaacaaacc accgctggta gcggtggttt ttttgtttgc aagcagcaga ttacgcgcag 180
aaaaaaagga tctcaagaag atcctttgat cttttctacg gggtctgacg ctcagtggaa 240
cgaaaactca cgttaaggga ttttggtcat gcatgatata tctcccaatt tgtgtagggc 300
ttattatgca cgcttaaaaa taataaaagc agacttgacc tgatagtttg gctgtgagca 360
attatgtgct tagtgcatct aatcgcttga gttaacgccg gcgaagcggc gtcggcttga 420
acgaatttct agctagacat tatttgccga ctaccttggt gatctcgcct ttcacgtagt 480
ggacaaattc ttccaactga tctgcgcgcg aggccaagcg atcttcttct tgtccaagat 540
aagcctgtct agcttcaagt atgacgggct gatactgggc cggcaggcgc tccattgccc 600
agtcggcagc gacatccttc ggcgcgattt tgccggttac tgcgctgtac caaatgcggg 660
acaacgtaag cactacattt cgctcatcgc cagcccagtc gggcggcgag ttccatagcg 720
ttaaggtttc atttagcgcc tcaaatagat cctgttcagg aaccggatca aagagttcct 780
ccgccgctgg acctaccaag gcaacgctat gttctcttgc ttttgtcagc aagatagcca 840
gatcaatgtc gatcgtggct ggctcgaaga tacctgcaag aatgtcattg cgctgccatt 900
ctccaaattg cagttcgcgc ttagctggat aacgccacgg aatgatgtcg tcgtgcacaa 960
caatggtgac ttctacagcg cggagaatct cgctctctcc aggggaagcc gaagtttcca 1020
aaaggtcgtt gatcaaagct cgccgcgttg tttcatcaag ccttacggtc accgtaacca 1080
gcaaatcaat atcactgtgt ggcttcaggc cgccatccac tgcggagccg tacaaatgta 1140
cggccagcaa cgtcggttcg agatggcgct cgatgacgcc aactacctct gatagttgag 1200
tcgatacttc ggcgatcacc gcttccccca tgatgtttaa ctttgtttta gggcgactgc 1260
cctgctgcgt aacatcgttg ctgctccata acatcaaaca tcgacccacg gcgtaacgcg 1320
cttgctgctt ggatgcccga ggcatagact gtaccccaaa aaaacatgtc ataacaagaa 1380
gccatgaaaa ccgccactgc gccgttacca ccgctgcgtt cggtcaaggt tctggaccag 1440
ttgcgtgacg gcagttacgc tacttgcatt acagcttacg aaccgaacga ggcttatgtc 1500
cactgggttc gtgcccgaat tgatcacagg cagcaacgct ctgtcatccg cggtgatcac 1560
aggcagcaac gctctgtcat cgttacaatc aacatgctac cctccgcgag atcatccgtg 1620
tttcaaaccc ggcagcttag ttgccgttct tccgaatagc atcggtaaca tgagcaaagt 1680
ctgccgcctt acaacggctc tcccgctgac gccgtcccgg actgatgggc tgcctgtatc 1740
gagtggtgat tttgtgccga gctgccggtc ggggagctgt tggctggctg gtggcaggat 1800
atattgtggt gtaaacaaat tgacgcttag acaacttaat aacacattgc ggacgttttt 1860
aatgtactga attaacgccg aattaattcg ggggatctgg attttagtac tggattttgg 1920
ttttaggaat tagaaatttt attgatagaa gtattttaca aatacaaata catactaagg 1980
gtttcttata tgctcaacac atgagcgaaa ccctatagga accctaattc ccttatctgg 2040

-continued gaactactca cacattatta tggagaaact cgagcttgtc gatcgactct agctagagga 2100
tcgatccgaa ccccagagtc ccgctcagaa gaactcgtca agaaggcgat agaaggcgat 2160
gcgctgcgaa tcgggagcgg cgataccgta aagcacgagg aagcggtcag cccattcgcc 2220
gccaagctct tcagcaatat cacgggtagc caacgctatg tcctgatagc ggtccgccac 2280
acccagccgg ccacagtcga tgaatccaga aaagcggcca ttttccacca tgatattcgg 2340
caagcaggca tcgccatggg tcacgacgag atcatcgccg tcgggcatgc gcgccttgag 2400
cctggcgaac agttcggctg gcgcgagccc ctgatgctct tcgtccagat catcctgatc 2460
gacaagaccg gcttccatcc gagtacgtgc tcgctcgatg cgatgtttcg cttggtggtc 2520
gaatgggcag gtagccggat caagcgtatg cagccgccgc attgcatcag ccatgatgga 2580
tactttctcg gcaggagcaa ggtgagatga caggagatcc tgccccggca cttcgcccaa 2640
tagcagccag tcccttcccg cttcagtgac aacgtcgagc acagctgcgc aaggaacgcc 2700
cgtcgtggcc agccacgata gccgcgctgc ctcgtcctgc agttcattca gggcaccgga 2760
caggtcggtc ttgacaaaaa gaaccgggcg cccctgcgct gacagccgga acacggcggc 2820
atcagagcag ccgattgtct gttgtgccca gtcatagccg aatagcctct ccacccaagc 2880
ggccggagaa cctgcgtgca atccatcttg ttcaatcatg cgaaacgatc cagatccggt 2940
gcagattatt tggattgaga gtgaatatga gactctaatt ggataccgag gggaatttat 3000
ggaacgtcag tggagcattt ttgacaagaa atatttgcta gctgatagtg accttaggcg 3060
acttttgaac gcgcaataat ggtttctgac gtatgtgctt agctcattaa actccagaaa 3120
cccgcggctg agtggctcct tcaatcgttg cggttctgtc agttccaaac gtaaaacggc 3180
ttgtcccgcg tcatcggcgg gggtcataac gtgactccct taattctccg ctcatgatca 3240
gattgtcgtt tcccgccttc agtttccaag cttggcactg gccgtcgttt tacaacgtcg 3300
tgactgggaa aaccctggcg ttacccaact taatcgcctt gcagcacatc cccctttcgc 3360
cagctggcgt aatagcgaag aggcccgcac cgatcgccct tcccaacagt tgcgcagcct 3420
gaatggcgaa tgctagagca gcttgagctt ggatcagatt gtcgtttccc gccttcagtt 3480
tagcttcatg gagtcaaaga ttcaaataga ggacctaaca gaactcgccg taaagactgg 3540
cgaacagttc atacagagtc tcttacgact caatgacaag aagaaaatct tcgtcaacat 3600
ggtggagcac gacacacttg tctactccaa aaatatcaaa gatacagtct cagaagacca 3660
aagggcaatt gagacttttc aacaaagggt aatatccgga aacctcctcg gattccattg 3720
cccagctatc tgtcacttta ttgtgaagat agtggaaaag gaaggtggct cctacaaatg 3780
ccatcattgc gataaaggaa aggccatcgt tgaagatgcc tctgccgaca gtggtcccaa 3840
agatggaccc ccacccacga ggagcatcgt ggaaaaagaa gacgttccaa ccacgtcttc 3900
aaagcaagtg gattgatgtg atatctccac tgacgtaagg gatgacgcac aatcccacta 3960
tccttcgcaa gacccttcct ctatataagg aagttcattt catttggaga gaacacgggg 4020
gactcttgac catggttctg gatgccttct aacagtgagc agagggagcc tgaaaagaag 4080
gcccaaaggc aagggaaatg ctggttgtca ctagatacaa acagccctaa actttttatg 4140
catggtgaag atgataaaga aaaagtgaac caacaatttc cgtacccctt tttttggatg 4200
ccttttcaaa ctgaggaagg ggaggttgaa aagaaccgcg ggaattcgat tgcgcgtcga 4260
catgttacgt cctgtagaaa ccccaacccg tgaaatcaaa aaactcgacg gcctgtgggc 4320
attcagtctg gatcgcgaaa actgtggaat tgatcagcgt tggtgggaaa gcgcgttaca 4380

-continued

```
agaaagccgg gcaattgctg tgccaggcag ttttaacgat cagttcgccg atgcagatat   4440
tcgtaattat gcgggcaacg tctggtatca gcgcgaagtc tttatatcga aaggttgggc   4500
aggccagcgt atcgtgctgc gtttcgatgc ggtcactcat tacggcaaag tgtgggtcaa   4560
taatcaggaa gtgatggagc atcagggcgg ctatacgcca tttgaagccg atgtcacgcc   4620
gtatgttatt gccgggaaaa gtgtacgtat caccgtttgt gtgaacaacg aactgaactg   4680
gcagactatc ccgccgggaa tggtgattac cgacgaaaac ggcaagaaaa agcagtctta   4740
cttccatgat ttctttaact atgccggaat ccatcgcagc gtaatgctct acaccacgcc   4800
gaacacctgg gtggacgata tcaccgtggt gacgcatgtc gcgcaagact gtaaccacgc   4860
gtctgttgac tggcaggtgg tggccaatgg tgatgtcagc gttgaactgc gtgatgcggg   4920
atcaacaggt ggttgcaact ggacaaggca ctagcgggac tttgcaagtg gtgaatccgc   4980
acctctggca accgggtgaa ggttatctct atgaactgtg cgtcacagcc aaaagccaga   5040
cagagtgtga tatctacccg cttcgcgtcg gcatccggtc agtggcagtg aagggcgaac   5100
agttcctgat taaccacaaa ccgttctact ttactggctt tggtcgtcat gaagatgcgg   5160
acttgcgtgg caaaaggatt cgataacgtg ctgatggtgc acgaccacgc attaatggac   5220
tggattgggg ccaactccta ccgtacctcg cattaccctt acgctgaaga gatgctcgac   5280
tgggcagatg aacatggcat cgtggtgatt gatgaaactg ctgctgtcgg ctttaacctc   5340
tctttaggca ttggtttcga agcgggcaac aagccgaaag aactgtacag cgaagaggca   5400
gtcaacgggg aaactcagca agcgcactta caggcgatta aagagctgat agcgcgtgac   5460
aaaaaccacc caagcgtggt gatgtggagt attgccaacg aaccggatac ccgtccgcaa   5520
ggtgcacggg aatatttcgc gccactggcg gaagcaacgc gtaaactcga cccgacgcgt   5580
ccgatcacct gcgtcaatgt aatgttctgc gacgctcaca ccgataccat cagcgatctc   5640
tttgatgtgc tgtgcctgaa ccgttattac ggatggtatg tccaaagcgg cgatttggaa   5700
acggcagaga aggtactgga aaaagaactt ctggcctggc aggagaaact gcatcagccg   5760
attatcatca ccgaatacgg cgtggatacg ttagccgggc tgcactcaat gtacaccgac   5820
atgtggagtg aagagtatca gtgtgcatgg ctggatatgt atcaccgcgt ctttgatcgc   5880
gtcagcgccg tcgtcggtga acaggtatgg aatttcgccg attttgcgac ctcgcaaggc   5940
atattgcgcg ttggcggtaa caagaaaggg atcttcactc gcgaccgcaa accgaagtcg   6000
gcggcttttc tgctgcaaaa acgctggact ggcatgaact tcggtgaaaa accgcagcag   6060
ggaggcaaac aagctagcca ccaccaccac caccacgtgt gactcgagtt cttttcaacc   6120
tccccttcct cagtttgaaa aggcatccaa aaaaaggggt acggaaattg ttggttcact   6180
ttttctttat catcttcacc atgcataaaa agtttagggc tgtttgtatc tagtgacaac   6240
cagcatttcc cttgcctttg ggccttcttt tcaggctccc tctgctcact gttagaaggc   6300
atccagaaac tagtgttaac gctagccacc accaccacca ccacgtgtga attacaggtg   6360
accagctcga atttccccga tcgttcaaac atttggcaat aaagtttctt aagattgaat   6420
cctgttgccg gtcttgcgat gattatcata taatttctgt tgaattacgt taagcatgta   6480
ataattaaca tgtaatgcat gacgttattt atgagatggg tttttatgat tagagtcccg   6540
caattataca tttaatacgc gatagaaaac aaaatatagc gcgcaaacta ggataaatta   6600
tcgcgcgcgg tgtcatctat gttactagat cgggaattaa actatcagtg tttgacagga   6660
tatattggcg ggtaaaccta agagaaaaga gcgtttatta gaataacgga tatttaaaag   6720
ggcgtgaaaa ggtttatccg ttcgtccatt tgtatgtgca tgccaaccac agggttcccc   6780
```

tcgggatcaa agtactttga tccaacccct ccgctgctat agtgcagtcg gcttctgacg 6840
ttcagtgcag ccgtcttctg aaaacgacat gtcgcacaag tcctaagtta cgcgacaggc 6900
tgccgccctg cccttttcct ggcgttttct tgtcgcgtgt tttagtcgca taaagtagaa 6960
tacttgcgac tagaaccgga gacattacgc catgaacaag agcgccgccg ctggcctgct 7020
gggctatgcc cgcgtcagca ccgacgacca ggacttgacc aaccaacggg ccgaactgca 7080
cgcggccggc tgcaccaagc tgttttccga gaagatcacc ggcaccaggc gcgaccgccc 7140
ggagctggcc aggatgcttg accacctacg ccctggcgac gttgtgacag tgaccaggct 7200
agaccgcctg gcccgcagca cccgcgacct actggacatt gccgagcgca tccaggaggc 7260
cggcgcgggc ctgcgtagcc tggcagagcc gtgggccgac accaccacgc cggccggccg 7320
catggtgttg accgtgttcg ccggcattgc cgagttcgag cgttccctaa tcatcgaccg 7380
cacccggagc gggcgcgagg ccgccaaggc ccgaggcgtg aagtttggcc cccgccctac 7440
cctcaccccg gcacagatcg cgcacgcccg cgagctgatc gaccaggaag gccgcaccgt 7500
gaaagaggcg gctgcactgc ttggcgtgca tcgctcgacc ctgtaccgcg cacttgagcg 7560
cagcgaggaa gtgacgccca ccgaggccag gcggcgcggt gccttccgtg aggacgcatt 7620
gaccgaggcc gacgccctgg cggccgccga gaatgaacgc caagaggaac aagcatgaaa 7680
ccgcaccagg acggccagga cgaaccgttt ttcattaccg aagagatcga ggcggagatg 7740
atcgcggccg ggtacgtgtt cgagccgccc gcgcacgtct caaccgtgcg gctgcatgaa 7800
atcctggccg gtttgtctga tgccaagctg gcggcctggc cggccagctt ggccgctgaa 7860
gaaaccgagc gccgccgtct aaaaaggtga tgtgtatttg agtaaaacag cttgcgtcat 7920
gcggtcgctg cgtatatgat gcgatgagta aataaacaaa tacgcaaggg gaacgcatga 7980
aggttatcgc tgtacttaac cagaaaggcg ggtcaggcaa gacgaccatc gcaacccatc 8040
tagcccgcgc cctgcaactc gccggggccg atgttctgtt agtcgattcc gatccccagg 8100
gcagtgcccg cgattgggcg gccgtgcggg aagatcaacc gctaaccgtt gtcggcatcg 8160
accgcccgac gattgaccgc gacgtgaagg ccatcggccg gcgcgacttc gtagtgatcg 8220
acggagcgcc ccaggcggcg gacttggctg tgtccgcgat caaggcagcc gacttcgtgc 8280
tgattccggt gcagccaagc ccttacgaca tatgggccac cgccgacctg gtggagctgg 8340
ttaagcagcg cattgaggtc acggatggaa ggctacaagc ggcctttgtc gtgtcgcggg 8400
cgatcaaagg cacgcgcatc ggcggtgagg ttgccgaggc gctggccggg tacgagctgc 8460
ccattcttga gtcccgtatc acgcagcgcg tgagctaccc aggcactgcc gccgccggca 8520
caaccgttct tgaatcagaa cccgagggcg acgctgcccg cgaggtccag gcgctggccg 8580
ctgaaattaa atcaaaactc atttgagtta atgaggtaaa gagaaaatga gcaaaagcac 8640
aaacacgcta agtgccggcc gtccgagcgc acgcagcagc aaggctgcaa cgttggccag 8700
cctggcagac acgccagcca tgaagcgggt caactttcag ttgccggcgg aggatcacac 8760
caagctgaag atgtacgcgg tacgccaagg caagaccatt accgagctgc tatctgaata 8820
catcgcgcag ctaccagagt aaatgagcaa atgaataaat gagtagatga attttagcgg 8880
ctaaaggagg cggcatggaa aatcaagaac aaccaggcac cgacgccgtg gaatgcccca 8940
tgtgtggagg aacgggcggt tggccaggcg taagcggctg ggttgtctgc cggccctgca 9000
atggcactgg aacccccaag cccgaggaat cggcgtgacg gtcgcaaacc atccggcccg 9060
gtacaaatcg gcgcggcgct gggtgatgac ctggtggaga agttgaaggc cgcgcaggcc 9120

-continued

```
gcccagcggc aacgcatcga ggcagaagca cgccccggtg aatcgtggca agcggccgct   9180

gatcgaatcc gcaaagaatc ccggcaaccg ccggcagccg gtgcgccgtc gattaggaag   9240

ccgcccaagg gcgacgagca accagatttt ttcgttccga tgctctatga cgtgggcacc   9300

cgcgatagtc gcagcatcat ggacgtggcc gttttccgtc tgtcgaagcg tgaccgacga   9360

gctggcgagg tgatccgcta cgagcttcca gacgggcacg tagaggtttc cgcagggccg   9420

gccggcatgg ccagtgtgtg ggattacgac ctggtactga tggcggtttc ccatctaacc   9480

gaatccatga accgataccg ggaagggaag ggagacaagc ccggccgcgt gttccgtcca   9540

cacgttgcgg acgtactcaa gttctgccgg cgagccgatg gcggaaagca gaaagacgac   9600

ctggtagaaa cctgcattcg gttaaacacc acgcacgttg ccatgcagcg tacgaagaag   9660

gccaagaacg gccgcctggt gacggtatcc gagggtgaag ccttgattag ccgctacaag   9720

atcgtaaaga gcgaaaccgg gcggccggag tacatcgaga tcgagctagc tgattggatg   9780

taccgcgaga tcacagaagg caagaacccg gacgtgctga cggttcaccc cgattacttt   9840

ttgatcgatc ccggcatcgg ccgttttctc taccgcctgg cacgccgcgc cgcaggcaag   9900

gcagaagcca gatggttgtt caagacgatc tacgaacgca gtggcagcgc cggagagttc   9960

aagaagttct gtttcaccgt gcgcaagctg atcgggtcaa atgacctgcc ggagtacgat  10020

ttgaaggagg aggcggggca ggctggcccg atcctagtca tgcgctaccg caacctgatc  10080

gagggcgaag catccgccgg ttcctaatgt acggagcaga tgctagggca aattgcccta  10140

gcaggggaaa aaggtcgaaa aggtctcttt cctgtggata gcacgtacat tgggaaccca  10200

aagccgtaca ttgggaaccg gaacccgtac attgggaacc caaagccgta cattgggaac  10260

cggtcacaca tgtaagtgac tgatataaaa gagaaaaaag gcgatttttc cgcctaaaac  10320

tctttaaaac ttattaaaac tcttaaaacc cgcctggcct gtgcataact gtctggccag  10380

cgcacagccg aagagctgca aaaagcgcct acccttcggt cgctgcgctc cctacgcccc  10440

gccgcttcgc gtcggcctat cgcggccgct ggccgctcaa aaatggctgg cctacggcca  10500

ggcaatctac cagggcgcgg acaagccgcg ccgtcgccac tcgaccgccg gcgcccacat  10560

caaggcaccc tgcctcgcgc gtttcggtga tgacggtgaa aacctctgac acatgcagct  10620

cccggagacg gtcacagctt gtctgtaagc ggatgccggg agcagacaag cccgtcaggg  10680

cgcgtcagcg ggtgttggcg ggtgtcgggg cgcagccatg acccagtcac gtagcgatag  10740

cggagtgtat actggcttaa ctatgcggca tcagagcaga ttgtactgag agtgcaccat  10800

atgcggtgtg aaataccgca cagatgcgta aggagaaaat accgcatcag gcgctcttcc  10860

gcttcctcgc tcactgactc gctgcgctcg gtcgttcggc tgcggcgagc ggtatcagct  10920

cactcaaagg cggtaatacg gttatccaca gaatcagggg ataacgcagg aaagaacatg  10980

tgagcaaaag gccagcaaaa ggccaggaac cgtaaaaagg ccgcgttgct ggcgtttttc  11040

cataggctcc gcccccctga cgagcatcac aaaaatcgac gctcaagtca gaggtggcga  11100

aacccgacag gactataaag ataccaggcg tttccccctg gaagctccct cgtgcgctct  11160

cctgttccga ccctgccgct taccggatac ctgtccgcct ttctcccttc gggaagcgtg  11220

gcgctttctc atagctcacg ctgtaggtat ctcagttcgg tgtaggtcgt tcgctccaag  11280

ctgggctgtg tgcacgaacc ccccgttcag cccgaccgct gcgccttatc cggtaactat  11340

cgtcttgagt ccaacccggt aagacacgac ttatcgccac tggcagcagc cactggtaac  11400

aggattagca gagcgaggta tgtaggcgg                                    11429
```

<210> SEQ ID NO 5
<211> LENGTH: 11614
<212> TYPE: DNA
<213> ORGANISM: Artificial Sequence
<220> FEATURE:
<223> OTHER INFORMATION: Plasmid pIPG1159

<400> SEQUENCE: 5
tgctacagag ttcttgaagt ggtggcctaa ctacggctac actagaagga cagtatttgg 60
tatctgcgct ctgctgaagc cagttacctt cggaaaaaga gttggtagct cttgatccgg 120
caaacaaacc accgctggta gcggtggttt ttttgtttgc aagcagcaga ttacgcgcag 180
aaaaaaagga tctcaagaag atcctttgat cttttctacg gggtctgacg ctcagtggaa 240
cgaaaactca cgttaaggga ttttggtcat gcatgatata tctcccaatt tgtgtagggc 300
ttattatgca cgcttaaaaa taataaaagc agacttgacc tgatagtttg gctgtgagca 360
attatgtgct tagtgcatct aatcgcttga gttaacgccg gcgaagcggc gtcggcttga 420
acgaatttct agctagacat tatttgccga ctaccttggt gatctcgcct ttcacgtagt 480
ggacaaattc ttccaactga tctgcgcgcg aggccaagcg atcttcttct tgtccaagat 540
aagcctgtct agcttcaagt atgacgggct gatactgggc cggcaggcgc tccattgccc 600
agtcggcagc gacatccttc ggcgcgattt tgccggttac tgcgctgtac caaatgcggg 660
acaacgtaag cactacattt cgctcatcgc cagcccagtc gggcggcgag ttccatagcg 720
ttaaggtttc atttagcgcc tcaaatagat cctgttcagg aaccggatca aagagttcct 780
ccgccgctgg acctaccaag gcaacgctat gttctcttgc ttttgtcagc aagatagcca 840
gatcaatgtc gatcgtggct ggctcgaaga tacctgcaag aatgtcattg cgctgccatt 900
ctccaaattg cagttcgcgc ttagctggat aacgccacgg aatgatgtcg tcgtgcacaa 960
caatggtgac ttctacagcg cggagaatct cgctctctcc aggggaagcc gaagtttcca 1020
aaaggtcgtt gatcaaagct cgccgcgttg tttcatcaag ccttacggtc accgtaacca 1080
gcaaatcaat atcactgtgt ggcttcaggc cgccatccac tgcggagccg tacaaatgta 1140
cggccagcaa cgtcggttcg agatggcgct cgatgacgcc aactacctct gatagttgag 1200
tcgatacttc ggcgatcacc gcttccccca tgatgtttaa ctttgtttta gggcgactgc 1260
cctgctgcgt aacatcgttg ctgctccata acatcaaaca tcgacccacg gcgtaacgcg 1320
cttgctgctt ggatgcccga ggcatagact gtaccccaaa aaaacatgtc ataacaagaa 1380
gccatgaaaa ccgccactgc gccgttacca ccgctgcgtt cggtcaaggt tctggaccag 1440
ttgcgtgacg gcagttacgc tacttgcatt acagcttacg aaccgaacga ggcttatgtc 1500
cactgggttc gtgcccgaat tgatcacagg cagcaacgct ctgtcatccg cggtgatcac 1560
aggcagcaac gctctgtcat cgttacaatc aacatgctac cctccgcgag atcatccgtg 1620
tttcaaaccc ggcagcttag ttgccgttct tccgaatagc atcggtaaca tgagcaaagt 1680
ctgccgcctt acaacggctc tcccgctgac gccgtcccgg actgatgggc tgcctgtatc 1740
gagtggtgat tttgtgccga gctgccggtc ggggagctgt tggctggctg gtggcaggat 1800
atattgtggt gtaaacaaat tgacgcttag acaacttaat aacacattgc ggacgttttt 1860
aatgtactga attaacgccg aattaattcg ggggatctgg attttagtac tggattttgg 1920
ttttaggaat tagaaatttt attgatagaa gtattttaca aatacaaata catactaagg 1980
gtttcttata tgctcaacac atgagcgaaa ccctatagga accctaattc ccttatctgg 2040
gaactactca cacattatta tggagaaact cgagcttgtc gatcgactct agctagagga 2100

-continued

```
tcgatccgaa ccccagagtc ccgctcagaa gaactcgtca agaaggcgat agaaggcgat   2160
gcgctgcgaa tcgggagcgg cgataccgta aagcacgagg aagcggtcag cccattcgcc   2220
gccaagctct tcagcaatat cacgggtagc caacgctatg tcctgatagc ggtccgccac   2280
acccagccgg ccacagtcga tgaatccaga aaagcggcca ttttccacca tgatattcgg   2340
caagcaggca tcgccatggg tcacgacgag atcatcgccg tcgggcatgc gcgccttgag   2400
cctggcgaac agttcggctg gcgcgagccc ctgatgctct tcgtccagat catcctgatc   2460
gacaagaccg gcttccatcc gagtacgtgc tcgctcgatg cgatgtttcg cttggtggtc   2520
gaatgggcag gtagccggat caagcgtatg cagccgccgc attgcatcag ccatgatgga   2580
tactttctcg gcaggagcaa ggtgagatga caggagatcc tgccccggca cttcgcccaa   2640
tagcagccag tcccttcccg cttcagtgac aacgtcgagc acagctgcgc aaggaacgcc   2700
cgtcgtggcc agccacgata gccgcgctgc ctcgtcctgc agttcattca gggcaccgga   2760
caggtcggtc ttgacaaaaa gaaccgggcg cccctgcgct gacagccgga acacggcggc   2820
atcagagcag ccgattgtct gttgtgccca gtcatagccg aatagcctct ccacccaagc   2880
ggccggagaa cctgcgtgca atccatcttg ttcaatcatg cgaaacgatc cagatccggt   2940
gcagattatt tggattgaga gtgaatatga gactctaatt ggataccgag gggaatttat   3000
ggaacgtcag tggagcattt ttgacaagaa atatttgcta gctgatagtg accttaggcg   3060
acttttgaac gcgcaataat ggtttctgac gtatgtgctt agctcattaa actccagaaa   3120
cccgcggctg agtggctcct tcaatcgttg cggttctgtc agttccaaac gtaaaacggc   3180
ttgtcccgcg tcatcggcgg gggtcataac gtgactccct taattctccg ctcatgatca   3240
gattgtcgtt tcccgccttc agtttccaag cttgcaaaat agcacaccat ttatgtttat   3300
attttcaaat tatttaatac atttcaatat ttcataagtg tgattttttt tttttttgtc   3360
aatttcataa gtgtgatttg tcatttgtat taaacaattg tatcgcgcag tacaaataaa   3420
cagtgggaga ggtgaaaatg cagttataaa actgtccaat aatttactaa cacatttaaa   3480
tatctaaaaa gagtgtttca aaaaaaattc ttttgaaata agaaaagtga tagatatttt   3540
tacgctttcg tctgaaaata aaacaataat agtttattag aaaaatgtta tcaccgaaaa   3600
ttattctagt gccactcgct cggatcgaaa ttcgaaagtt atattctttc tctttaccta   3660
atataaaaat cacaagaaaa atcaatccga atatatctat caacatagta tatgccctta   3720
catattgttt ctgacttttc tctatccgaa tttctcgctt catggttttt ttttaacata   3780
ttctcattta attttcatta ctattatata actaaaagat ggaaataaaa taaagtgtct   3840
ttgagaatcg aacgtccata tcagtaagat agtttgtgtg aaggtaaaat ctaaaagatt   3900
taagttccaa aaacagaaaa taatatatta cgctaaaaaa gaagaaaata attaaataca   3960
aaacagaaaa aaataatata cgacagacac gtgtcacgaa gataccctac gctatagaca   4020
cagctctgtt ttctcttttc tatgcctcaa ggctctctta acttcactgt ctcctcttcg   4080
gataatccta tccttctctt cctataaata cctctccact cttcctcttc ctccaccact   4140
acaaccaccg caacaaccac caaaaaccct ctcaaagaaa tttctttttt ttcttacttt   4200
cttggtttgt caaaccatgg ttctggatgc cttctaacag tgagcagagg gagcctgaaa   4260
agaaggccca aaggcaaggg aaatgctggt tgtcactaga tacaaacagc cctaaacttt   4320
ttatgcatgg tgaagatgat aaagaaaaag tgaaccaaca atttccgtac cccttttttt   4380
ggatgccttt tcaaactgag gaaggggagg ttgaaaagaa ccgcgggaat tcgattgcgc   4440
gtcgacatgt tacgtcctgt agaaacccca acccgtgaaa tcaaaaaact cgacggcctg   4500
```

-continued

```
tgggcattca gtctggatcg cgaaaactgt ggaattgatc agcgttggtg ggaaagcgcg   4560
ttacaagaaa gccgggcaat tgctgtgcca ggcagtttta acgatcagtt cgccgatgca   4620
gatattcgta attatgcggg caacgtctgg tatcagcgcg aagtctttat atcgaaaggt   4680
tgggcaggcc agcgtatcgt gctgcgtttc gatgcggtca ctcattacgg caaagtgtgg   4740
gtcaataatc aggaagtgat ggagcatcag ggcggctata cgccatttga agccgatgtc   4800
acgccgtatg ttattgccgg gaaaagtgta cgtatcaccg tttgtgtgaa caacgaactg   4860
aactggcaga ctatcccgcc gggaatggtg attaccgacg aaaacggcaa gaaaaagcag   4920
tcttacttcc atgatttctt taactatgcc ggaatccatc gcagcgtaat gctctacacc   4980
acgccgaaca cctgggtgga cgatatcacc gtggtgacgc atgtcgcgca agactgtaac   5040
cacgcgtctg ttgactggca ggtggtggcc aatggtgatg tcagcgttga actgcgtgat   5100
gcgggatcaa caggtggttg caactggaca aggcactagc gggactttgc aagtggtgaa   5160
tccgcacctc tggcaaccgg gtgaaggtta tctctatgaa ctgtgcgtca cagccaaaag   5220
ccagacagag tgtgatatct acccgcttcg cgtcggcatc cggtcagtgg cagtgaaggg   5280
cgaacagttc ctgattaacc acaaaccgtt ctactttact ggctttggtc gtcatgaaga   5340
tgcggacttg cgtggcaaaa ggattcgata acgtgctgat ggtgcacgac cacgcattaa   5400
tggactggat tggggccaac tcctaccgta cctcgcatta cccttacgct gaagagatgc   5460
tcgactgggc agatgaacat ggcatcgtgg tgattgatga aactgctgct gtcggcttta   5520
acctctcttt aggcattggt ttcgaagcgg gcaacaagcc gaaagaactg tacagcgaag   5580
aggcagtcaa cggggaaact cagcaagcgc acttacaggc gattaaagag ctgatagcgc   5640
gtgacaaaaa ccacccaagc gtggtgatgt ggagtattgc caacgaaccg gatacccgtc   5700
cgcaaggtgc acgggaatat ttcgcgccac tggcggaagc aacgcgtaaa ctcgacccga   5760
cgcgtccgat cacctgcgtc aatgtaatgt tctgcgacgc tcacaccgat accatcagcg   5820
atctctttga tgtgctgtgc ctgaaccgtt attacggatg gtatgtccaa agcggcgatt   5880
tggaaacggc agagaaggta ctggaaaaag aacttctggc ctggcaggag aaactgcatc   5940
agccgattat catcaccgaa tacggcgtgg atacgttagc cgggctgcac tcaatgtaca   6000
ccgacatgtg gagtgaagag tatcagtgtg catggctgga tatgtatcac cgcgtctttg   6060
atcgcgtcag cgccgtcgtc ggtgaacagg tatggaattt cgccgatttt gcgacctcgc   6120
aaggcatatt gcgcgttggc ggtaacaaga aagggatctt cactcgcgac cgcaaaccga   6180
agtcggcggc ttttctgctg caaaaacgct ggactggcat gaacttcggt gaaaaaccgc   6240
agcagggagg caaacaagct agccaccacc accaccacca cgtgtgactc gagttctttt   6300
caacctcccc ttcctcagtt tgaaaaggca tccaaaaaaa ggggtacgga aattgttggt   6360
tcactttttc tttatcatct tcaccatgca taaaaagttt agggctgttt gtatctagtg   6420
acaaccagca tttcccttgc ctttgggcct tcttttcagg ctccctctgc tcactgttag   6480
aaggcatcca gaaactagtg ttaacgctag ccaccaccac caccaccacg tgtgaattac   6540
aggtgaccag ctcgaatttc cccgatcgtt caaacatttg gcaataaagt ttcttaagat   6600
tgaatcctgt tgccggtctt gcgatgatta tcatataatt tctgttgaat tacgttaagc   6660
atgtaataat taacatgtaa tgcatgacgt tatttatgag atgggttttt atgattagag   6720
tcccgcaatt atacatttaa tacgcgatag aaaacaaaat atagcgcgca aactaggata   6780
aattatcgcg cgcggtgtca tctatgttac tagatcggga attaaactat cagtgtttga   6840
```

-continued

```
caggatatat tggcgggtaa acctaagaga aaagagcgtt tattagaata acggatattt   6900
aaaagggcgt gaaaaggttt atccgttcgt ccatttgtat gtgcatgcca accacagggt   6960
tcccctcggg atcaaagtac tttgatccaa cccctccgct gctatagtgc agtcggcttc   7020
tgacgttcag tgcagccgtc ttctgaaaac gacatgtcgc acaagtccta agttacgcga   7080
caggctgccg ccctgccctt ttcctggcgt tttcttgtcg cgtgttttag tcgcataaag   7140
tagaatactt gcgactagaa ccggagacat tacgccatga acaagagcgc cgccgctggc   7200
ctgctgggct atgcccgcgt cagcaccgac gaccaggact tgaccaacca acgggccgaa   7260
ctgcacgcgg ccggctgcac caagctgttt tccgagaaga tcaccggcac caggcgcgac   7320
cgcccggagc tggccaggat gcttgaccac ctacgccctg gcgacgttgt gacagtgacc   7380
aggctagacc gcctggcccg cagcacccgc gacctactgg acattgccga gcgcatccag   7440
gaggccggcg cgggcctgcg tagcctggca gagccgtggg ccgacaccac cacgccggcc   7500
ggccgcatgg tgttgaccgt gttcgccggc attgccgagt tcgagcgttc cctaatcatc   7560
gaccgcaccc ggagcgggcg cgaggccgcc aaggcccgag gcgtgaagtt tggcccccgc   7620
cctaccctca ccccggcaca gatcgcgcac gcccgcgagc tgatcgacca ggaaggccgc   7680
accgtgaaag aggcggctgc actgcttggc gtgcatcgct cgaccctgta ccgcgcactt   7740
gagcgcagcg aggaagtgac gcccaccgag gccaggcggc gcggtgcctt ccgtgaggac   7800
gcattgaccg aggccgacgc cctggcggcc gccgagaatg aacgccaaga ggaacaagca   7860
tgaaaccgca ccaggacggc caggacgaac cgtttttcat taccgaagag atcgaggcgg   7920
agatgatcgc ggccgggtac gtgttcgagc cgcccgcgca cgtctcaacc gtgcggctgc   7980
atgaaatcct ggccggtttg tctgatgcca agctggcggc ctggccggcc agcttggccg   8040
ctgaagaaac cgagcgccgc cgtctaaaaa ggtgatgtgt atttgagtaa aacagcttgc   8100
gtcatgcggt cgctgcgtat atgatgcgat gagtaaataa acaaatacgc aaggggaacg   8160
catgaaggtt atcgctgtac ttaaccagaa aggcgggtca ggcaagacga ccatcgcaac   8220
ccatctagcc cgcgccctgc aactcgccgg ggccgatgtt ctgttagtcg attccgatcc   8280
ccagggcagt gcccgcgatt gggcggccgt gcgggaagat caaccgctaa ccgttgtcgg   8340
catcgaccgc ccgacgattg accgcgacgt gaaggccatc ggccggcgcg acttcgtagt   8400
gatcgacgga gcgccccagg cggcggactt ggctgtgtcc gcgatcaagg cagccgactt   8460
cgtgctgatt ccggtgcagc caagccctta cgacatatgg gccaccgccg acctggtgga   8520
gctggttaag cagcgcattg aggtcacgga tggaaggcta caagcggcct ttgtcgtgtc   8580
gcgggcgatc aaaggcacgc gcatcggcgg tgaggttgcc gaggcgctgg ccgggtacga   8640
gctgcccatt cttgagtccc gtatcacgca gcgcgtgagc tacccaggca ctgccgccgc   8700
cggcacaacc gttcttgaat cagaacccga gggcgacgct gcccgcgagg tccaggcgct   8760
ggccgctgaa attaaatcaa aactcatttg agttaatgag gtaaagagaa aatgagcaaa   8820
agcacaaaca cgctaagtgc cggccgtccg agcgcacgca gcagcaaggc tgcaacgttg   8880
gccagcctgg cagacacgcc agccatgaag cgggtcaact ttcagttgcc ggcggaggat   8940
cacaccaagc tgaagatgta cgcggtacgc caaggcaaga ccattaccga gctgctatct   9000
gaatacatcg cgcagctacc agagtaaatg agcaaatgaa taaatgagta gatgaatttt   9060
agcggctaaa ggaggcggca tggaaaatca agaacaacca ggcaccgacg ccgtggaatg   9120
ccccatgtgt ggaggaacgg gcggttggcc aggcgtaagc ggctgggttg tctgccggcc   9180
ctgcaatggc actggaaccc ccaagcccga ggaatcggcg tgacggtcgc aaaccatccg   9240
```

-continued

```
gcccggtaca aatcggcgcg gcgctgggtg atgacctggt ggagaagttg aaggccgcgc   9300
aggccgccca gcggcaacgc atcgaggcag aagcacgccc cggtgaatcg tggcaagcgg   9360
ccgctgatcg aatccgcaaa gaatcccggc aaccgccggc agccggtgcg ccgtcgatta   9420
ggaagccgcc caagggcgac gagcaaccag atttttttcgt tccgatgctc tatgacgtgg   9480
gcacccgcga tagtcgcagc atcatggacg tggccgtttt ccgtctgtcg aagcgtgacc   9540
gacgagctgg cgaggtgatc cgctacgagc ttccagacgg gcacgtagag gtttccgcag   9600
ggccggccgg catggccagt gtgtgggatt acgacctggt actgatggcg gtttcccatc   9660
taaccgaatc catgaaccga taccgggaag ggaagggaga caagcccggc cgcgtgttcc   9720
gtccacacgt tgcggacgta ctcaagttct gccggcgagc cgatggcgga aagcagaaag   9780
acgacctggt agaaacctgc attcggttaa acaccacgca cgttgccatg cagcgtacga   9840
agaaggccaa gaacggccgc ctggtgacgg tatccgaggg tgaagccttg attagccgct   9900
acaagatcgt aaagagcgaa accgggcggc cggagtacat cgagatcgag ctagctgatt   9960
ggatgtaccg cgagatcaca gaaggcaaga acccggacgt gctgacggtt caccccgatt  10020
actttttgat cgatcccggc atcggccgtt ttctctaccg cctggcacgc cgcgccgcag  10080
gcaaggcaga agccagatgg ttgttcaaga cgatctacga acgcagtggc agcgccggag  10140
agttcaagaa gttctgtttc accgtgcgca agctgatcgg gtcaaatgac ctgccggagt  10200
acgatttgaa ggaggaggcg gggcaggctg gcccgatcct agtcatgcgc taccgcaacc  10260
tgatcgaggg cgaagcatcc gccggttcct aatgtacgga gcagatgcta gggcaaattg  10320
ccctagcagg ggaaaaaggt cgaaaaggtc tctttcctgt ggatagcacg tacattggga  10380
acccaaagcc gtacattggg aaccggaacc cgtacattgg gaacccaaag ccgtacattg  10440
ggaaccggtc acacatgtaa gtgactgata taaaagagaa aaaaggcgat ttttccgcct  10500
aaaactcttt aaaacttatt aaaactctta aaacccgcct ggcctgtgca taactgtctg  10560
gccagcgcac agccgaagag ctgcaaaaag cgcctaccct tcggtcgctg cgctccctac  10620
gccccgccgc ttcgcgtcgg cctatcgcgg ccgctggccg ctcaaaaatg gctggcctac  10680
ggccaggcaa tctaccaggg cgcggacaag ccgcgccgtc gccactcgac cgccggcgcc  10740
cacatcaagg caccctgcct cgcgcgtttc ggtgatgacg gtgaaaacct ctgacacatg  10800
cagctcccgg agacggtcac agcttgtctg taagcggatg ccgggagcag acaagcccgt  10860
cagggcgcgt cagcgggtgt tggcgggtgt cggggcgcag ccatgaccca gtcacgtagc  10920
gatagcggag tgtatactgg cttaactatg cggcatcaga gcagattgta ctgagagtgc  10980
accatatgcg gtgtgaaata ccgcacagat gcgtaaggag aaaataccgc atcaggcgct  11040
cttccgcttc ctcgctcact gactcgctgc gctcggtcgt tcggctgcgg cgagcggtat  11100
cagctcactc aaaggcggta atacggttat ccacagaatc aggggataac gcaggaaaga  11160
acatgtgagc aaaaggccag caaaaggcca ggaaccgtaa aaaggccgcg ttgctggcgt  11220
ttttccatag gctccgcccc cctgacgagc atcacaaaaa tcgacgctca agtcagaggt  11280
ggcgaaaccc gacaggacta taaagatacc aggcgtttcc ccctggaagc tccctcgtgc  11340
gctctcctgt tccgaccctg ccgcttaccg gatacctgtc cgcctttctc ccttcgggaa  11400
gcgtggcgct ttctcatagc tcacgctgta ggtatctcag ttcggtgtag gtcgttcgct  11460
ccaagctggg ctgtgtgcac gaaccccccg ttcagcccga ccgctgcgcc ttatccggta  11520
actatcgtct tgagtccaac ccggtaagac acgacttatc gccactggca gcagccactg  11580
```

-continued gtaacaggat tagcagagcg aggtatgtag gcgg 11614

<210> SEQ ID NO 6
<211> LENGTH: 9468
<212> TYPE: DNA
<213> ORGANISM: Artificial Sequence
<220> FEATURE:
<223> OTHER INFORMATION: Plasmid pIPG1174

<400> SEQUENCE: 6
gttaacgcta gccaccacca ccaccaccac gtgtgaatta caggtgacca gctcgaattt 60
ccccgatcgt tcaaacattt ggcaataaag tttcttaaga ttgaatcctg ttgccggtct 120
tgcgatgatt atcatataat ttctgttgaa ttacgttaag catgtaataa ttaacatgta 180
atgcatgacg ttatttatga gatgggtttt tatgattaga gtcccgcaat tatacattta 240
atacgcgata gaaaacaaaa tatagcgcgc aaactaggat aaattatcgc gcgcggtgtc 300
atctatgtta ctagatcggg aattaaacta tcagtgtttg acaggatata ttggcgggta 360
aacctaagag aaaagagcgt ttattagaat aacggatatt taaaagggcg tgaaaaggtt 420
tatccgttcg tccatttgta tgtgcatgcc aaccacaggg ttcccctcgg gatcaaagta 480
ctttgatcca acccctccgc tgctatagtg cagtcggctt ctgacgttca gtgcagccgt 540
cttctgaaaa cgacatgtcg cacaagtcct aagttacgcg acaggctgcc gccctgccct 600
tttcctggcg ttttcttgtc gcgtgtttta gtcgcataaa gtagaatact tgcgactaga 660
accggagaca ttacgccatg aacaagagcg ccgccgctgg cctgctgggc tatgcccgcg 720
tcagcaccga cgaccaggac ttgaccaacc aacgggccga actgcacgcg gccggctgca 780
ccaagctgtt ttccgagaag atcaccggca ccaggcgcga ccgcccggag ctggccagga 840
tgcttgacca cctacgccct ggcgacgttg tgacagtgac caggctagac cgcctggccc 900
gcagcacccg cgacctactg gacattgccg agcgcatcca ggaggccggc gcgggcctgc 960
gtagcctggc agagccgtgg gccgacacca ccacgccggc cggccgcatg gtgttgaccg 1020
tgttcgccgg cattgccgag ttcgagcgtt ccctaatcat cgaccgcacc cggagcgggc 1080
gcgaggccgc caaggcccga ggcgtgaagt ttggcccccg ccctaccctc accccggcac 1140
agatcgcgca cgcccgcgag ctgatcgacc aggaaggccg caccgtgaaa gaggcggctg 1200
cactgcttgg cgtgcatcgc tcgaccctgt accgcgcact tgagcgcagc gaggaagtga 1260
cgcccaccga ggccaggcgg cgcggtgcct tccgtgagga cgcattgacc gaggccgacg 1320
ccctggcggc cgccgagaat gaacgccaag aggaacaagc atgaaaccgc accaggacgg 1380
ccaggacgaa ccgtttttca ttaccgaaga gatcgaggcg gagatgatcg cggccgggta 1440
cgtgttcgag ccgcccgcgc acgtctcaac cgtgcggctg catgaaatcc tggccggttt 1500
gtctgatgcc aagctggcgg cctggccggc cagcttggcc gctgaagaaa ccgagcgccg 1560
ccgtctaaaa aggtgatgtg tatttgagta aaacagcttg cgtcatgcgg tcgctgcgta 1620
tatgatgcga tgagtaaata aacaaatacg caaggggaac gcatgaaggt tatcgctgta 1680
cttaaccaga aaggcgggtc aggcaagacg accatcgcaa cccatctagc ccgcgccctg 1740
caactcgccg gggccgatgt tctgttagtc gattccgatc cccagggcag tgcccgcgat 1800
tgggcggccg tgcgggaaga tcaaccgcta accgttgtcg gcatcgaccg cccgacgatt 1860
gaccgcgacg tgaaggccat cggccggcgc gacttcgtag tgatcgacgg agcgccccag 1920
gcggcggact tggctgtgtc cgcgatcaag gcagccgact tcgtgctgat tccggtgcag 1980
ccaagccctt acgacatatg ggccaccgcc gacctggtgg agctggttaa gcagcgcatt 2040

-continued

```
gaggtcacgg atggaaggct acaagcggcc tttgtcgtgt cgcgggcgat caaaggcacg   2100
cgcatcggcg gtgaggttgc cgaggcgctg gccgggtacg agctgcccat tcttgagtcc   2160
cgtatcacgc agcgcgtgag ctacccaggc actgccgccg ccggcacaac cgttcttgaa   2220
tcagaacccg agggcgacgc tgcccgcgag gtccaggcgc tggccgctga aattaaatca   2280
aaactcattt gagttaatga ggtaaagaga aaatgagcaa aagcacaaac acgctaagtg   2340
ccggccgtcc gagcgcacgc agcagcaagg ctgcaacgtt ggccagcctg gcagacacgc   2400
cagccatgaa gcgggtcaac tttcagttgc cggcggagga tcacaccaag ctgaagatgt   2460
acgcggtacg ccaaggcaag accattaccg agctgctatc tgaatacatc gcgcagctac   2520
cagagtaaat gagcaaatga ataaatgagt agatgaattt tagcggctaa aggaggcggc   2580
atggaaaatc aagaacaacc aggcaccgac gccgtggaat gccccatgtg tggaggaacg   2640
ggcggttggc caggcgtaag cggctgggtt gtctgccggc cctgcaatgg cactggaacc   2700
cccaagcccg aggaatcggc gtgacggtcg caaaccatcc ggcccggtac aaatcggcgc   2760
ggcgctgggt gatgacctgg tggagaagtt gaaggccgcg caggccgccc agcggcaacg   2820
catcgaggca gaagcacgcc ccggtgaatc gtggcaagcg gccgctgatc gaatccgcaa   2880
agaatcccgg caaccgccgg cagccggtgc gccgtcgatt aggaagccgc ccaagggcga   2940
cgagcaacca gattttttcg ttccgatgct ctatgacgtg ggcacccgcg atagtcgcag   3000
catcatggac gtggccgttt tccgtctgtc gaagcgtgac cgacgagctg gcgaggtgat   3060
ccgctacgag cttccagacg ggcacgtaga ggtttccgca gggccggccg gcatggccag   3120
tgtgtgggat tacgacctgg tactgatggc ggtttcccat ctaaccgaat ccatgaaccg   3180
ataccgggaa gggaagggag acaagcccgg ccgcgtgttc cgtccacacg ttgcggacgt   3240
actcaagttc tgccggcgag ccgatggcgg aaagcagaaa gacgacctgg tagaaacctg   3300
cattcggtta aacaccacgc acgttgccat gcagcgtacg aagaaggcca agaacggccg   3360
cctggtgacg gtatccgagg gtgaagcctt gattagccgc tacaagatcg taaagagcga   3420
aaccgggcgg ccggagtaca tcgagatcga gctagctgat tggatgtacc gcgagatcac   3480
agaaggcaag aacccggacg tgctgacggt tcaccccgat tactttttga tcgatcccgg   3540
catcggccgt tttctctacc gcctggcacg ccgcgccgca ggcaaggcag aagccagatg   3600
gttgttcaag acgatctacg aacgcagtgg cagcgccgga gagttcaaga agttctgttt   3660
caccgtgcgc aagctgatcg ggtcaaatga cctgccggag tacgatttga aggaggaggc   3720
ggggcaggct ggcccgatcc tagtcatgcg ctaccgcaac ctgatcgagg gcgaagcatc   3780
cgccggttcc taatgtacgg agcagatgct agggcaaatt gccctagcag gggaaaaagg   3840
tcgaaaaggt ctctttcctg tggatagcac gtacattggg aacccaaagc cgtacattgg   3900
gaaccggaac ccgtacattg ggaacccaaa gccgtacatt gggaaccggt cacacatgta   3960
agtgactgat ataaaagaga aaaaaggcga tttttccgcc taaaactctt taaaacttat   4020
taaaactctt aaaacccgcc tggcctgtgc ataactgtct ggccagcgca cagccgaaga   4080
gctgcaaaaa gcgcctaccc ttcggtcgct gcgctcccta cgccccgccg cttcgcgtcg   4140
gcctatcgcg gccgctggcc gctcaaaaat ggctggccta cggccaggca atctaccagg   4200
gcgcggacaa gccgcgccgt cgccactcga ccgccggcgc ccacatcaag gcaccctgcc   4260
tcgcgcgttt cggtgatgac ggtgaaaacc tctgacacat gcagctcccg gagacggtca   4320
cagcttgtct gtaagcggat gccgggagca gacaagcccg tcagggcgcg tcagcgggtg   4380
```

-continued ttggcgggtg tcggggcgca gccatgaccc agtcacgtag cgatagcgga gtgtatactg 4440
gcttaactat gcggcatcag agcagattgt actgagagtg caccatatgc ggtgtgaaat 4500
accgcacaga tgcgtaagga gaaaataccg catcaggcgc tcttccgctt cctcgctcac 4560
tgactcgctg cgctcggtcg ttcggctgcg gcgagcggta tcagctcact caaaggcggt 4620
aatacggtta tccacagaat caggggataa cgcaggaaag aacatgtgag caaaaggcca 4680
gcaaaaggcc aggaaccgta aaaaggccgc gttgctggcg tttttccata ggctccgccc 4740
ccctgacgag catcacaaaa atcgacgctc aagtcagagg tggcgaaacc cgacaggact 4800
ataaagatac caggcgtttc cccctggaag ctccctcgtg cgctctcctg ttccgaccct 4860
gccgcttacc ggatacctgt ccgcctttct cccttcggga agcgtggcgc tttctcatag 4920
ctcacgctgt aggtatctca gttcggtgta ggtcgttcgc tccaagctgg gctgtgtgca 4980
cgaacccccc gttcagcccg accgctgcgc cttatccggt aactatcgtc ttgagtccaa 5040
cccggtaaga cacgacttat cgccactggc agcagccact ggtaacagga ttagcagagc 5100
gaggtatgta ggcggtgcta cagagttctt gaagtggtgg cctaactacg gctacactag 5160
aaggacagta tttggtatct gcgctctgct gaagccagtt accttcggaa aaagagttgg 5220
tagctcttga tccggcaaac aaaccaccgc tggtagcggt ggtttttttg tttgcaagca 5280
gcagattacg cgcagaaaaa aaggatctca agaagatcct ttgatctttt ctacggggtc 5340
tgacgctcag tggaacgaaa actcacgtta agggattttg gtcatgcatt ctaggtacta 5400
aaacaattca tccagtaaaa tataatattt tattttctcc caatcaggct tgatccccag 5460
taagtcaaaa aatagctcga catactgttc ttccccgata tcctccctga tcgaccggac 5520
gcagaaggca atgtcatacc acttgtccgc cctgccgctt ctcccaagat caataaagcc 5580
acttactttg ccatctttca caaagatgtt gctgtctccc aggtcgccgt gggaaaagac 5640
aagttcctct tcgggctttt ccgtctttaa aaaatcatac agctcgcgcg gatctttaaa 5700
tggagtgtct tcttcccagt tttcgcaatc cacatcggcc agatcgttat tcagtaagta 5760
atccaattcg gctaagcggc tgtctaagct attcgtatag ggacaatccg atatgtcgat 5820
ggagtgaaag agcctgatgc actccgcata cagctcgata atcttttcag ggctttgttc 5880
atcttcatac tcttccgagc aaaggacgcc atcggcctca ctcatgagca gattgctcca 5940
gccatcatgc cgttcaaagt gcaggacctt tggaacaggc agctttcctt ccagccatag 6000
catcatgtcc ttttcccgtt ccacatcata ggtggtccct ttataccggc tgtccgtcat 6060
ttttaaatat aggttttcat ttctcccac cagcttatat accttagcag gagacattcc 6120
ttccgtatct tttacgcagc ggtatttttc gatcagtttt ttcaattccg gtgatattct 6180
cattttagcc atttattatt tccttcctct tttctacagt atttaaagat accccaagaa 6240
gctaattata acaagacgaa ctccaattca ctgttccttg cattctaaaa ccttaaatac 6300
cagaaaacag ctttttcaaa gttgttttca aagttggcgt ataacatagt atcgacggag 6360
ccgattttga aaccgcggtg atcacaggca gcaacgctct gtcatcgtta caatcaacat 6420
gctaccctcc gcgagatcat ccgtgtttca aacccggcag cttagttgcc gttcttccga 6480
atagcatcgg taacatgagc aaagtctgcc gccttacaac ggctctcccg ctgacgccgt 6540
cccggactga tgggctgcct gtatcgagtg gtgattttgt gccgagctgc cggtcgggga 6600
gctgttggct ggctggtggc aggatatatt gtggtgtaaa caaattgacg cttagacaac 6660
ttaataacac attgcggacg tttttaatgt actgaattaa cgccgaatta attcggggga 6720
tctggatttt agtactggat tttggtttta ggaattagaa attttattga tagaagtatt 6780

-continued ttacaaatac aaatacatac taagggtttc ttatatgctc aacacatgag cgaaacccta 6840
taggaaccct aattccctta tctgggaact actcacacat tattatggag aaactcgagc 6900
ttgtcgatcg actctagcta gaggatcgat ccgaacccca gagtcccgct cagaagaact 6960
cgtcaagaag gcgatagaag gcgatgcgct gcgaatcggg agcggcgata ccgtaaagca 7020
cgaggaagcg gtcagcccat tcgccgccaa gctcttcagc aatatcacgg gtagccaacg 7080
ctatgtcctg atagcggtcc gccacaccca gccggccaca gtcgatgaat ccagaaaagc 7140
ggccattttc caccatgata ttcggcaagc aggcatcgca atgggtcacg acgagatcat 7200
cgccgtcggg catgcgcgcc ttgagcctgg cgaacagttc ggctggcgcg agcccctgat 7260
gctcttcgtc cagatcatcc tgatcgacaa gaccggcttc catccgagta cgtgctcgct 7320
cgatgcgatg tttcgcttgg tggtcgaatg ggcaggtagc cggatcaagc gtatgcagcc 7380
gccgcattgc atcagccatg atggatactt tctcggcagg agcaaggtga gatgacagga 7440
gatcctgccc cggcacttcg cccaatagca gccagtccct tcccgcttca gtgacaacgt 7500
cgagcacagc tgcgcaagga acgcccgtcg tggccagcca cgatagccgc gctgcctcgt 7560
cctgcagttc attcagggca ccggacaggt cggtcttgac aaaaagaacc gggcgcccct 7620
gcgctgacag ccggaacacg gcggcatcag agcagccgat tgtctgttgt gcccagtcat 7680
agccgaatag cctctccacc caagcggccg gagaacctgc gtgcaatcca tcttgttcaa 7740
tcatgcgaaa cgatccagat ccggtgcaga ttatttggat tgagagtgaa tatgagactc 7800
taattggata ccgaggggaa tttatggaac gtcagtggag cattttttgac aagaaatatt 7860 tgctagctga tagtgacctt aggcgacttt tgaacgcgca ataatggttt ctgacgtatg 7920
tgcttagctc attaaactcc agaaacccgc ggctgagtgg ctccttcaat cgttgcggtt 7980
ctgtcagttc caaacgtaaa acggcttgtc ccgcgtcatc ggcgggggtc ataacgtgac 8040
tcccttaatt ctccgctcat gatcagattg tcgtttcccg ccttcagttt ccaagcttgg 8100
cactggccgt cgttttacaa cgtcgtgact gggaaaaccc tggcgttacc caacttaatc 8160
gccttgcagc acatccccct ttcgccagct ggcgtaatag cgaagaggcc cgcaccgatc 8220
gcccttccca acagttgcgc agcctgaatg gcgaatgcta gagcagcttg agcttggatc 8280
agattgtcgt ttcccgcctt cagtttagct tcatggagtc aaagattcaa atagaggacc 8340
taacagaact cgccgtaaag actggcgaac agttcataca gagtctctta cgactcaatg 8400
acaagaagaa aatcttcgtc aacatggtgg agcacgacac acttgtctac tccaaaaata 8460
tcaaagatac agtctcagaa gaccaaaggg caattgagac ttttcaacaa agggtaatat 8520
ccggaaacct cctcggattc cattgcccag ctatctgtca ctttattgtg aagatagtgg 8580
aaaaggaagg tggctcctac aaatgccatc attgcgataa aggaaaggcc atcgttgaag 8640
atgcctctgc cgacagtggt cccaaagatg gacccccacc cacgaggagc atcgtggaaa 8700
aagaagacgt tccaaccacg tcttcaaagc aagtggattg atgtgatatc tccactgacg 8760
taagggatga cgcacaatcc cactatcctt cgcaagaccc ttcctctata taaggaagtt 8820
catttcattt ggagagaaca cgggggactc ttgaccatgg ttctggatgc cttctaacag 8880
tgagcagagg gagcctgaaa agaaggccca aaggcaaggg aaatgctggt tgtcactaga 8940
tacaaacagc cctaaacttt ttatgcatgg tgaagatgat aaagaaaaag tgaaccaaca 9000
atttccgtac ccctttttt ggatgccttt tcaaactgag gaaggggagg ttgaaaagaa 9060
ccgcggctgc aggtaaattt ctagtttttc tccttcattt tcttggttag gacccttttc 9120

```
tctttttatt tttttgagct tcgatctgtt tttaaactga tctatttttt aattgattgg   9180

ttatggtgta aatattacat agctttaact gataatctga ttactttatt tcgtgtgtaa   9240

ttgattaatt ctgcagctcg agttcttttc aacctcccct tcctcagttt gaaaaggcat   9300

ccaaaaaaag gggtacggaa attgttggtt cactttttct ttatcatctt caccatgcat   9360

aaaaagttta gggctgtttg tatctagtga caaccagcat ttcccttgcc tttgggcctt   9420

cttttcaggc tccctctgct cactgttaga aggcatccag aaactagt                9468
```

<210> SEQ ID NO 7
<211> LENGTH: 104
<212> TYPE: DNA
<213> ORGANISM: Arabidopsis thaliana

<400> SEQUENCE: 7

```
gatgtctata aatataagag accctcttat agtaagcaga gttgttggag acgttcttga     60

tccgtttaat agatcaatca ctctaaaggt tacttatggc caaa                     104
```

<210> SEQ ID NO 8
<211> LENGTH: 1766
<212> TYPE: DNA
<213> ORGANISM: Citrus clementina

<400> SEQUENCE: 8

```
aaaacgtaac atgtatccct caaatatctt tcctatcggg tctggccctg aaacttctcg     60

aactttcaag cagaggaaaa tcaatttcta tatatgatcc cacaaacccc taacattttc    120

tattgtaaac gcaattacag aaaccttaaa aaacagtttc agaaagaata ttttccgacg    180

atacgatgga taatctgccc cacgggagaa gttaccggag cataccgtct cgcggtcggc    240

cgcgctcttc ctacgcgccg agcgtgagag agattccggt ccagtacgtc ggctcggagg    300

agaagcagtc gagggaatcc aattcggcgg tgaagatcca gaaggttttc agagcattcc    360

tggtgaggaa aagcgtgaag aagatcaagg agataagagg cgaagtggag gagatcgaga    420

agcggatctc gacgggggat actattgatt tgattgcgag ggattcacaa gagagattga    480

aattgaatga gatgttgatg agtttgcttt tcaggttgga ttctgttaga ggcgttgatt    540

ctggagttag ggattgcaga aaggcggtta ttaagaaggc gattgcgttg caagaatttc    600

tggatgccgc cttttcttcc aataatagca ggaacgatca gaacggtgag gatgaaaatg    660

tcgtggaagc tgttgacgag cagaatcagt cggcgcaggt ggagtgcacg gaggagaatg    720

gtgaaagaac tgacgcattt gatgaaaaag agaccgttga aaatcaaaac gaggtcggag    780

acgaagagac tgtcgaaaat caaggcgacg acggagaagc tcgggaggtt gttgaggagt    840

gcgacgatgt gatgccatcg gtgagtaatg gtccggcacc ggaagagaat gtaggaacaa    900

gtcaaagtga gagtgaagcc gattcctcgg caaatcccga agaggatgag aattcatcac    960

cgaaacaaga aaacaatgca gctggagctg gagaggtcga agagaatgtg aaagagagcg   1020

ggggcgaagg agaggtcgaa gagaatgtgc aacagagtgg gggcgaagga gcaagagacg   1080

agaactcgaa gaacaaagag ctgttggaga ggatgatgga ggatcatggg agaatgatgg   1140

aaatgatggc gcaattattt gagaggaatg aaatgcagac gaggttgttg agtgctctgt   1200

ctcatagggt tgagcagctg gagaaggctt tcatgcgtga gaggttgagg aggaagaaaa   1260

agaagaacgc tgctggcgct gctgatggtt gtgaaacgtc gcgggataac aagaaatgcg   1320

gaaagagata gtgatttgag atttgtctct caaatgtctt ttgtttaaca cgtttttatg   1380

tttgtaattt caattcaaac ttgctgttgg tggtaatggt gatttgagag attgtgtgtg   1440
```

ttaattggca atgcccgtgt gttaatctta gttattaatc attacagtca ttcaatcact 1500
cagcatcctc taaaactctc cctaatgagc gatagtgtca ttttgagcgc ttcacatcag 1560
taggggatga gaatatgggt cacgatttgt ttatttgatt ggatgtgaat taaatgggtt 1620
tgaattagaa aaaaataata tgtttaataa acgagtgaat tcgatttaat ttgttaatta 1680
aataaattaa attcgggttt gaagatatta attcgtttat ttatttatga ttcgtttaat 1740
gaatgggtta taaacgaatt gaatac 1766

<210> SEQ ID NO 9
<211> LENGTH: 497
<212> TYPE: DNA
<213> ORGANISM: Citrus sinensis

<400> SEQUENCE: 9
ccaacaattt ccgtacccct ttttttggat gccttttcaa actgaggaag gggaggttga 60
aaagaaagat cgaaaggaga agaatgttgc ttcaatatca gccgaagaat caccttctga 120
ctctaagttc atgcaggtga agcctccaga gagtgatgaa aggatgaaaa attttgagcc 180
aaacgaggat ttttctgacg ataaggctaa aagctcacaa atgatggagg gcactgctaa 240
taaaaaaact attcctgtaa ggcaagtgga aatgtgcagg gaggaccact ctgacagtgc 300
tgagaaggga gttgcagcag ataattcctt cagaaccagt aagatgagac agtcctcatc 360
tccacccaag acatcgaaat tacctcctgt ttgtctgaaa ctggaacctt tgtcaaagaa 420
gaaaaatagt aatgggaatt ccatatcccc tagtcctcca ggcctgaaaa gacagtcaga 480
cgaatacgtt cacaagc 497

<210> SEQ ID NO 10
<211> LENGTH: 4195
<212> TYPE: DNA
<213> ORGANISM: Citrus sinensis

<400> SEQUENCE: 10
actctcgtgg aagagaatac agctgattgt atctaagcta gaagaggtca tcataacagc 60
tcttatttgg gtttgtggat tgaatttgcc ccgataactg agtcatctgg actgtggaag 120
ttgttggtgg attcttcttt tcttgtctac actataaatt gtgcttttgc ttttacactt 180
cgaagtcatc cagtggttct tcgagctaca tttttaaacc ctattaagaa ctacttggag 240
ctgtttgttg aaaatgatgc cagtatacat ggactcatgc catcagcaga gaaaccaaat 300
gccttttcct cattattatc atccaagtca caataatgtt ccacctcatg tatgaatctt 360
ggcctcatgg cagcaactat ggctactcaa tgtcgtgtca tggctgctgc aaccattgta 420
acttccctgg ttgttatgca tatagacctt ccttctcttc tttctcacct gcaccgccat 480
tttttctatc gcgggcatca ccctccattc attgagccat atcctgtcca ttatgctcct 540
cctctacatc atgcaatgga gcagcagagg tatgagtatg ataaagatgc tcatagagat 600
cattattgtt gtggctgtct taatcacatg agcaaccaga gaattgacaa aggtgtaaaa 660
attgaagagc aggagcctga tgtggcaaag aagagtgatt ctgtggttcc gcttcagtca 720
aaaagttatc catacccaat tgcaaggatt tcaccagagt acatgaagaa aaatgatgag 780
cccagaaggt cttttgaatc agaggtggcg gagcaggaga aggttccatg caacacaaag 840
tccaatgaga atatggaacc ttctgagggg aagtcaagcg agtggaatgg ctggtttcca 900
ctcgacatga ataaccttaa acctttgatg cagggtgaag atgagaagag gaaacagaat 960

-continued caacaaaatg agaatggaat gaagcaattc tcgtatcctg ttttctggat gccttctaac 1020
agtgagcaaa gggagcctga aaagaaggcc caaaggcaag ggaaatgctg gttgtcacta 1080
gatacgaaca gccctaaatt tttgatgcat ggtgaagatg ataaagaaaa ggtgaaccaa 1140
caatttccgt accccttttt ttggatgcct tttcaaactg aggaagggga ggttgaaaag 1200
aaagatcgaa aggagaagaa tgttgcttca atatcagccg aagaatcacc ttctgactct 1260
aagttcatgc aggtgaagtc tccagagagt gatgaaagga tgaaaaattt tgagccaaac 1320
gaggattttt ctgacgataa ggctaaaagc tcacaaatga tggagggcac tgctaataaa 1380
aaaattattc ctgtaaggca agtggaaatg tgcagggagg accactctga cagtgctgag 1440
aagggagttg cagcagataa ttcctccaga accagtaaga tgagacagtc ctcatctcca 1500
ccgaagacgt cgaaattacc tcctgtttgt ctgagactgg aacctttgtc aaagaagaaa 1560
aatggtaatg ggaattccag atcccctagt cctccaggcc tgaaaagaca gtcagacgaa 1620
tacgttcaca agccttctgc ttcatcagta ttgaaagaga gcacgccaca gggttcccaa 1680
tctgctgatg attcctttaa aagaagggga gatgggaacc gaaagaaaac agagaaaaaa 1740
gccttggccg tggtagatgg taagaactgt gaaaataaaa atgagcattt gaagagtggt 1800
tctcatatgg agaactccat caagttgtcc actgatttgg aagatgtaac tgggaaatca 1860
tccgcagtgg gaaatggaaa agacactgat ggatgtgact taattcaaga taagaaggca 1920
acatctgaga aaaaaaaggc ggctgagggg gcaactgaag aagataaact gaatgattca 1980
gctgaatcca tcaatggtga atgtatggca aaggaaaaga acttgtcaga tgaccaggct 2040
gccgttctta ttcagtctgc ctaccgtgga tttgaagtca ggaaattaga gccactaaag 2100
aaattgaagc aaatggtgga ggtccgtgat caagcagctg agatcagaaa gcgtattcag 2160
gcccttgagt cttcttctga tttgttgaag aatgagaagg aaagagtact aattggtgaa 2220
atgataatga ggaccctact aaaactggac actatacagg gcttgcatcc aagtctcagg 2280
gatattagga aagctttgac aaaagatctt gtaaccttgc aggaggaact tgattccatt 2340
gctatagttg cagaggatga tatttccaat gatgcgggaa tgcaagaagt gcaaaacaag 2400
gttggaggaa ttcttgaaaa ctctcttaag accaatcatg acaatgtggt tgatatgaag 2460
gaaccagatg agggtaatct ttcctcaatg agggatcttg tagtgaactc tcagggtttg 2520
gagacctcag agactgctct tagtgacaca gaagtgcaag gaaaatgtga agtgagagaa 2580
ttaccacaga gaaacagcat ggagtcgcaa gtaggagaat ctgcatcaga tatggtacag 2640
gttgaggcta ccaatggagg ggttgatgtt tctcaagctg tattgacgga gaatcaaggg 2700
aaagatatta tgcatcctca acttcagcag accagctctg aggaattgac tggggcacaa 2760
cttcaggact catttgatga accaaaagct atgaatgagg ccaggatcga tggagtgaat 2820
ggtggaattc atgtagagga taatctagaa gcacaggcaa cagaattacc cctgatactg 2880
gacgatgagg aacaacctct tcaggaattg aagaatagcg aatcatcaag gaaagggaag 2940
agtgagaacg ttgatcatga agtgaaattg catgtgttag ctggttcaac tttacccgct 3000
gatgttgata atgtagatga aattgggaaa acagcaagaa atgtggattc agaaataaat 3060
ctagcagctg aactgccaat tggagcactt gaagaagacc taagctttga aaacaaagga 3120
agtgaaacca actcagaaac aaatctggta gctgaattgc ctgttggtgt actcgaagga 3180
gacctagcta ttgaaaataa agaaagtgaa atagaaaatc tggtagctga actgccagtt 3240
ggagtacttg aagaaggcga agccaaagaa agtgaaatcg ggaaggataa agggtcaagc 3300
attggagaag ctaggtacaa tggggtaacc aatataacaa ctgcaacaaa gtcaaaggtt 3360

-continued

```
gttatggtgg atgaattgtc tggaaatgca gtactcgaga tggaggaaaa cctaccattg   3420

tcttcaatag aagggaaagt gaggagtgat gatgaagtat gcaaaaatga aggaaaagat   3480

ggtggaagga ttgatgatga tcagttgccc tcccctgaat cagcaggtat aagtgtctct   3540

cctcaggcac ttgaggtaac aaatgaagat gtgcagctgc aaggagtaga tggaaataaa   3600

gaaggcaggg tgctggagaa ggaacaacag tacggtgagc cagaaagcat gattgacata   3660

gacagcagaa tggacgaggc cagtggatct gaaatcacca cagaggacac cattgctgct   3720

acaacaactt cccagatgtc tgccgatgag agggacattg tgatggaaga gaatgcaaag   3780

ctgagggaaa tgatggaaaa gctaatggaa gctgggaaag agcaattaac tgtcatatcc   3840

cagttaactg gaagagtgaa agatttagag agaaagctat ccaggaagag aaaattgagg   3900

gggccgagaa ggtacaaaag ggcaacacaa tccttcaggt agaattctgt tcaaggaata   3960

tgattatgga attgatgttg caattgtaag cctcatgagt cagttgtgtg tgttcatggt   4020

tttacgggtt gagtccacat atggcagagc gtgtaatgtt tatattgtgt gataaaaataa   4080

aaaagttgtt ttctcatcat acattcatac tatgaggttc tcgtttttgt atttggggtt   4140

tgtctgctat actgtccaat ggatggtagt gtatcaataa gagtactgct ttttc        4195


<210> SEQ ID NO 11
<211> LENGTH: 275
<212> TYPE: PRT
<213> ORGANISM: Carrizo citrange

<400> SEQUENCE: 11

Met His Gly Glu Asp Asp Lys Glu Lys Val Asn Gln Gln Phe Pro Tyr
1               5                   10                  15

Pro Phe Phe Trp Met Pro Phe Gln Thr Glu Glu Gly Glu Val Glu Lys
            20                  25                  30

Lys Asp Arg Lys Glu Lys Asn Val Ala Ser Ile Ser Ala Glu Glu Ser
        35                  40                  45

Pro Ser Asp Ser Lys Phe Met Gln Val Lys Pro Pro Glu Ser Asp Glu
    50                  55                  60

Arg Met Lys Asn Phe Glu Pro Asn Asp Asp Phe Ser Asp Asn Lys Ala
65                  70                  75                  80

Lys Ser Ser Gln Leu Met Glu Gly Thr Ala Asn Lys Lys Ile Ile Pro
                85                  90                  95

Val Arg Gln Val Glu Met Cys Arg Glu Asp His Ser Asp Ser Ala Glu
            100                 105                 110

Asn Gly Val Ala Ala Asp Asn Ser Ser Arg Thr Ser Lys Met Arg Gln
        115                 120                 125

Ser Ser Ser Pro Pro Lys Thr Thr Lys Leu Pro Pro Val Cys Leu Arg
    130                 135                 140

Leu Glu Pro Leu Ser Lys Lys Lys Asn Gly Asn Gly Asn Ser Arg Ser
145                 150                 155                 160

Pro Ser Pro Pro Gly Leu Lys Arg Gln Thr Asp Glu Tyr Val His Lys
                165                 170                 175

Pro Ser Ala Ser Ser Val Leu Lys Glu Ser Pro Pro Gln Gly Ser Gln
            180                 185                 190

Ser Ala Asp Asp Ser Phe Lys Arg Arg Gly Asp Gly Asn Pro Lys Lys
        195                 200                 205

Thr Glu Lys Lys Ala Leu Gly Val Val Asp Gly Lys Asn Cys Glu Asn
    210                 215                 220
```

-continued

Lys Asn Glu His Leu Lys Thr Gly Ser His Met Glu Asn Ser Ile Arg
225 230 235 240

Leu Ser Thr Asp Leu Glu Asp Val Ala Gly Lys Ser Ser Ala Val Arg
245 250 255

Asn Gly Lys Asp Thr Asp Gly Cys Ala Leu Ile Gln Asp Lys Lys Ala
260 265 270

Thr Ser Glu
275

<210> SEQ ID NO 12
<211> LENGTH: 381
<212> TYPE: PRT
<213> ORGANISM: Citrus clementina

<400> SEQUENCE: 12

Met Asp Asn Leu Pro His Gly Arg Ser Tyr Arg Ser Ile Pro Ser Arg
1 5 10 15

Gly Arg Pro Arg Ser Ser Tyr Ala Pro Ser Val Arg Glu Ile Pro Val
20 25 30

Gln Tyr Val Gly Ser Glu Glu Lys Gln Ser Arg Glu Ser Asn Ser Ala
35 40 45

Val Lys Ile Gln Lys Val Phe Arg Ala Phe Leu Val Arg Lys Ser Val
50 55 60

Lys Lys Ile Lys Glu Ile Arg Gly Glu Val Glu Glu Ile Glu Lys Arg
65 70 75 80

Ile Ser Thr Gly Asp Thr Ile Asp Leu Ile Ala Arg Asp Ser Gln Glu
85 90 95

Arg Leu Lys Leu Asn Glu Met Leu Met Ser Leu Leu Phe Arg Leu Asp
100 105 110

Ser Val Arg Gly Val Asp Ser Gly Val Arg Asp Cys Arg Lys Ala Val
115 120 125

Ile Lys Lys Ala Ile Ala Leu Gln Glu Phe Leu Asp Ala Ala Phe Ser
130 135 140

Ser Asn Asn Ser Arg Asn Asp Gln Asn Gly Glu Asp Glu Asn Val Val
145 150 155 160

Glu Ala Val Asp Glu Gln Asn Gln Ser Ala Gln Val Glu Cys Thr Glu
165 170 175

Glu Asn Gly Glu Arg Thr Asp Ala Phe Asp Glu Lys Glu Thr Val Glu
180 185 190

Asn Gln Asn Glu Val Gly Asp Glu Glu Thr Val Glu Asn Gln Gly Asp
195 200 205

Asp Gly Glu Ala Arg Glu Val Val Glu Glu Cys Asp Asp Val Met Pro
210 215 220

Ser Val Ser Asn Gly Pro Ala Pro Glu Glu Asn Val Gly Thr Ser Gln
225 230 235 240

Ser Glu Ser Glu Ala Asp Ser Ser Ala Asn Pro Glu Glu Asp Glu Asn
245 250 255

Ser Ser Pro Lys Gln Glu Asn Asn Ala Ala Gly Ala Gly Glu Val Glu
260 265 270

Glu Asn Val Lys Glu Ser Gly Gly Glu Gly Glu Val Glu Glu Asn Val
275 280 285

Gln Gln Ser Gly Gly Glu Gly Ala Arg Asp Glu Asn Ser Lys Asn Lys
290 295 300

Glu Leu Leu Glu Arg Met Met Glu Asp His Gly Arg Met Met Glu Met
305 310 315 320

Met Ala Gln Leu Phe Glu Arg Asn Glu Met Gln Thr Arg Leu Leu Ser
325 330 335

Ala Leu Ser His Arg Val Glu Gln Leu Glu Lys Ala Phe Met Arg Glu
340 345 350

Arg Leu Arg Arg Lys Lys Lys Lys Asn Ala Ala Gly Ala Ala Asp Gly
355 360 365

Cys Glu Thr Ser Arg Asp Asn Lys Lys Cys Gly Lys Arg
370 375 380

<210> SEQ ID NO 13
<211> LENGTH: 1187
<212> TYPE: PRT
<213> ORGANISM: Citrus sinensis

<400> SEQUENCE: 13

Met Ala Thr Gln Cys Arg Val Met Ala Ala Ala Thr Ile Val Thr Ser
1 5 10 15

Leu Val Val Met His Ile Asp Leu Pro Ser Leu Leu Ser His Leu His
20 25 30

Arg His Phe Phe Tyr Arg Gly His His Pro Pro Phe Ile Glu Pro Tyr
35 40 45

Pro Val His Tyr Ala Pro Pro Leu His His Ala Met Glu Gln Gln Arg
50 55 60

Tyr Glu Tyr Asp Lys Asp Ala His Arg Asp His Tyr Cys Cys Gly Cys
65 70 75 80

Leu Asn His Met Ser Asn Gln Arg Ile Asp Lys Gly Val Lys Ile Glu
85 90 95

Glu Gln Glu Pro Asp Val Ala Lys Lys Ser Asp Ser Val Val Pro Leu
100 105 110

Gln Ser Lys Ser Tyr Pro Tyr Pro Ile Ala Arg Ile Ser Pro Glu Tyr
115 120 125

Met Lys Lys Asn Asp Glu Pro Arg Arg Ser Phe Glu Ser Glu Val Ala
130 135 140

Glu Gln Glu Lys Val Pro Cys Asn Thr Lys Ser Asn Glu Asn Met Glu
145 150 155 160

Pro Ser Glu Gly Lys Ser Ser Glu Trp Asn Gly Trp Phe Pro Leu Asp
165 170 175

Met Asn Asn Leu Lys Pro Leu Met Gln Gly Glu Asp Glu Lys Arg Lys
180 185 190

Gln Asn Gln Gln Asn Glu Asn Gly Met Lys Gln Phe Ser Tyr Pro Val
195 200 205

Phe Trp Met Pro Ser Asn Ser Glu Gln Arg Glu Pro Glu Lys Lys Ala
210 215 220

Gln Arg Gln Gly Lys Cys Trp Leu Ser Leu Asp Thr Asn Ser Pro Lys
225 230 235 240

Phe Leu Met His Gly Glu Asp Asp Lys Glu Lys Val Asn Gln Gln Phe
245 250 255

Pro Tyr Pro Phe Phe Trp Met Pro Phe Gln Thr Glu Glu Gly Glu Val
260 265 270

Glu Lys Lys Asp Arg Lys Glu Lys Asn Val Ala Ser Ile Ser Ala Glu
275 280 285

Glu Ser Pro Ser Asp Ser Lys Phe Met Gln Val Lys Ser Pro Glu Ser
290 295 300

Asp Glu Arg Met Lys Asn Phe Glu Pro Asn Glu Asp Phe Ser Asp Asp

-continued

```
305                 310                 315                 320

Lys Ala Lys Ser Ser Gln Met Met Glu Gly Thr Ala Asn Lys Lys Ile
                325                 330                 335

Ile Pro Val Arg Gln Val Glu Met Cys Arg Glu Asp His Ser Asp Ser
            340                 345                 350

Ala Glu Lys Gly Val Ala Ala Asp Asn Ser Ser Arg Thr Ser Lys Met
        355                 360                 365

Arg Gln Ser Ser Ser Pro Pro Lys Thr Ser Lys Leu Pro Pro Val Cys
    370                 375                 380

Leu Arg Leu Glu Pro Leu Ser Lys Lys Lys Asn Gly Asn Gly Asn Ser
385                 390                 395                 400

Arg Ser Pro Ser Pro Pro Gly Leu Lys Arg Gln Ser Asp Glu Tyr Val
                405                 410                 415

His Lys Pro Ser Ala Ser Ser Val Leu Lys Glu Ser Thr Pro Gln Gly
            420                 425                 430

Ser Gln Ser Ala Asp Asp Ser Phe Lys Arg Arg Gly Asp Gly Asn Arg
        435                 440                 445

Lys Lys Thr Glu Lys Lys Ala Leu Ala Val Val Asp Gly Lys Asn Cys
    450                 455                 460

Glu Asn Lys Asn Glu His Leu Lys Ser Gly Ser His Met Glu Asn Ser
465                 470                 475                 480

Ile Lys Leu Ser Thr Asp Leu Glu Asp Val Thr Gly Lys Ser Ser Ala
                485                 490                 495

Val Gly Asn Gly Lys Asp Thr Asp Gly Cys Asp Leu Ile Gln Asp Lys
            500                 505                 510

Lys Ala Thr Ser Glu Lys Lys Lys Ala Ala Glu Gly Ala Thr Glu Glu
        515                 520                 525

Asp Lys Leu Asn Asp Ser Ala Glu Ser Ile Asn Gly Glu Cys Met Ala
    530                 535                 540

Lys Glu Lys Asn Leu Ser Asp Asp Gln Ala Ala Val Leu Ile Gln Ser
545                 550                 555                 560

Ala Tyr Arg Gly Phe Glu Val Arg Lys Leu Glu Pro Leu Lys Lys Leu
                565                 570                 575

Lys Gln Met Val Glu Val Arg Asp Gln Ala Ala Glu Ile Arg Lys Arg
            580                 585                 590

Ile Gln Ala Leu Glu Ser Ser Ser Asp Leu Leu Lys Asn Glu Lys Glu
        595                 600                 605

Arg Val Leu Ile Gly Glu Met Ile Met Arg Thr Leu Leu Lys Leu Asp
    610                 615                 620

Thr Ile Gln Gly Leu His Pro Ser Leu Arg Asp Ile Arg Lys Ala Leu
625                 630                 635                 640

Thr Lys Asp Leu Val Thr Leu Gln Glu Glu Leu Asp Ser Ile Ala Ile
                645                 650                 655

Val Ala Glu Asp Asp Ile Ser Asn Asp Ala Gly Met Gln Glu Val Gln
            660                 665                 670

Asn Lys Val Gly Gly Ile Leu Glu Asn Ser Leu Lys Thr Asn His Asp
        675                 680                 685

Asn Val Val Asp Met Lys Glu Pro Asp Glu Gly Asn Leu Ser Ser Met
    690                 695                 700

Arg Asp Leu Val Val Asn Ser Gln Gly Leu Glu Thr Ser Glu Thr Ala
705                 710                 715                 720

Leu Ser Asp Thr Glu Val Gln Gly Lys Cys Glu Val Arg Glu Leu Pro
                725                 730                 735
```

-continued

```
Gln Arg Asn Ser Met Glu Ser Gln Val Gly Glu Ser Ala Ser Asp Met
            740                 745                 750

Val Gln Val Glu Ala Thr Asn Gly Gly Val Asp Val Ser Gln Ala Val
        755                 760                 765

Leu Thr Glu Asn Gln Gly Lys Asp Ile Met His Pro Gln Leu Gln Gln
    770                 775                 780

Thr Ser Ser Glu Glu Leu Thr Gly Ala Gln Leu Gln Asp Ser Phe Asp
785                 790                 795                 800

Glu Pro Lys Ala Met Asn Glu Ala Arg Ile Asp Gly Val Asn Gly Gly
                805                 810                 815

Ile His Val Glu Asp Asn Leu Glu Ala Gln Ala Thr Glu Leu Pro Leu
            820                 825                 830

Ile Leu Asp Asp Glu Glu Gln Pro Leu Gln Glu Leu Lys Asn Ser Glu
        835                 840                 845

Ser Ser Arg Lys Gly Lys Ser Glu Asn Val Asp His Glu Val Lys Leu
    850                 855                 860

His Val Leu Ala Gly Ser Thr Leu Pro Ala Asp Val Asp Asn Val Asp
865                 870                 875                 880

Glu Ile Gly Lys Thr Ala Arg Asn Val Asp Ser Glu Ile Asn Leu Ala
                885                 890                 895

Ala Glu Leu Pro Ile Gly Ala Leu Glu Glu Asp Leu Ser Phe Glu Asn
            900                 905                 910

Lys Gly Ser Glu Thr Asn Ser Glu Thr Asn Leu Val Ala Glu Leu Pro
        915                 920                 925

Val Gly Val Leu Glu Gly Asp Leu Ala Ile Glu Asn Lys Glu Ser Glu
    930                 935                 940

Ile Glu Asn Leu Val Ala Glu Leu Pro Val Gly Val Leu Glu Glu Gly
945                 950                 955                 960

Glu Ala Lys Glu Ser Glu Ile Gly Lys Asp Lys Gly Ser Ser Ile Gly
                965                 970                 975

Glu Ala Arg Tyr Asn Gly Val Thr Asn Ile Thr Thr Ala Thr Lys Ser
            980                 985                 990

Lys Val Val Met Val Asp Glu Leu  Ser Gly Asn Ala Val  Leu Glu Met
        995                 1000                 1005

Glu Glu  Asn Leu Pro Leu Ser  Ser Ile Glu Gly Lys  Val Arg Ser
    1010                 1015                 1020

Asp Asp  Glu Val Cys Lys Asn  Glu Gly Lys Asp Gly  Gly Arg Ile
    1025                 1030                 1035

Asp Asp  Asp Gln Leu Pro Ser  Pro Glu Ser Ala Gly  Ile Ser Val
    1040                 1045                 1050

Ser Pro  Gln Ala Leu Glu Val  Thr Asn Glu Asp Val  Gln Leu Gln
    1055                 1060                 1065

Gly Val  Asp Gly Asn Lys Glu  Gly Arg Val Leu Glu  Lys Glu Gln
    1070                 1075                 1080

Gln Tyr  Gly Glu Pro Glu Ser  Met Ile Asp Ile Asp  Ser Arg Met
    1085                 1090                 1095

Asp Glu  Ala Ser Gly Ser Glu  Ile Thr Thr Glu Asp  Thr Ile Ala
    1100                 1105                 1110

Ala Thr  Thr Thr Ser Gln Met  Ser Ala Asp Glu Arg  Asp Ile Val
    1115                 1120                 1125

Met Glu  Glu Asn Ala Lys Leu  Arg Glu Met Met Glu  Lys Leu Met
    1130                 1135                 1140
```

-continued

```
Glu Ala  Gly Lys Glu Gln Leu  Thr Val Ile Ser Gln  Leu Thr Gly
    1145                 1150                 1155

Arg Val  Lys Asp Leu Glu Arg  Lys Leu Ser Arg Lys  Arg Lys Leu
    1160                 1165                 1170

Arg Gly  Pro Arg Arg Tyr Lys  Arg Ala Thr Gln Ser  Phe Arg
    1175                 1180                 1185
```